(12) United States Patent
Matsumoto

(10) Patent No.: US 12,118,817 B2
(45) Date of Patent: Oct. 15, 2024

(54) POSE DATA GENERATION DEVICE, CG DATA GENERATION SYSTEM, POSE DATA GENERATION METHOD, AND NON-TRANSITORY COMPUTER READABLE STORAGE MEDIUM

(71) Applicant: MegaChips Corporation, Osaka (JP)

(72) Inventor: Mahito Matsumoto, Osaka (JP)

(73) Assignee: MEGACHIPS CORPORATION, Osaka (JP)

( * ) Notice: Subject to any disclaimer, the term of this patent is extended or adjusted under 35 U.S.C. 154(b) by 45 days.

(21) Appl. No.: 17/690,015

(22) Filed: Mar. 9, 2022

(65) Prior Publication Data

US 2022/0207903 A1  Jun. 30, 2022

Related U.S. Application Data

(63) Continuation of application No. PCT/JP2021/002034, filed on Jan. 21, 2021.

(30) Foreign Application Priority Data

Mar. 11, 2020 (JP) .................................. 2020-041836

(51) Int. Cl.
*G06T 7/70* (2017.01)
*G06T 17/00* (2006.01)
*G06V 40/10* (2022.01)

(52) U.S. Cl.
CPC .............. *G06V 40/103* (2022.01); *G06T 7/70* (2017.01); *G06T 17/00* (2013.01); *G06T 2200/04* (2013.01); *G06T 2207/30196* (2013.01)

(58) Field of Classification Search
CPC ......... G06V 40/103; G06T 7/70; G06T 17/00; G06T 2200/04; G06T 2207/30196
(Continued)

(56) References Cited

U.S. PATENT DOCUMENTS 6,545,673 B1  4/2003  Shiitani et al.
2006/0274947 A1  12/2006  Fujimura et al.
(Continued)

FOREIGN PATENT DOCUMENTS

JP  2000-259855 A  9/2000
JP  2005-128775 A  5/2005
(Continued)

OTHER PUBLICATIONS

Gilbert, "Fusing Visual and Inertial Sensors with Semantics for 3D Human Pose Estimation" (Year 2019), International Journal of Computer Vision (2019) 127:381-397; (Publication Year 2019).*
(Continued)

*Primary Examiner* — Hai Tao Sun
(74) *Attorney, Agent, or Firm* — XSENSUS LLP

(57) ABSTRACT

Provided is a system that estimates pose data of a person with high accuracy at low cost. At a time step at which image data is to be captured and obtained, a pose data generation system obtains pose data based on the image data. At a time step at which image data is not to be obtained, the pose data generation system predicts pose data at a current time step from a previous time step using IMU data and performs interpolation processing to obtain pose data. Thus, even when a rate of obtaining the image data is low, the pose data generation system performs the above interpolation processing using IMU data to obtain pose data with a high frame rate.

13 Claims, 30 Drawing Sheets

(58) Field of Classification Search
USPC .......................................................... 345/419
See application file for complete search history.

(56) References Cited

U.S. PATENT DOCUMENTS

| | | | | |
|---|---|---|---|---|
| 2017/0286750 | A1* | 10/2017 | Levinshtein | G06V 20/64 |
| 2018/0286056 | A1* | 10/2018 | Kaino | G06T 7/70 |
| 2019/0213712 | A1* | 7/2019 | Shoa Hassani Lashdan | G06T 7/248 |
| 2020/0074738 | A1* | 3/2020 | Hare | G11B 27/031 |
| 2020/0364519 | A1* | 11/2020 | Evangelidis | G06F 18/23 |

FOREIGN PATENT DOCUMENTS

| | | |
|---|---|---|
| JP | 2008-537815 A | 9/2008 |
| JP | 2015-185020 A | 10/2015 |
| WO | 2006/099597 A2 | 9/2006 |

OTHER PUBLICATIONS

International Search Report and Written Opinion mailed on Apr. 13, 2021, received for PCT Application PCT/JP2021/002034, Filed on Jan. 21, 2021, 10 pages including English Translation.

Gilbert et al., "Fusing Visual and Inertial Sensors with Semantics for 3D Human Pose Estimation", International Journal of Computer Vision, vol. 127, 2019, pp. 381-397.

Pons-Moll et al., "Multisensor-Fusion for 3D Full-Body Human Motion Capture", Conference Paper in Proceedings/CVPR, IEEE Computer Society Conference on Computer Vision and Pattern Recognition, Jun. 2010, pp. 663-670.

Japanese Office Action issued Dec. 19, 2023, in corresponding Japanese Patent Application No. 2020-041836, 7 pages.

* cited by examiner

POSE DATA GENERATION DEVICE, CG DATA GENERATION SYSTEM, POSE DATA GENERATION METHOD, AND NON-TRANSITORY COMPUTER READABLE STORAGE MEDIUM

CROSS-REFERENCE TO RELATED APPLICATIONS

This application is a Bypass continuation of PCT filing PCT/JP2021/002034, filed Jan. 21, 2021, and claims priority to Japanese Application No. 2020-041836, filed Mar. 11, 2020, the entire contents of each are incorporated herein by reference.

TECHNICAL FIELD

The present invention relates to a technique for estimating poses of a person, a living thing, an object, or the like, which is movable and whose posture is variable.

BACKGROUND ART

In recent years, motion capture, which is a technique for recording the movement of a real person or an object, has attracted attention, and in order to realize high-precision motion capture, a technique for estimating a person's pose with high accuracy is required.

For example, Non-Patent Document 1 discloses a technique for obtaining three-dimensional pose data of a subject person by performing neural network processing using the three-dimensional data of the subject person (three-dimensional shape data of the subject person) obtained from images of the person to be processed (the subject person) captured by imaging devices installed at multiple different positions and data obtained by inertial measurement units (IMUs) attached to multiple parts of the subject person.

In addition, Non-Patent Document 2 discloses a technology for obtaining pose data of a subject person by performing prediction processing using data obtained by fusing images of the subject person captured by an imaging device and data (IMU data) obtained by inertial measurement devices attached to multiple parts of the subject person. Specifically, the technique of Non-Patent Document 2 performs prediction processing using a linear equation that combines a linear equation derived from IMU data (direction data) and a linear equation derived from a silhouette image obtained from captured image of the subject person, thereby obtaining pose data of the subject person.

PRIOR ART DOCUMENTS

Non Patent Document 1: Andrew Gilbert, Matthew Trumble, Charles Malleson, Adrian Hilton, John Collomosse, "Fusing Visual and Inertial Sensors with Semantics for 3D Human Pose Estimation" International Journal of Computer Vision (2019) 127:381-397.

Non Patent Document 2: Gerard Pons-Moll, Andreas Baak, Thomas Helten, Meinard Mueller, Hans-Peter Seidel, Bodo Rosenhahn, "Multisensor-Fusion for 3D Full-Body Human Motion Capture" Conference Paper in Proceedings/CVPR, IEEE Computer Society Conference on Computer Vision and Pattern Recognition. IEEE Computer Society Conference on Computer Vision and Pattern Recognition June 2010

Disclosure of Invention

Technical Problem

However, the technique of Non-Patent Document 1 needs to provide (1) a neural network that inputs three-dimensional data of a subject person obtained from a video and (2) a neural network that inputs IMU data, and further (3) provide a neural network that integrates the outputs of the above two neural networks to perform learning. In other words, the technique of Non-Patent Document 1 needs to perform a learning process using a complicated learning model in order to obtain a trained model; the load for constructing the trained model is large. Further, the technique of Non-Patent Document 1 performs prediction processing using a trained model having a complicated configuration, and thus, for example, when realized by hardware, the scale of the hardware becomes large; as a result, the cost for realizing the technique of Non-Patent Document 1 is also high.

The above-described technique of Non-Patent Document 2 performs prediction processing using a linear equation obtained by combining a linear equation derived from IMU data (direction data) and a linear equation derived from a silhouette image obtained from an image of a subject person, thereby obtaining the pose data of the subject person. Thus, the technique of Non-Patent Document 2 needs to constantly obtain IMU data and silhouette images (image data obtained from an image obtained by capturing the subject person). In obtaining high-precision pose data by the technique of Non-Patent Document 2, it is necessary to increase the frame rate for the captured moving images of the subject person; as a result, it is necessary to perform prediction processing at short time intervals corresponding to the high frame rate. In other words, when obtaining high-precision pose data, the technique of Non-Patent Document 2 needs to always obtain both IMU data and silhouette image at a high frame rate and perform prediction processing using both data. As described above, in order to obtain high-precision pose data by the technique of Non-Patent Document 2, a device capable of processing at a high frame rate is required, so that the cost for realizing the technique of Non-Patent Document 2 is high.

To solve the above problems, it is an object of the present invention to provide a pose data generation device, a CG data generation system, a pose data generation method, and a program that can be realized at low cost and obtain high-precision pose data.

Solution to Problem

To solve the above problems, a first aspect of the present invention provides a pose data generation device including image-based pose data obtaining circuitry, IMU data obtaining processing circuitry, and interpolation circuitry.

The image-based pose data obtaining circuitry obtains image-based pose data, which is data including posture information of a subject, from image data obtained by imaging the subject in a three-dimensional space at a time step $t$ ($t$ is an integer).

The IMU data obtaining processing circuitry obtains IMU data outputting from an inertial measurement unit attached to the subject, the IMU data including at least one of position data, displacement data, velocity data, acceleration data, and angular velocity data in the three-dimensional space of the inertial measurement unit attached to the subject.

Assuming that a timing at which image data is obtained next to image data obtained at a time step $t$ is a time step $t+k$ (k is a natural number), the interpolation circuitry performs interpolation processing based on the image-based pose data obtained using the image data that has been obtained by the image-based pose data obtaining circuitry at the time t in a first period, which is a period after the time step t and before the time step t+k, and the IMU data obtained by the IMU data obtaining processing circuitry in the first period, thereby obtaining interpolation pose data that is interpolated data for pose data of the subject.

(1) At a time step at which image data is to be captured and obtained, the pose data generation system obtains pose data based on the image data. (2) At a time step at which image data is not to be obtained (in a period in which image data has not been obtained), the pose data generation system predicts pose data at a current time step from a previous time step using IMU data and performs interpolation processing to obtain pose data. Thus, even when a rate of obtaining the image data is low, the pose data generation system performs the above interpolation processing using IMU data to obtain pose data with a high frame rate.

In other words, since the pose data generation system does not need to use an imaging device for high frame rates, it can be realized at low cost, and can obtain pose data by interpolation processing using IMU data, thereby obtaining highly accurate pose data.

Note that the "image data" may be one or more pieces of image data.

Further, the "image data" may be one or a plurality of images captured from spatially different positions, or one or a plurality of temporally different images (for example, a plurality of consecutive frames in a time series).

Further, the "pose data" is data for specifying a pose. The "pose" is a concept including a posture; the pose should not be limited to the pose of a person, and may be a concept including one that can be a target to be posture-controlled for any object. Poses can be specified, modified, and/or adjusted using, for example, a matrix, a quaternion, or Euler angles.

Further, the "subject" is a concept including a person, a living thing, an object, or the like, which is movable and whose posture is variable.

A second aspect of the present invention provides the pose data generation device of the first aspect of the present invention in which the image-based pose data obtaining circuitry obtains the image-based pose data, which is three-dimensional data, from the image data.

This allows the pose data generation device to perform processing using image-based pose data, which is three-dimensional data.

A third aspect of the present invention provides the pose data generation device of the first aspect of the present invention in which the image-based pose data obtaining circuitry obtains the image-based pose data, which is two-dimensional data, from the image data.

The IMU data is three-dimensional data.

The IMU data obtaining processing circuitry performs a three-dimension to two-dimension conversion processing on the IMU data, which is three-dimensional data, to obtain IMU data that is two-dimensional data.

This allows the pose data generation device to perform processing using the two-dimensional image-based pose data obtained from the image data and the IMU data which is the two-dimensional data.

A fourth aspect of the present invention provides the pose data generation device of the first aspect of the present invention further includes error obtaining circuitry and 2D/3D conversion circuitry.

The image-based pose data obtaining circuitry obtains the image-based pose data, which is two-dimensional data, from the image data.

The IMU data is three-dimensional data.

The interpolation pose data is three-dimensional data.

The error obtaining circuitry obtains two-dimensional error data, which is data including an error between the image-based pose data and the two-dimensional interpolation pose data, which is data obtained by converting the interpolation pose data, which is three-dimensional data, into two-dimensional data.

The 2D/3D conversion circuitry that obtains three-dimensional error data by converting the two-dimensional error data into three-dimensional data.

The interpolation circuitry performs processing for correcting the error based on the three-dimensional error data on the interpolation pose data to obtain interpolation pose data after error correction processing.

This allows the pose data generation device to perform processing using the interpolation pose data obtained by the processing for correcting the error based on the three-dimensional error data, thus allowing the pose data generation processing to be performed with higher accuracy.

A fifth aspect of the present invention provides the pose data generation device of one of the first to the fourth aspects of the present invention in which assuming that a frame rate of the pose data generated by the pose data generation device is $R_1$ fps ($R_1$ is a real number, fps:frames per second), the image-based pose data obtaining circuitry obtains the image-based pose from the image data obtained at a frame rate of $0.5 \times R_1$ fps or less.

This allows the pose data generation device to obtain high-rate image-based pose data by using the image data obtained at a low rate. For example, when two pieces of pose data is to be obtained by the interpolation processing in a period between the time steps in which the image-based pose data obtaining circuitry obtains the image-based pose data from the image data obtained at a frame rate of 10 fps ($\leq 0.5 \times 30$ fps) and the image data is obtained, a frame rate of pose data obtained (generated) by the pose data generation device is 30 fps (=10 fps×3). Thus, the pose data generation device obtains high-rate pose data by using low-rate image data.

A sixth aspect of the present invention provides the pose data generation device of one of the first to the third aspects of the present invention in which at the time step at which the image data is to be obtained, the interpolation circuitry compares the image-based pose data obtained from the image data with the interpolation pose data obtained by the interpolation processing.

(1) When a difference between the image-based pose data obtained from the image data and the interpolation pose data obtained by the interpolation processing is larger than a predetermined threshold value, the interpolation circuitry sets the image-based image obtained from the image data as output data from the pose data generation device.

(2) When a difference between the image-based pose data obtained from the image data and the interpolation pose data obtained by the interpolation processing is equal to or less than the predetermined threshold value, the interpolation circuitry sets the interpolation pose data obtained by the interpolation processing as output data from the pose data generation device.

This allows the pose data generation device to verify the accuracy for a difference between the image-based pose data obtained from the image data and the interpolation pose data obtained by the interpolation processing at the time step when the image data has been obtained. In other words, the pose data generation device can verify the accuracy of the interpolation processing at the time step at which the image data has been obtained. When it is determined that the accuracy of the interpolation processing is poor, the pose data generation device sets the image-based pose data obtained from the image data as output data, thus allowing the accuracy of the pose data obtained by the pose data generation device to be always maintained at a certain level or higher.

A seventh aspect of the present invention provides the pose data generation device of one of the first to the sixth aspects of the present invention in which the interpolation circuitry performs the interpolation processing by performing processing using a time series filter.

This allows the pose data generation device to perform interpolation processing using a time series filter; for example, when the movement of a target to be processed (for example, a person) can be expressed (predicted) by the equation of motion, or the like, the pose data generation device applies a time series filter (for example, Kalman filter, the extended Kalman filter, the unscented Kalman filter, Particle filter, or the like) using data predicted by the equation of motion, or the like and the actual observation data (data specified from the IMU data), thereby allowing for performing interpolation processing for pose data.

An eighth aspect of the present invention provides a CG data generation system including the pose data generation device of the third aspect of the present invention, and CG data generation circuitry that generates two-dimensional CG data from three-dimensional CG data and generates two-dimensional CG data from two-dimensional pose data.

The CG data generation circuitry performs processing for converting three-dimensional CG data to two-dimensional CG data based on conversion parameters, which the IMU data obtaining processing circuitry has used in 3D-to-2D conversion processing for obtaining IMU data which is 2D data, to obtain CG data for two-dimensional synthesis, and synthesize the obtained CG data for two-dimensional synthesis and two-dimensional CG data generated from the two-dimensional pose data to obtain CG data for outputting.

The CG data generation system performs CG synthesis on two-dimensional pose data obtained by the pose data generation device to obtain a two-dimensional CG image corresponding to the two-dimensional pose data.

Note that in the CG data generation system, the parameters of the 3D-to-2D conversion processing when the three-dimensional IMU data is converted into the two-dimensional IMU data may be matched with the parameters of the 3D-to-2D conversion processing. This allows the 3D-to-2D conversion processing to be made common, thus allowing for simplifying the 3D-to-2D conversion processing.

A ninth aspect of the present invention provides a CG data generation system including the pose data generation device of the fourth aspect of the present invention, three-dimensional CG data generation circuitry, and two-dimensional CG data generation circuitry.

The three-dimensional CG data generation circuitry performs CG processing based on three-dimensional pose data to generate three-dimensional CG data.

The two-dimensional CG data generation circuitry performs 3D/2D conversion processing for converting three-dimensional CG data generated by the three-dimensional CG data generation circuitry to two-dimensional data to obtain two-dimensional CG data.

The error obtaining circuitry uses two-dimensional pose data corresponding to the two-dimensional CG data obtained by the two-dimensional CG data generation circuitry as the two-dimensional interpolation pose data, and obtains two-dimensional error data that is data including the two-dimensional interpolation pose data and the image-based pose data.

This allows the CG data generation system to perform processing using the interpolation pose data obtained by the processing for correcting the error based on the three-dimensional error data, thus allowing more accurate pose data generation processing and CG data generation processing to be performed.

A tenth aspect of the present invention provides a pose data generation method including an image-based pose data obtaining step, an IMU data obtaining processing step, and an interpolation step.

The image-based pose data obtaining step obtains image-based pose data, which is data including posture information of a subject, from image data obtained by imaging the subject in a three-dimensional space at a time step t (t is an integer).

The IMU data obtaining processing step obtains IMU data outputting from an inertial measurement unit attached to the subject, the IMU data including at least one of position data, displacement data, velocity data, acceleration data, and angular velocity data in the three-dimensional space of the inertial measurement unit attached to the subject.

The interpolation step, assuming that a timing at which image data is obtained next to image data obtained at a time step t is a time step t+k (k is a natural number), performs interpolation processing based on the image-based pose data obtained using the image data that has been obtained by the image-based pose data obtaining circuitry at the time t in a first period, which is a period after the time step t and before the time step t+k, and the IMU data obtained by the IMU data obtaining processing circuitry in the first period, thereby obtaining interpolation pose data that is interpolated data for pose data of the subject.

This achieves the pose data generation method having the same advantageous effects as the pose data generation device of the first aspect of the present invention.

The eleventh aspect of the present invention provides a non-transitory computer readable storage medium storing a program for causing a computer to execute the pose data generation method of the tenth aspect of the present invention.

This achieves the non-transitory computer readable storage medium storing a program for causing a computer to execute the pose data generation method, the non-transitory computer readable storage medium having the same advantageous effects as the pose data generation device of the first aspect of the present invention.

Advantageous Effects

The present invention provides a pose data generation device, a CG data generation system, a pose data generation method, and a program that can be realized at low cost and obtain high-precision pose data.

DESCRIPTION OF EMBODIMENTS

First Embodiment

A first embodiment will be described below with reference to the drawings.

1.1: Configuration of pose data generation system FIG. 1 is a schematic configuration diagram of a pose data generation system 1000 according to the first embodiment.

Figure 2:
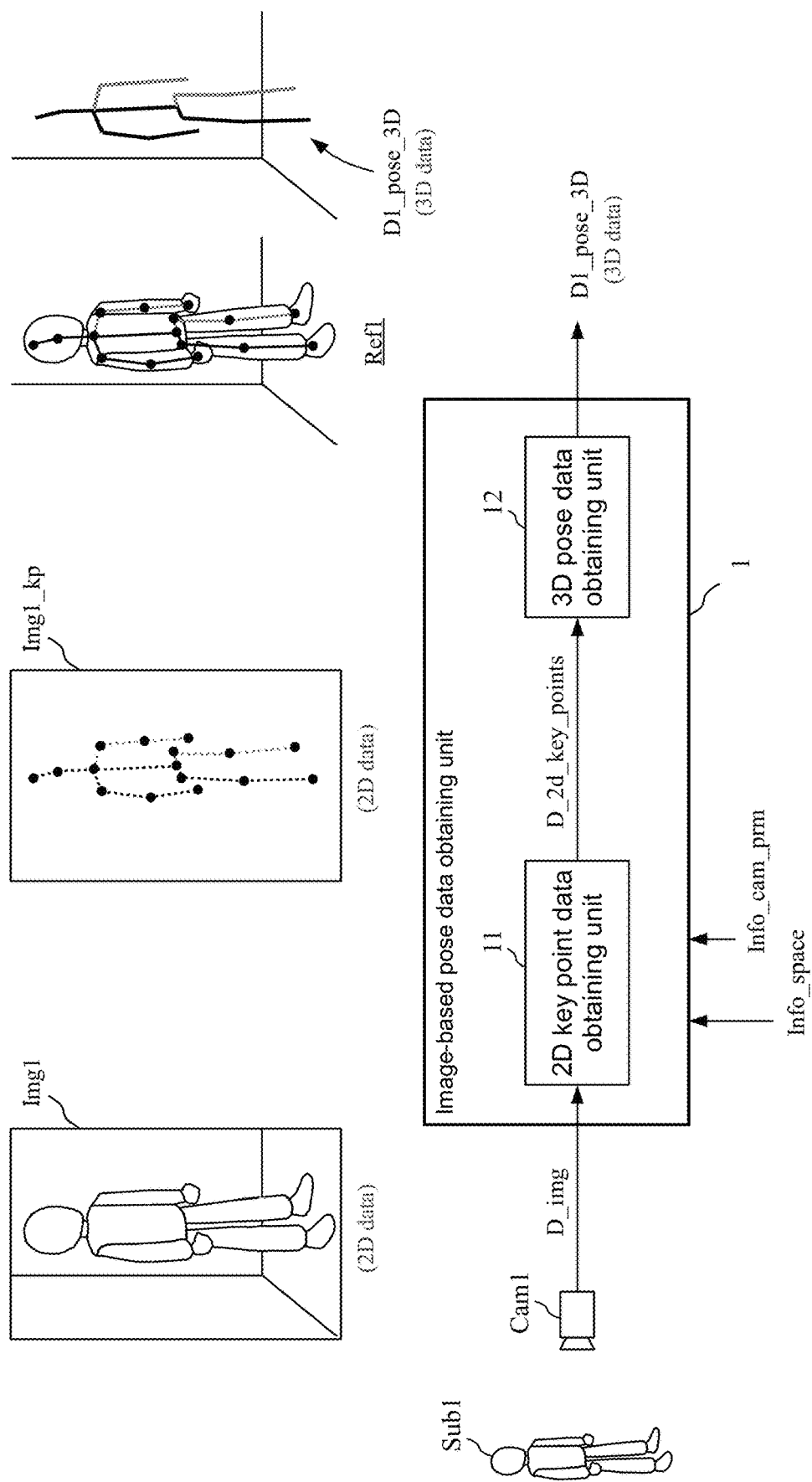
FIG. 2 is a schematic configuration diagram of an image-based pose data obtaining unit 1 according to the first embodiment.

FIG. 2 is a schematic configuration diagram of the image-based pose data obtaining unit 1 according to the first embodiment.

Figure 1:
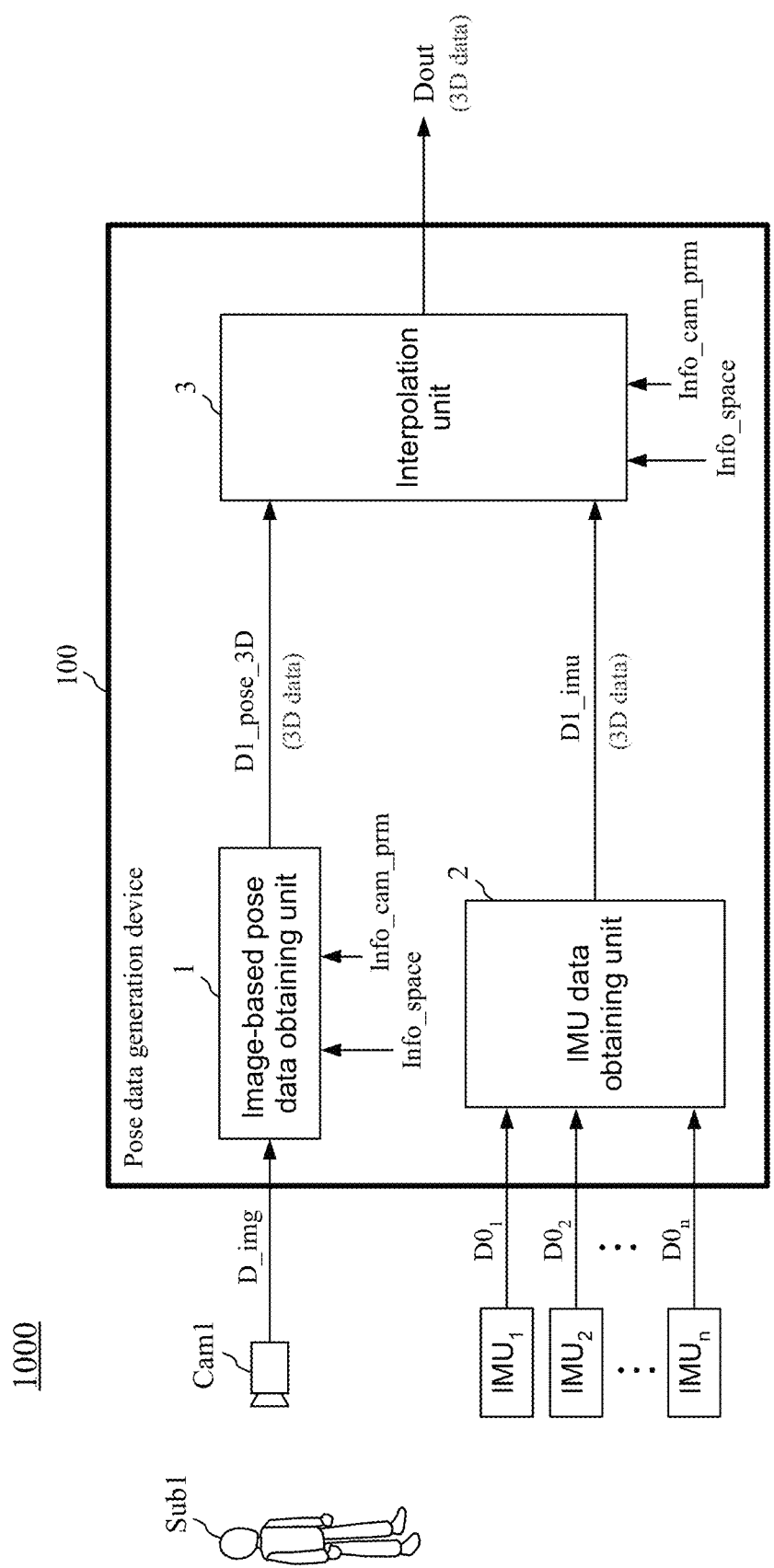
FIG. 1 is a schematic configuration diagram of a pose data generation system 1000 according to a first embodiment.

As shown in FIG. 1, the pose data generation system 1000 includes an imaging device Cam1 for photographing a subject person Sub1, n (n is a natural number) inertial measurement units $IMU_1$ to $IMU_n$ attached to the subject person Sub1, and a pose data generation device 100.

The imaging device Cam1 includes an optical system that collects subject light (for example, an optical system composed of a plurality of lenses) and an image sensor that converts the light collected by the optical system into an electric signal by the photoelectric effect. The imaging device Cam1 can shoot moving images and obtains, for example, frame images (two-dimensional images) that are continuous in time series and constitute moving images by photographing the subject person Sub1. The imaging device Cam1 transmits, for example, the frame image data (two-dimensional image data) obtained by photographing the subject person Sub1 to the image-based pose data obtaining unit 1 as data D_img.

The inertial measurement unit $IMU_1$ is equipped with, for example, an acceleration measuring instrument, a gyroscope, a magnetic sensor, a pressure sensor, and the like, and a device for obtaining an angle (attitude), an angular velocity, position data, displacement data, and velocity data of an object to which the inertial measuring unit is attached. Note that inertial measurement units $IMU_2$ to $IMU_n$ have the same configuration and functions as the inertial measurement unit $IMU_1$.

The inertial measurement units $IMU_1$ to $IMU_n$ are attached to different positions of the subject person Sub1. The inertial measurement unit $IMU_k$ (k is a natural number satisfying 1≤k≤n) obtains data including at least one of an angle (attitude), an angular velocity, position data, displacement data, and velocity data of the subject person Sub1 at its attached position, as IMU data. The inertial measurement unit $IMU_k$ then transmits the obtained IMU data as data $D0_k$ to the IMU data obtaining unit 2. The inertial measurement unit $IMU_k$ has the capability to communicate with the pose data generation device 100 by using wired or wireless data communication.

The pose data generation device 100 includes an image-based pose data obtaining unit 1, an IMU data obtaining unit 2 (IMU data obtaining processing unit), and an interpolation unit 3.

The image-based pose data obtaining unit 1 receives frame image data D_img transmitted from the imaging device Cam1, information Info_space about a three-dimensional space (imaging space) imaged by the imaging device Cam1, and imaging parameters Info_cam_prm of the imaging device Cam1 (for example, information about the installation position of the imaging device Cam1 and the optical axis of the lens optical system of the imaging device Cam1 (direction of the optical axis, or the like), image angle, aperture, focal length, shutter speed, or the like). The information Info_space regarding the imaging space may be stored in advance in a storage unit (not shown) of the pose data generation device 100; alternatively, it may be inputted via a user interface (not shown) of the pose data generation device 100 by a user, for example. Information about the imaging space Info_space includes information for specifying the three-dimensional space (imaging space) to be imaged by the imaging device Cam1, and is used when a predetermined coordinate system in the imaging space is set. For example, the information Info_space regarding the imaging space can be set by comparing the pose data (image-based pose data) obtained from the frame image data (two-dimensional image data) D_img with predetermined pose data stored in the storage unit. The imaging parameters of the imaging device Cam1 may be stored in advance in a storage unit (not shown) of the pose data generation device 100; alternatively, they may be inputted via a user interface (not shown) of the pose data generation device 100 by a user, for example.

The image-based pose data obtaining unit 1 performs pose data obtaining process using the frame image data D_img continuously inputted in time series, thereby obtaining pose data (image-based pose data) of the subject person Sub1. The image-based pose data obtaining unit 1 then transmits the obtained image-based pose data as data D1_pose_3D to the interpolation unit 3.

As shown in FIG. 2, the image-based pose data obtaining unit 1 includes, for example, a 2D key point data obtaining unit 11 and a 3D pose data obtaining unit 12.

The 2D key point data obtaining unit 11 receives the frame image data D_img transmitted from the imaging device Cam1. The 2D key point data obtaining unit 11 obtains key point data indicating the positions of predetermined portions of the subject person Sub1 from the received frame image data D_img. Specifically, the 2D key point data obtaining unit 11 (1) extracts image regions corresponding to the subject person Sub1 in the frame image formed by frame image data D_img, and (2) determines positions (positions in the two-dimensional image) of the predetermined portions of the subject person Sub1 in the frame image based on the imaging space information Info_space inputted into the image-based pose data obtaining unit 1 and the information Info_cam_prm for the imaging parameters of the imaging device Cam1. As a result, the 2D key point data obtaining unit 11 obtains the key point data (key point data obtaining processing by the top-down posture estimation method). The key point data is, for example, data including information about coordinates in a two-dimensional image of positions (a plurality of positions) of predetermined portions of the subject person Sub1.

Note that the 2D key point data obtaining unit 11 may perform key point data obtaining processing by the bottom-up posture estimation method to obtain key point data instead of the above processing (key point data obtaining processing by the top-down posture estimation method). Specifically, the 2D key point data obtaining unit 11 first extracts the key points that are the keys to the posture estimation, and then matches the key points for each person. The 2D key point data obtaining unit 11 then retains only the matched key points, and set the retained key points as the key points of the subject person Sub1. The 2D key point data obtaining unit 11 obtains key point data for the key points set as described above (key point data obtaining processing by the bottom-up posture estimation method).

The 2D key point data obtaining unit 11 then transmits the obtained key point data to the 3D pose data obtaining unit 12 as data D_2d_key_points.

The 3D pose data obtaining unit 12 receives the key point data D_2d_key_points transmitted from the 2D key point data obtaining unit 11. The 3D pose data obtaining unit 12 obtains a three-dimensional pose data from the key point data D_2d_key_points based on the information Info_space of the imaging space inputted into the image-based pose data obtaining unit 1 and the information Info_cam_prm of the imaging parameters of the imaging device Cam1. Specifically, the 3D pose data obtaining unit 12 estimates positions (coordinate positions) in the coordinate system of the three-dimensional space, the coordinate system being set for the pose data generation device 100, the positions corresponding to points in the frame image (two-dimensional image) indicated by the key point data D_2d_key_points (two-dimensional coordinate data), thereby obtaining the three-dimensional coordinate information of the estimated positions. The 3D pose data obtaining unit 12 then obtains the data including the three-dimensional coordinate data of the points (plurality of points) in the three-dimensional space corresponding to the key point data estimated above, as the three-dimensional pose data D1_pose_3D. The 3D pose data obtaining unit 12 then transmits the obtained three-dimensional pose data (three-dimensional image-based pose data) D1_pose_3D to the interpolation unit 3.

The IMU data obtaining unit 2 receives data $D0_1$ to $D0_1$ transmitted from the inertial measurement units $IMU_1$ to $IMU_n$, respectively. The IMU data obtaining unit 2 obtains, as data D1_imu, data in which $D0_1$ to $D0_1$ are integrated, and then transmits the obtained data D1_imu to the interpolation unit 3.

The interpolation unit 3 receives the data D1_pose_3D transmitted from the image-based pose data obtaining unit 1 and the data D1_imu transmitted from the IMU data obtaining unit 2. Further, the interpolation unit 3 receives information Info_space regarding the three-dimensional space (imaging space) imaged by the imaging device Cam1 and the imaging parameters Info_cam_prm of the imaging device Cam1.

(1) When the pose data D1_pose_3D is first inputted from the image-based pose data obtaining unit 1 at the time step at which the frame image data has been obtained, the interpolation unit 3 transmits the inputted pose data D1_pose_3D as output data Dout (three-dimensional pose data Dout), and stores and holds the output data Dout.

(2) Based on the information Info_space regarding the imaging space and the imaging parameters Info_cam_prm of the imaging device Cam1, the interpolation unit 3 performs interpolation processing at a time step, at which the frame image data has not been obtained, using the pose data Dout stored in the interpolation unit 3 and the data D1 imu obtained at the current time step, thereby obtaining pose data after interpolation processing. The interpolation unit 3 then transmits the obtained pose data after interpolation processing as output data Dout, and stores and holds the output data Dout.

(3) Based on the information Info_space regarding the imaging space and the imaging parameters Info_ cam_prm of the imaging device Cam1, the interpolation unit 3 performs interpolation processing at a time step, at which the frame image data has been obtained, using the pose data Dout stored in the interpolation unit 3 and the data D1_imu obtained at the current time step, thereby obtaining pose data after interpolation processing. Further, the interpolation unit 3 compares the inputted pose data D1_pose_3D (pose data obtained from the frame image data) with the pose data after interpolation processing; according to the result of the comparison, the interpolation unit 3 selects one of the inputted pose data D1_pose_3D (pose data obtained from the frame image data) and the pose data after the above interpolation processing. The interpolation unit 3 then transmits the selected pose data as output data Dout, and stores and holds the output data Dout.

1.2: Operation of pose data generation system The operation of the pose data generation system 1000 configured as described above will be described below.

Figure 3:
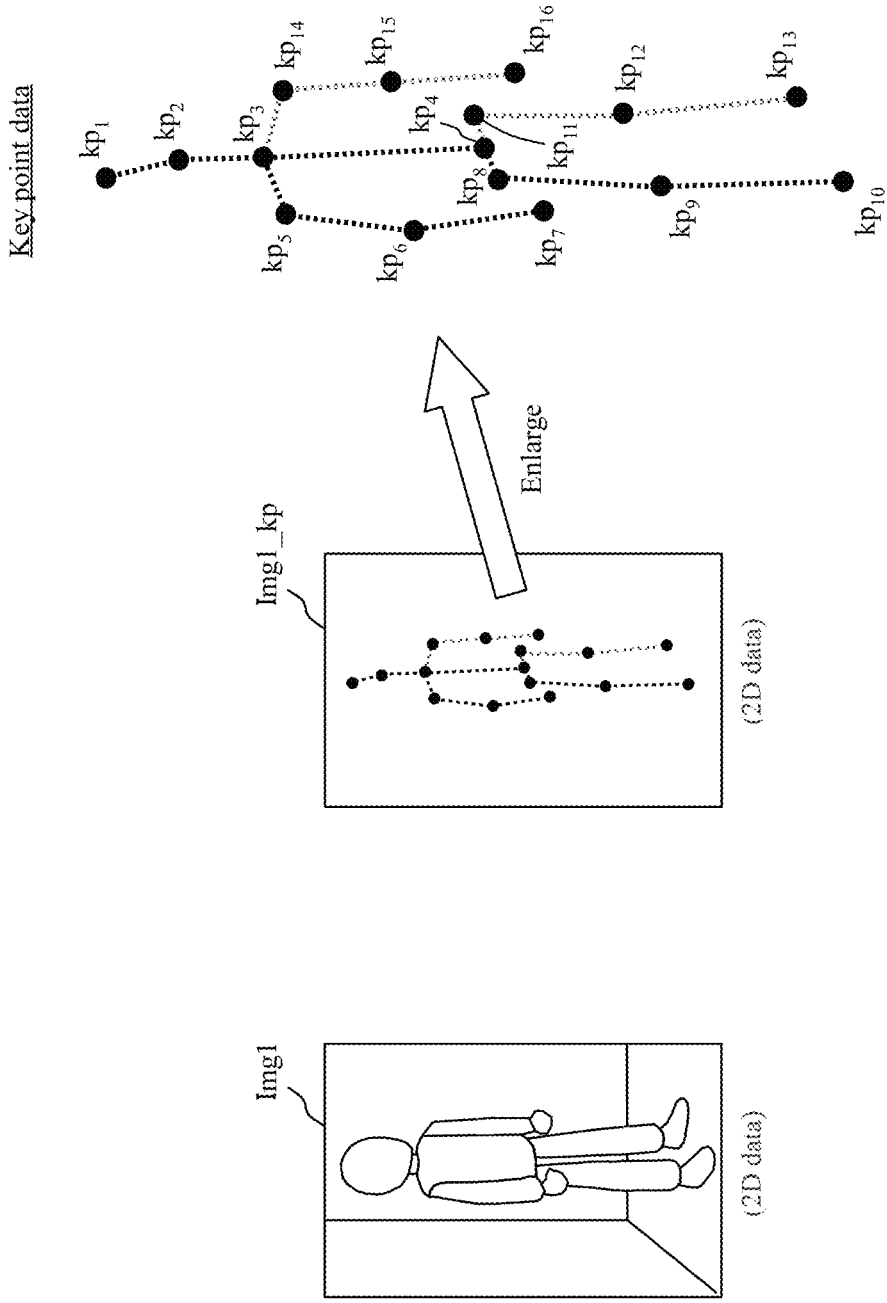
FIG. 3 is a diagram for explaining key point data.

FIG. 3 is a diagram for explaining key point data.

Figure 4:
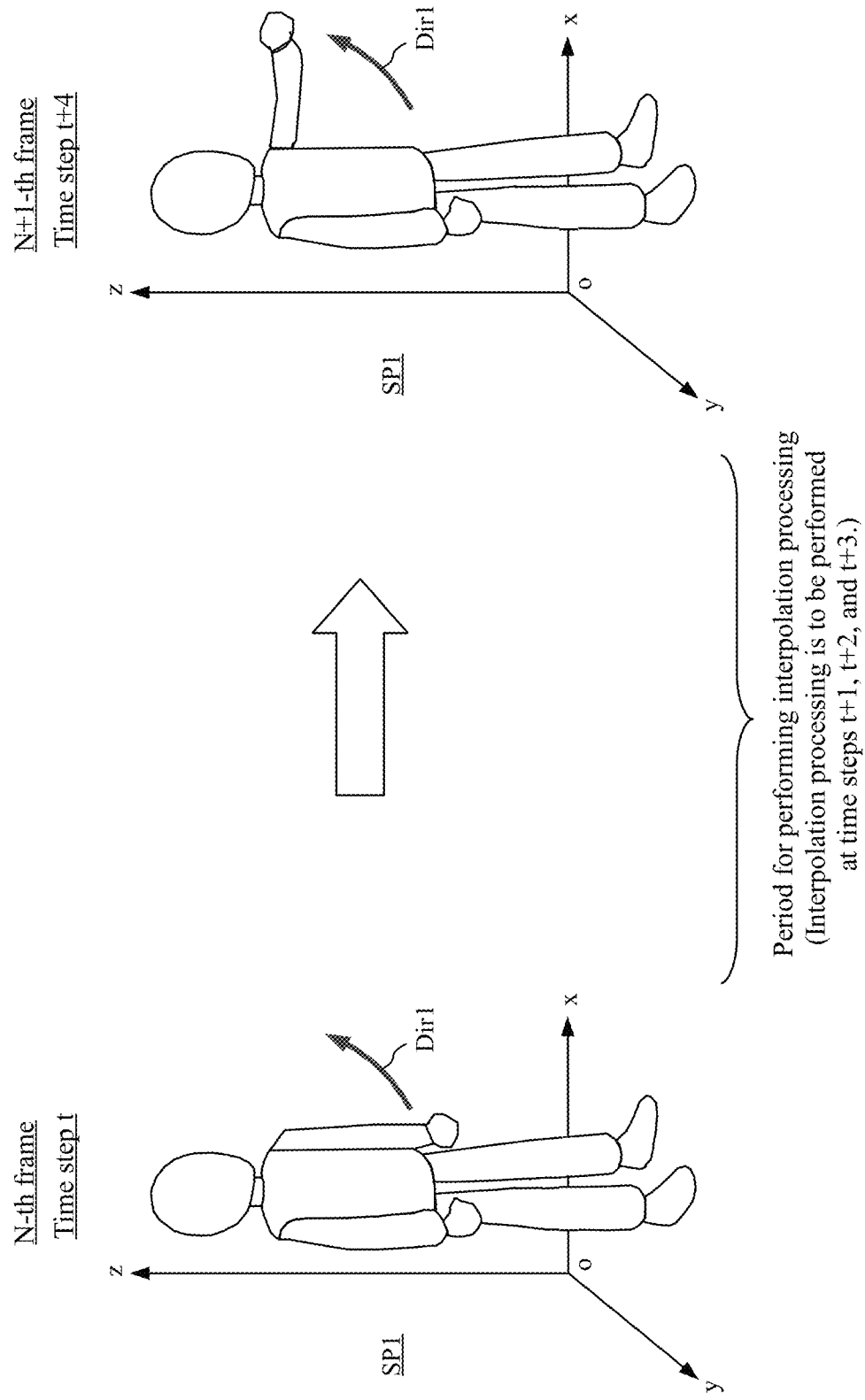
FIG. 4 is a diagram schematically showing a posture of a subject person Sub1 at a time step t at which an N-th frame image has been captured by an imaging device Cam1 and at a time step t+4 at which an N+1-th frame image has been captured by the imaging device Cam1.

FIG. 4 is a diagram schematically showing a posture of a subject person Sub1 at a time step t at which an N-th frame image has been captured by an imaging device Cam1 (this time step is referred to as a time step t) and at a time step t+4 at which an N+1-th frame image has been captured by the imaging device Cam1 (this time step is referred to as a time step t+4).

Hereinafter, for convenience of explanation, the operation of the pose data generation system 1000 when the subject person Sub1 performs an action shown in FIG. 4 will be described. As shown in FIG. 4, it is assumed that the subject person Sub1 is in an upright posture (state) at the time step t at which the N-th frame image has been obtained, and moves the left hand is moved in the direction of the arrow Dir1 indicated FIG. 4 during a period from the time step t to the time step t+4. The operation of the pose data generation system 1000 in this case will be described below.

A three-dimensional coordinate system, in which the origin o, x-axis, y-axis, and z-axis are set, is set as shown in FIG. 4. The three-dimensional space defined by this three-dimensional coordinate system is set as the imaging space (the space to be imaged by the imaging device Cam1 (space SP1 in the case of FIG. 4)).

Figure 5:
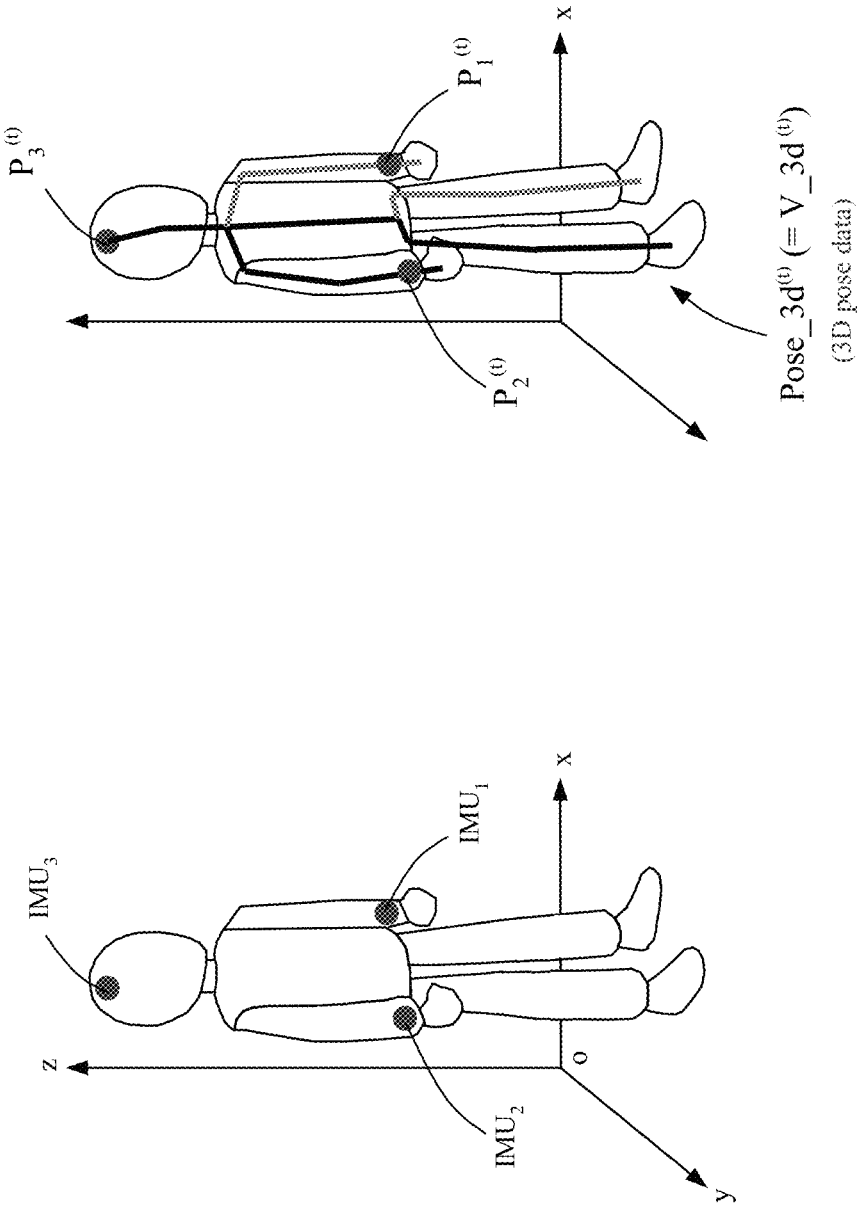
FIG. 5 is a diagram showing a position of an inertial measurement unit $IMU_k$ attached to the subject person Sub1.

FIG. 5 is a diagram showing the position of the inertial measurement unit $IMU_k$ attached to the subject person Sub1. For convenience of explanation, it is assumed that three inertial measurement units $IMU_1$ to $IMU_3$ are attached to the subject person Sub1, the inertial measurement unit $IMU_1$ is attached to the head of the subject person Sub1, and the inertial measurement unit $IMU_2$ is attached to right wrist portion of the subject person Sub1, and the inertial measurement unit $IMU_3$ is attached to left wrist portion of the subject person Sub1.

FIGS. 6 to 9 are diagrams for explaining pose data generation processing (including interpolation processing) performed by the pose data generation system 1000.

Figure 10:
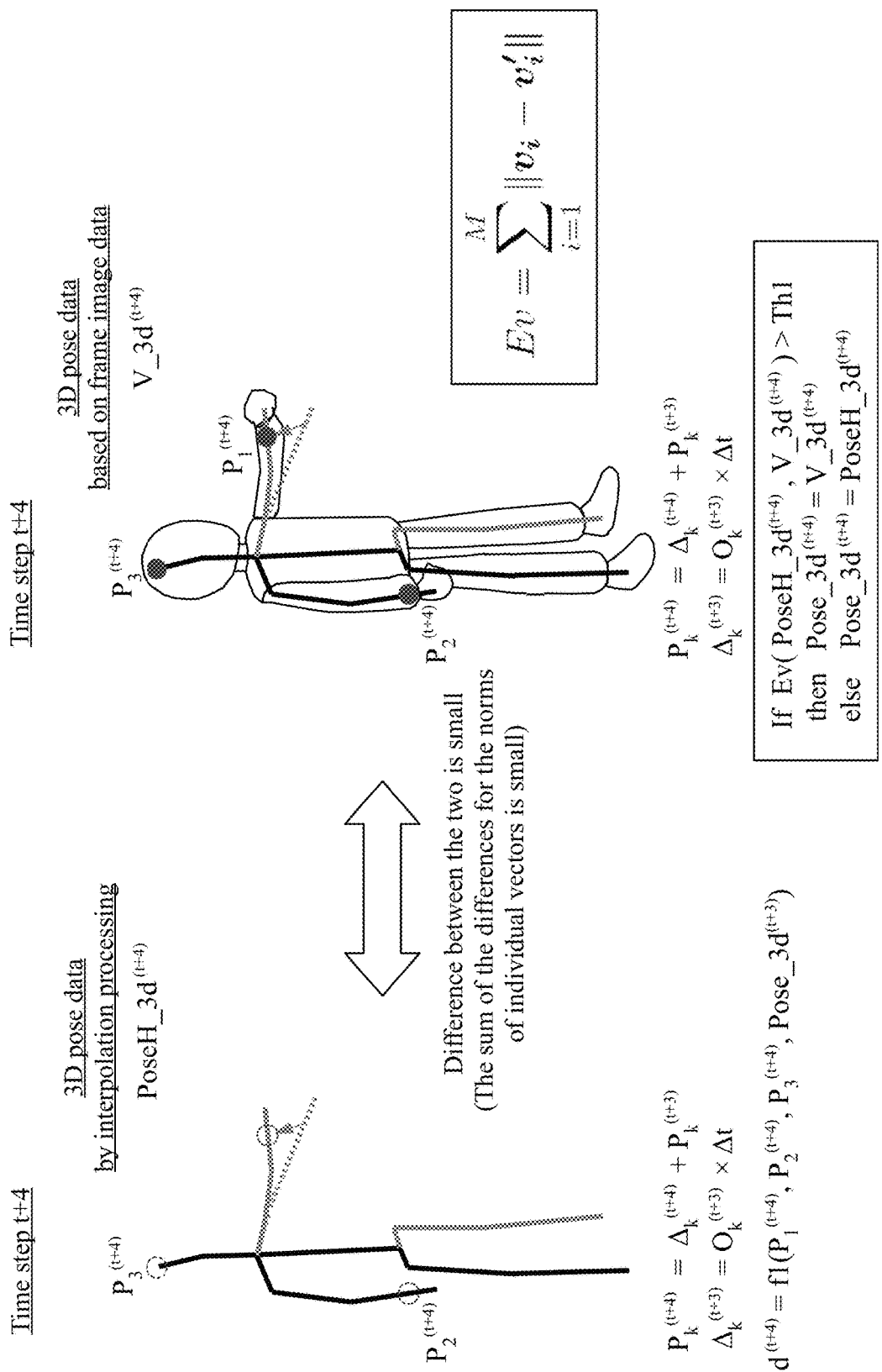
FIG. 10 is a diagram for explaining determination selection processing performed by the pose data generation system 1000.
Figure 11:
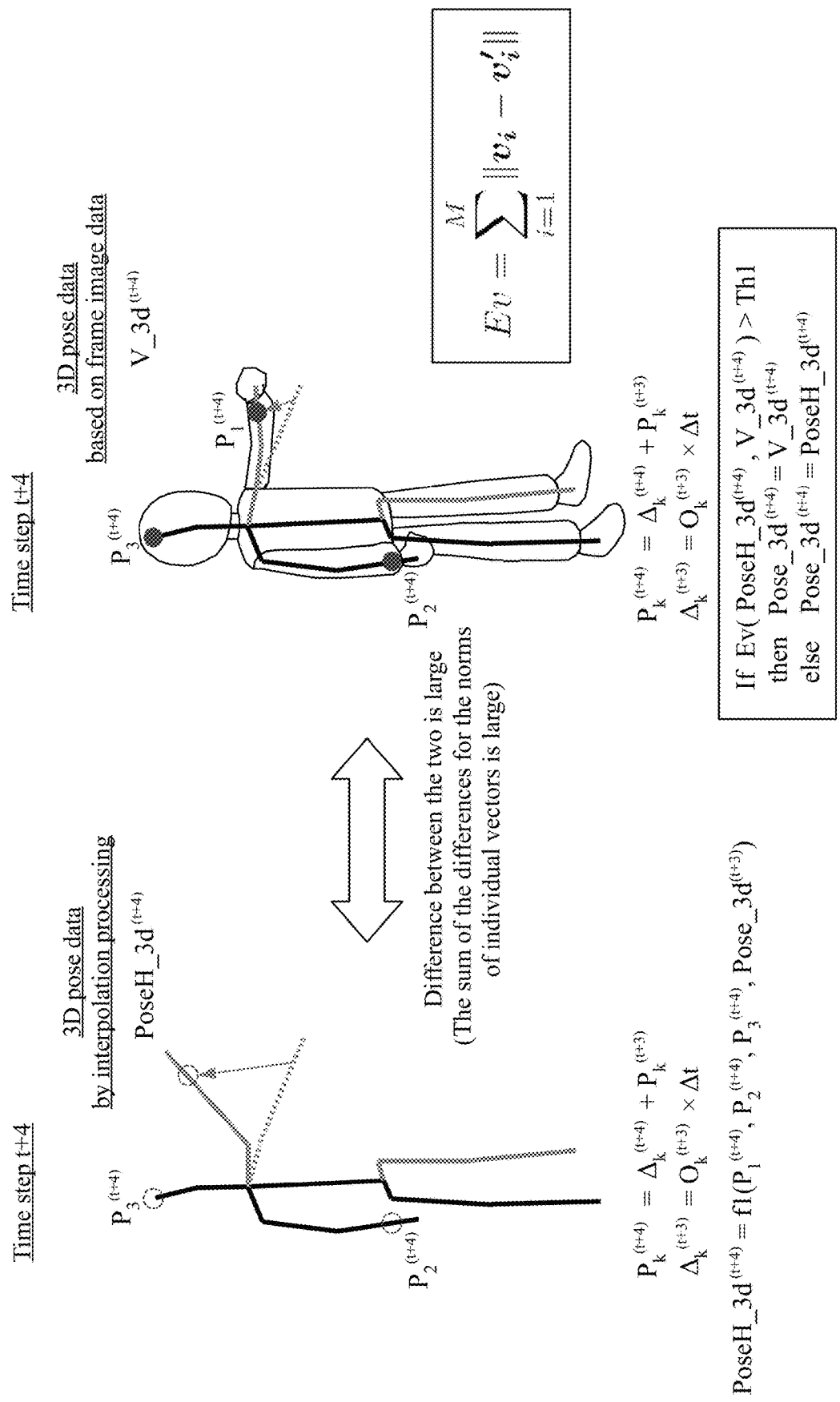
FIG. 11 is a diagram for explaining determination selection processing performed by the pose data generation system 1000.
Figure 12:
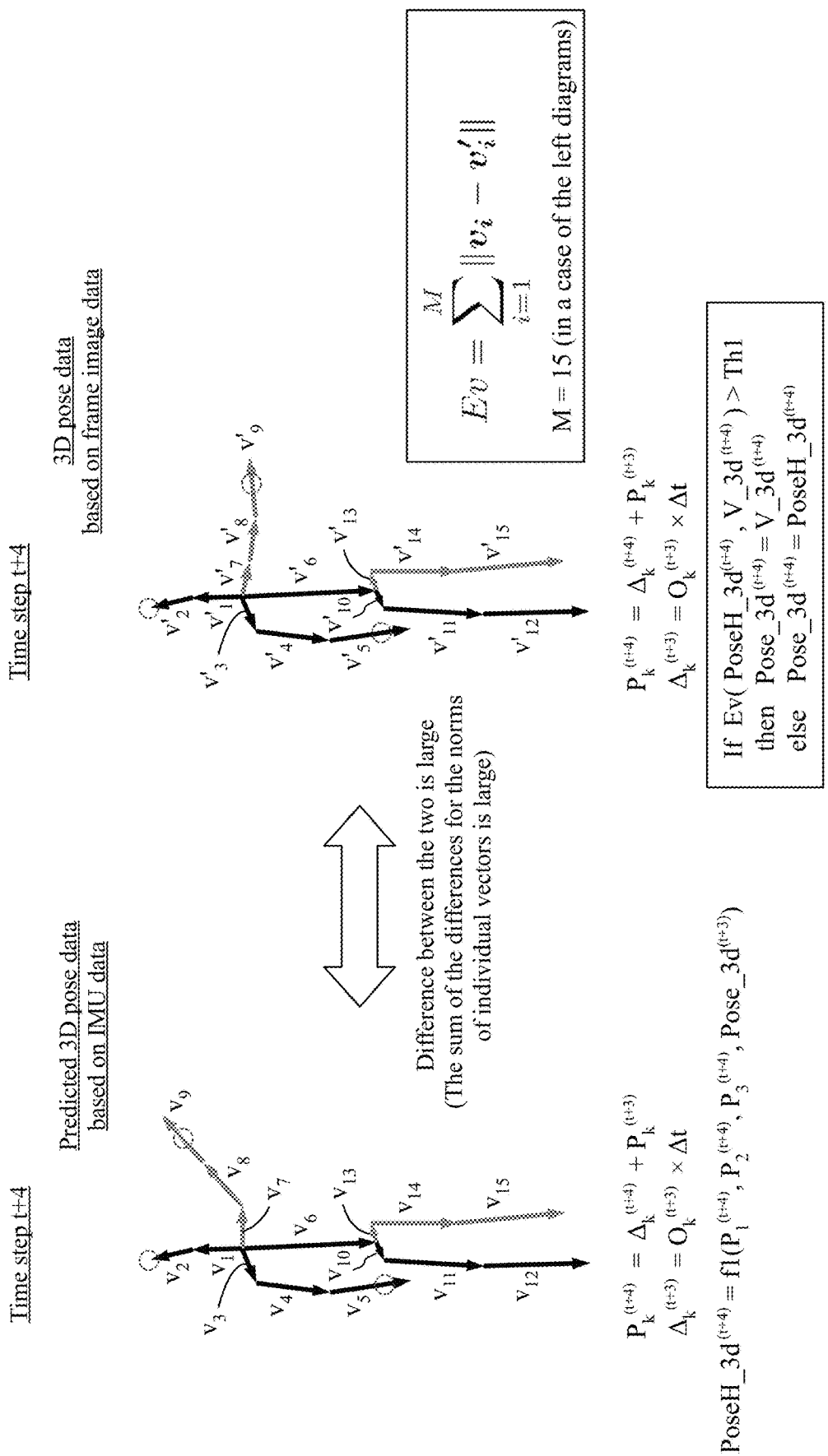
FIG. 12 is a diagram for explaining determination selection processing performed by the pose data generation system 1000.

FIGS. 10 to 12 are diagrams for explaining determination selection processing performed by the pose data generation system 1000.

Figure 13:
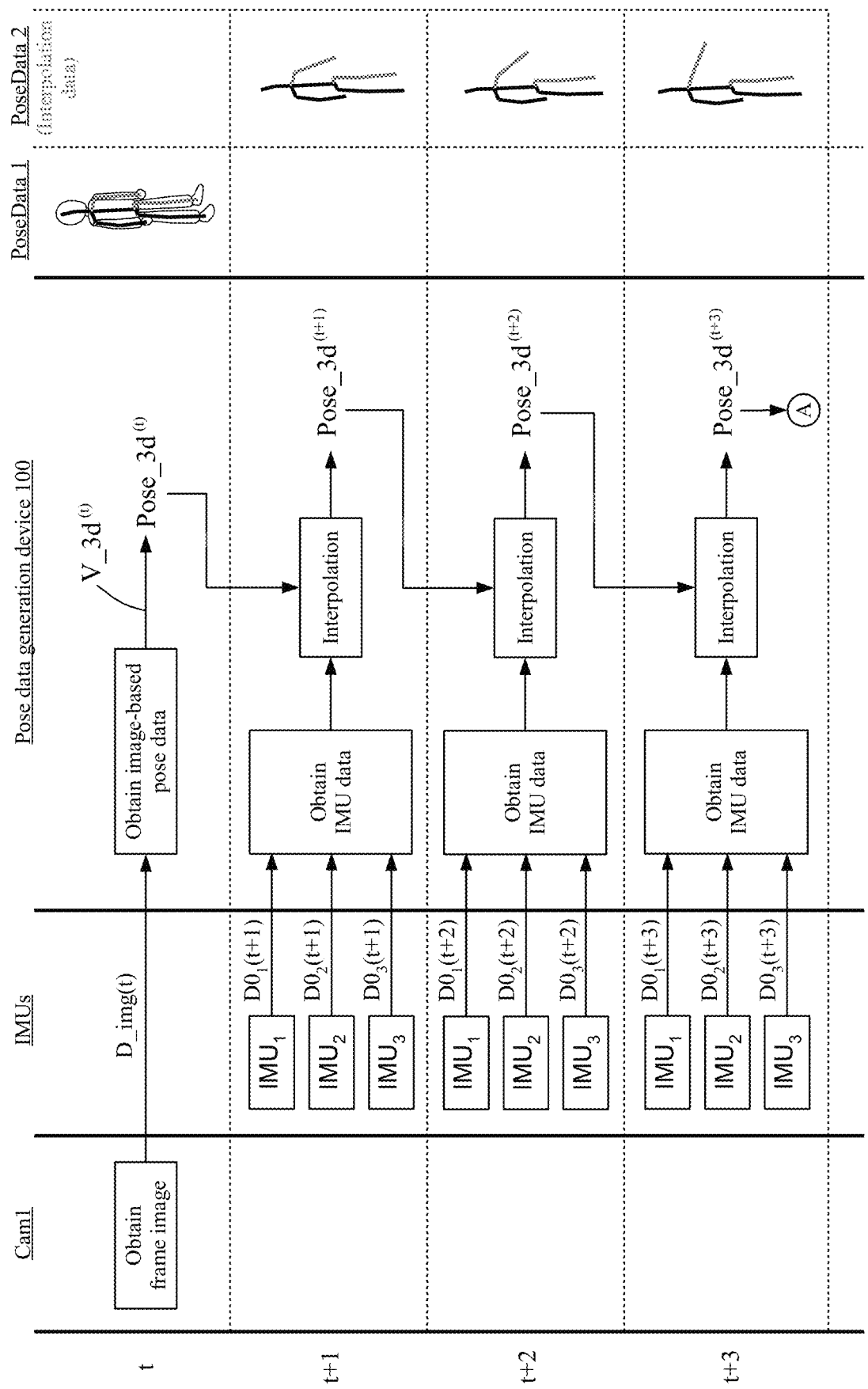
FIG. 13 is a sequence diagram of processing performed by the pose data generation system 1000.
Figure 14:
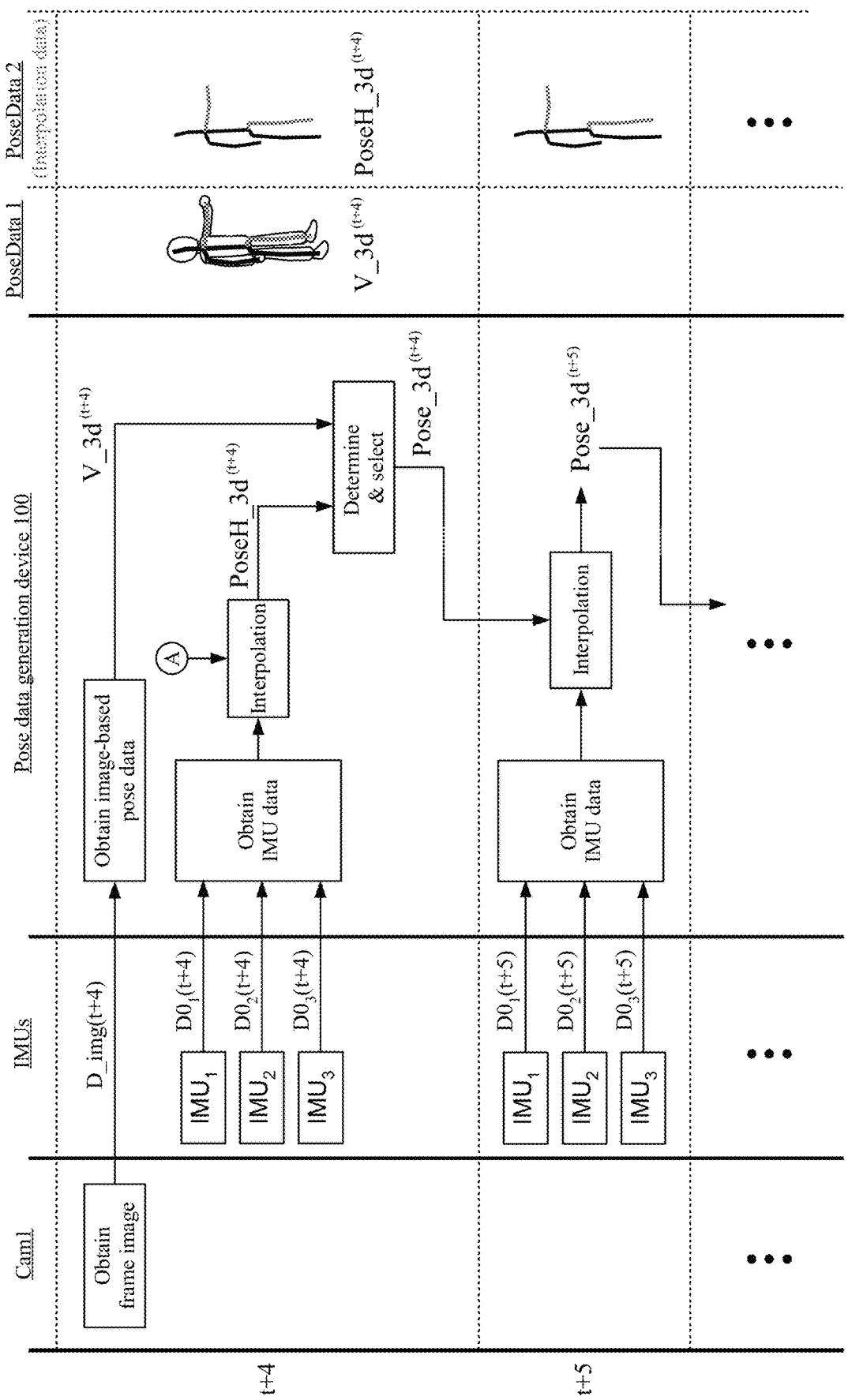
FIG. 14 is a sequence diagram of processing performed by the pose data generation system 1000.

FIGS. 13 to 14 are sequence diagrams of processing performed by the pose data generation system 1000. In FIGS. 13 and 14, the column shown by "PoseData1" shows pose data obtained from the frame image data, and the column shown by "PoseData2" shows the pose data obtained by the interpolation processing.

Hereinafter, the operation of the pose data generation system 1000 will be described with reference to the drawings.

Assuming that the imaging space is set in the three-dimensional space SP1 as shown in FIG. 4, the three-dimensional coordinate system (origin o, x-axis, y-axis, z-axis) is set as shown in FIG. 4, and the subject person Sub1 is a tracking target.

As an example, a case where frame images are obtained at four-time step intervals and three pieces of pose data are generated by interpolation processing during a period in which the frame images has not been obtained in the pose data generation system 1000 will be described below.

<<Processing of Time Step t>>

At the time step t, the frame image data D_img(t) is obtained by taking an image of the three-dimensional space (imaging space SP1) including the subject person Sub1 by the imaging device Cam1. Note that frame image data obtained at the time step t is referred to as D_img(t). The image (frame image) formed by the frame image data D_img(t) is an image Img1 shown in the upper left figure of FIG. 2.

The image-based pose data obtaining unit 1 receives the frame image data D_img(t) transmitted from the imaging Cam1, and performs processing for obtaining the three-dimensional pose data (three-dimensional image-based pose data) from the frame image data D_img(t). Specifically, the following processing is performed.

The 2D key point data obtaining unit 11 of the image-based pose data obtaining unit 1 (1) extracts an image region corresponding to the subject person Sub1 in the frame image (image Img1) formed by frame image data D_img(t), and (2) determines positions (positions in the two-dimensional image) of predetermined portions of the subject person Sub1 in the frame image based on the information Info_space of the imaging space inputted into the image-based pose data obtaining unit 1 and the information Info_cam_prm of the imaging parameters of the imaging device Cam1. Here, the "predetermined portions" are (1) predetermined positions included in included in the head and spine of a person (corresponding to the key points $kp_1$ to $kp_4$ in FIG. 3), (2) predetermined positions included in the left and right arms of the person (corresponding to key points $kp_5$ to $kp_7$ and $kp_{14}$ to $kp_{16}$ in FIGS. 3), and (3) predetermined positions included in the left and right legs of the person (corresponding to key points $kp_8$ to $kp_{10}$ and $kp_{11}$ to $kp_{13}$ in FIG. 3. The key points determined by the key point data D_2d_key_points correspond to 16 points $kp_1$ to $kp_{16}$ as shown in FIG. 3.

In the pose data generation system 1000, the tracking target is a person (the standard human size is known), and the installation position in the three-dimensional space, the direction of the camera optical axis, the focal length, and the angle of view of the imaging device Cam1 are known; thus, the pose data generation system 1000 can extract an image region corresponding to the subject person Sub1 from the frame image obtained by the imaging device Cam1, and can determine the positions of specific portions of the subject person Sub1 in the frame image.

The 2D key point data obtaining unit 11 then transmits the key point data obtained by the above processing to the 3D pose data obtaining unit 12 as data D_2d_key_points.

The 3D pose data obtaining unit 12 obtains three-dimensional pose data from the key point data D_2d_key_points based on the information Info_space of the imaging space inputted into the image-based pose data obtaining unit 1 and the information Info_cam_prm of the imaging parameters of the imaging device Cam1. Specifically, the 3D pose data obtaining unit 12 estimates the positions (coordinate positions) in the coordinate system of the space SP1, which correspond to points in the frame image (two-dimensional image) indicated by the key point data D_2d_key_points (two-dimensional coordinate data), and then obtains the three-dimensional coordinate information of the estimated positions.

In the pose data generation system 1000, the tracking target is a person (the standard human size is known), the installation position in the three-dimensional space, the direction of the camera optical axis, the focal length, and the angle of view of the imaging device Cam1 are known, and furthermore the information for specifying the three-dimensional space SP1 that has been set as the imaging space is known; thus, from the positions in the frame image (the coordinate positions in the imaging space SP1) of the specific portions of the subject person Sub1, the pose data generation system 1000 can estimate the coordinate positions of the specific portions of the subject person Sub1. In other words, the pose data generation system 1000 can estimate the coordinate information (three-dimensional coordinate data) in the three-dimensional space SP1 of each key point from the key point data D_2d_key_points (two-dimensional coordinate data of each key point in the two-dimensional image).

Note that the processing (estimation processing) for estimating the coordinate information (three-dimensional coordinate data) in the three-dimensional space SP1 of each key point from the key point data D_2d_key_points (two-dimensional coordinate data of each key point in the two-dimensional image) may use calculation processing for converting the two-dimensional coordinate space into the three-dimensional coordinate space, or may use processing with a neural network. When processing by the neural network as the above estimation processing is used, for example, the processing is performed as follows. In such processing, the key point data of the person obtained from the two-dimensional image (frame image) of the person is set to input data, the coordinate data (three-dimensional coordinate data) in the three-dimensional space of each key point of the key point data is set to supervised data for output data, and then the training process of a neural network model is performed. Performing the training process obtains a trained model that inputs the key point data of the person obtained from the two-dimensional image (frame image) of the person and outputs prediction data of the coordinate data (three-dimensional coordinate data) in the three-dimensional space of each key point of the key point data. Performing processing using the trained model allows for achieving estimation processing for estimating coordinate information (three-dimensional coordinate data) in the three-dimensional space SP1 of each key point from the key point data D_2d_key_points (two-dimensional coordinate data of each key point in the 2D image).

The 3D pose data obtaining unit 12 transmits data including the coordinate data (three-dimensional coordinate data) in the three-dimensional space of each key point obtained by the above processing, as data D1_pose_3D (data D1_pose_3D obtained at the time step t is referred to as D1_pose_3D(t)), to the interpolation unit 3.

As shown in the upper right figure of FIG. 2, data D1_pose_3D (3D pose data) is shown as a diagram in which points specified by the coordinate data (three-dimensional coordinate data) in the three-dimensional space of individual key points are connected by lines. Further, 3D pose data D1_pose_3D obtained by the image-based pose data obtaining unit 1 at the time step t is referred to as V_3d$^{(t)}$.

Figure 6:
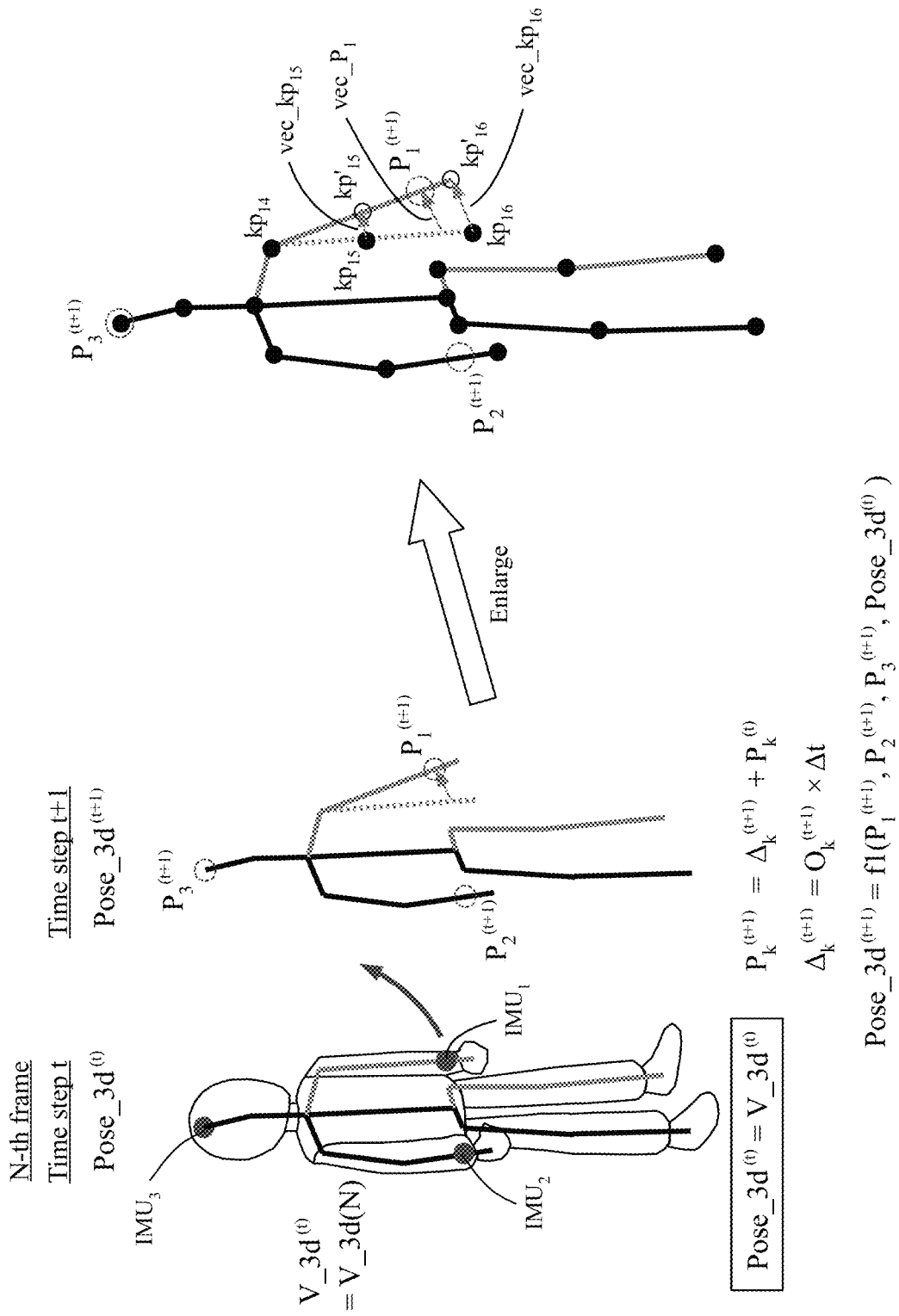
FIG. 6 is a diagram for explaining pose data generation processing (including interpolation processing) performed by the pose data generation system 1000.

At the time step t, the interpolation unit 3 receives the data D1_pose_3D (=V_3d$^{(t)}$) transmitted from the image-based pose data obtaining unit 1, and transmits the received data, as it is, as the output data Dout (see the diagram at the time step t in FIG. 6, and processing at the time step t in FIG. 13). The interpolation unit 3 stores and holds the output data Dout as the 3D pose data Pose_3d$^{(t)}$ (=V_3d$^{(t)}$) at the time step t. Note that the data outputted from the interpolation unit 3 at the time step t is referred to as data Pose_3d$^{(t)}$.

Further, using the 3D pose data Pose 3d(t), the interpolation unit 3 determines (estimates) the position (coordinate position) of the inertial measurement unit $IMU_k$ (k is a natural number satisfying 1≤k≤3) in the three-dimensional space SP1 at the time step t. Since the mounting position of the inertial measurement unit $IMU_k$ is known, the interpolation unit 3 determines (estimates) the position in the three-dimensional space SP1 corresponding to the mounting position of the inertial measurement unit $IMU_k$ based on the 3D pose data Pose_3d(t). For example, the inertial measurement unit $IMU_1$ is attached to the left list portion of the subject person Sub1 as shown in the right figure of FIG. 5; thus, referring to the 3D pose data Pose_3d$^{(t)}$, the position (coordinate position in the three-dimensional space SP1) (the position indicated by $P_1{}^{(t)}$ in the right figure of FIG. 5) corresponding to the left list of the subject person Sub1 is determined. Thus, the interpolation unit 3 specifies the data of the coordinate position in the three-dimensional space SP1 at this position as $P_1$(0, and stores and holds the data.

Note that $P_1{}^{(t)}$ is as follows:

$$P_1^T(t) = [x_1^{(t)}, y_1^{(t)}, z_1^{(t)}]$$

$x_1^{(t)}$: x-coordinate of the inertial measurement unit $IMU_1$ at the time step t $y_1^{(t)}$: y-coordinate of the inertial measurement unit $IMU_1$ at the time step t $z_1^{(t)}$ z-coordinate of the inertial measurement unit $IMU_1$ at the time step t $P^T{}_1{}^{(t)}$: transposed matrix of $P_1{}^{(t)}$ Similarly, the inertial measurement unit $IMU_2$ is attached to the right list portion of the subject person Sub1; thus, referring to the 3D pose data Pose_3d$^{(t)}$, the position (coordinate position in the three-dimensional space SP1) (the position indicated by $P_2{}^{(t)}$ in the right figure of FIG. 5) corresponding to the right list portion of the subject person Sub1 is determined. Thus, the interpolation unit 3 specifies the data of the coordinate position in the three-dimensional space SP1 at this position as $P_2$(t), and stores and holds the data. Note that $P_2$(0 is as follows:

$$P_2^{T(t)} = [x_2^{(t)}, y_2^{(t)}, z_2^{(t)}]^T$$

$x_2^{(t)}$: x-coordinate of the inertial measurement unit $IMU_2$ at the time step t $Y_2^{(t)}$: y-coordinate of the inertial measurement unit $IMU_2$ at the time step t $z_2^{(t)}$: z-coordinate of the inertial measurement unit $IMU_2$ at the time step t $P^T{}_2{}^{(t)}$: transposed matrix of $P_2{}^{(t)}$ Similarly, the inertial measurement unit $IMU_3$ is attached to the head of the subject person Sub1; thus, referring to the 3D pose data Pose_3d$^{(t)}$, the position (coordinate position in the three-dimensional space SP1) (the position indicated by P$_3$(t) in the right figure of FIG. 5) corresponding to the head of the subject person Sub1 is determined. Thus, the interpolation unit 3 specifies the data of the coordinate position in the three-dimensional space SP1 at this position as P$_3$(t), and stores and holds the data. Note that P$_3$(t) is as follows:

$$P_3^{T(t)} = \left[x_3^{(t)}, y_3^{(t)}, z_3^{(t)}\right]''$$

X$_3^{(t)}$: x-coordinate of the inertial measurement unit IMU$_3$ at the time step t y$_3^{(t)}$: y-coordinate of the inertial measurement unit IMU$_3$ at the time step t z$_3^{(t)}$: z-coordinate of the inertial measurement unit IMU$_3$ at the time step t P$^T{}_3^{(t)}$: transposed matrix of P$_3{}^t$)

<<Processing at Time Step t+1>>

At the time step t+1, the inertial measurement units IMU$_1$ to IMU$_3$ obtain IMU data D0$_1$(t+1) to D0$_3$(t+1), respectively, and transmit the obtained IMU data to the IMU data obtaining unit 2 of the pose data generation device 100. Note that a case where inertial measurement units IMU$_1$ to IMU$_3$ are assumed to obtain angular velocity data will be described below. Further, IMU data obtained by the inertial measurement unit IMU$_1$ at the time step t is referred to as D0$_k$(t).

The IMU data obtaining unit 2 receives data D0$_1$(t+1) to D0$_3$(t+1) transmitted from the inertial measurement units IMU$_1$ to IMU$_3$, respectively. The IMU data obtaining unit 2 obtains the received data, in which D0$_1$ to D0$_1$ are integrated, as data D1_imu (data D1 imu obtained at the time step t+1 is referred to as D1_imu(t+1)), and then transmits the obtained data D1 imu (=D1_imu(t+1)) to the interpolation unit 3.

The interpolation unit 3 obtains the three-dimensional coordinate position data P$_1^{(t+1)}$ to P$_3^{(t+1)}$ of the inertial measurement units IMU$_1$ to IMU$_3$ at the time step t+1 using (1) the IMU data D0$_1$(t+1) to D0$_3$(t+1) obtained at the time step t+1 and (2) the three-dimensional coordinate position data P$_1^{(t)}$ to P$_3^{(t)}$ of the inertial measurement units IMU$_1$ to IMU$_3$ at the time step t, which has been stored and held in the interpolation unit 3. Specifically, the interpolation unit 3 performs the process corresponding to the following formula to obtain the three-dimensional coordinate position data P$_1^{(t+1)}$ to P$_3^{(t+1)}$ of the inertial measurement units IMU$_1$ to IMU$_3$ at the time step t+1.

$$P_k^{(t+1)} = \Delta_k^{(t+1)} + P_k^{(t)} \quad \text{Formula 1}$$

$$P_k^{(t+1)} = \begin{pmatrix} x_k^{(t+1)} \\ y_k^{(t+1)} \\ z_k^{(t+1)} \end{pmatrix}$$

$$\Delta_k^{(t+1)} = \begin{pmatrix} \Delta x_k^{(t+1)} \\ \Delta y_k^{(t+1)} \\ \Delta z_k^{(t+1)} \end{pmatrix}$$

$$P_k^{(t)} = \begin{pmatrix} x_k^{(t)} \\ y_k^{(t)} \\ z_k^{(t)} \end{pmatrix}$$

k: natural number satisfying 1≤k≤3

$$\Delta_k^{(t+1)} = O_k^{(t+1)} \times \Delta t$$

$$O_k^{T(t+1)} = \left[\omega x_k^{(t+1)}, \omega y_k^{(t+1)}, \omega z_k^{(t+1)}\right]$$

Δt: time interval between the time step t and the time step t+1

O$^T{}_k^{(t+1)}$: transposed matrix of O$_k^{(t+1)}$

Note that ωX$_k^{(t+1)}$ is the x component data of the angular velocity obtained by the inertial measurement unit IMU$_k$ at the time step t+1, ωy$_k^{(t+1)}$ is the y component of the angular velocity obtained by the inertial measurement unit IMU$_k$ at the time step t+1, and ωz$_k^{(t+1)}$ is the z component of the angular velocity obtained by the inertial measurement unit IMU$_k$ at the time step t+1.

The interpolation unit 3 multiplies each component of the angular velocity obtained by the inertial measurement unit IMU$_k$ at the time step t+1 by the elapsed time At from the time step t to the time step t+1, thereby obtaining (estimating) the displacement amount for each component (x, y, and z components). In other words, the interpolation unit 3 performs processing corresponding to the following formulas to obtain (estimate) the displacement amount (movement amount) from the time step t to the time step t+1.

$$\Delta x_k^{(t+1)} = \omega x_k^{(t+1)} \times \Delta t$$
$$\Delta y_k^{(t+1)} = \omega y_k^{(t+1)} \times \Delta t$$
$$\Delta z_k^{(t+1)} = \omega z_k^{(t+1)} \times \Delta t$$

The interpolation unit 3 then performs interpolation processing using (1) the 3D pose data Pose_3d$^{(t)}$ (=V_3d$^{(t)}$) at the time step t and (2) the three-dimensional coordinate position data P$^{(t+1)}$ to P$_3^{(t+1)}$ of the inertial measuring devices IMU$_1$ to IMU$_3$ at the time step t+1 obtained as described above, thereby obtaining the 3D pose data Pose_3d$^{(t+1)}$ at the time step t+1.

Specifically, the interpolation unit 3 performs processing corresponding to the following formula to obtain the 3D pose data Pose_3d$^{(t+1)}$ at the time step t+1.

$$\text{Pose\_3}d^{(t+1)} = f1\left(P_1^{(t+1)}, P_2^{(t+1)}, P_3^{(t+1)}, \text{Pose\_3}d^{(t)}\right)$$

Note that the function f1 is a function for obtaining the 3D pose data Pose_3d$^{(t+1)}$ at the time step t+1 from P$_1^{(t+1)}$ to P$_3^{(t+1)}$ and Pose_3d$^{(t)}$.

Specifically, when the position of the inertial measurement unit IMU$_k$ is assumed to be the above estimated position at the time step t+1, the interpolation unit 3 predicts how each key point will move considering the degree of freedom of human joints and the movable range of each portion. For example, as shown in the right figure of FIG. 6 (enlarged view of the figure at time step t+1), it is estimated that the position of the inertial measurement unit IMU$_1$ has moved from P$_1^{(t)}$ to P$_1^{(t+1)}$ (the vector from P$_1^{(t)}$ to P$_1^{(t+1)}$ is referred to as vec_P$_1$), and thus the interpolation unit 3, considering the vector vec_P$_1$, estimates that a movement vector for the key point kp$_{15}$ (key point data specified from Pose_3d(O) at the time step t+1 is the vector vec_kp$_{15}$ (the vector vec_kp$_{15}$ in FIG. 6) and the position at the time step t+1 of the key point $kp_{15}$ is the position $kp'_{15}$ shown in FIG. 6. Similarly, the interpolation unit 3, considering the vector $vecz\_P_1$, estimates that a movement vector for the key point $kp_{16}$ (key point data specified from Pose_3d(O) at the time step t+1 is the vector $vec\_kp_{16}$ (the vector $vec\_kp_{16}$ in FIG. 6) and the position at the time step t+1 of the key point $kp_{16}$ is the position $kp'_{16}$ shown in FIG. 6.

Since the positions of the inertial measurement units $IMU_2$ and $IMU_3$ have not changed, it is estimated that the positions of the key points $kp_1$ to $kp_{14}$ (key point data specified from Pose_3d$^{(t)}$ has not changed in the period from the time step t to the time step t+1.

Based on the three-dimensional coordinate data of the key points obtained by the above processing (estimation (corresponding to the processing by using the function f1)), the interpolation unit 3 obtains the 3D pose data Pose_3d$^{(t+1)}$ (the 3D pose data Pose_3d$^{(t+1)}$ shown in FIG. 6) at the time step t+1.

The interpolation unit 3 then transmits the 3D pose data Pose_3d$^{(t+1)}$ obtained by the above processing (processing at the time step t+1 in the sequence diagram of FIG. 13) and stores the data.

Further, the interpolation unit 3 stores and holds the three-dimensional coordinate position data $P_1^{(t+1)}$ to $P_3$(t+1) of the inertial measurement units $IMU_1$ to $IMU_3$ at the time step t+1.

<<Processing of Time Step t+2>>

At the time step t+2, the inertial measurement units $IMU_1$ to $IMU_3$ obtain IMU data $D0_1$(t+2) to $D0_3$(t+2), respectively, and transmit the obtained IMU data to the IMU data obtaining unit 2 of the pose data generation device 100.

The IMU data obtaining unit 2 receives data $D0_1$(t+2) to $D0_3$(t+2) transmitted from the inertial measurement units $IMU_1$ to $IMU_3$, respectively. The IMU data obtaining unit 2 obtains the received data, in which $D0_1$ to $D0_1$ are integrated, as data D1_imu(t+2), and transmits the obtained data D1_imu(t+2) to the interpolation unit 3.

The interpolating unit 3 obtains the three-dimensional coordinate position data $P_1^{(t+2)}$ to $P_3^{(t+2)}$ of the inertial measurement units $IMU_1$ to $IMU_3$ at the time step t+2 using (1) the IMU data $D0_1$(t+2) to $D0_3$(t+2) obtained at the time step t+2 and (2) the three-dimensional coordinate position data $P_1^{(t+1)}$ to $P_3$(t+1) of the inertial measurement units $IMU_1$ to $IMU_3$ at the time step t+1, which has been stored in the interpolation unit 3.

Specifically, the interpolation unit 3 performs the same processing as the processing at the time step t+1 to obtain the three-dimensional coordinate position data $P_1^{(t+2)}$ to $P_3^{(t+2)}$ of the inertial measurement units $IMU_1$ to $IMU_3$ at the time step t+2.

Th interpolation unit 3 then performs processing corresponding to the following formula in the same manner as at the time step t+1 to obtain the 3D pose data Pose_3d$^{(t+2)}$ at the time step t+2.

$$\text{Pose\_3}d^{(t+2)} = f1(P_1^{(t+2)}, P_2^{(t+2)}, P_3^{(t+2)}, \text{Pose\_3}d^{(t+1)})$$

Figure 7:
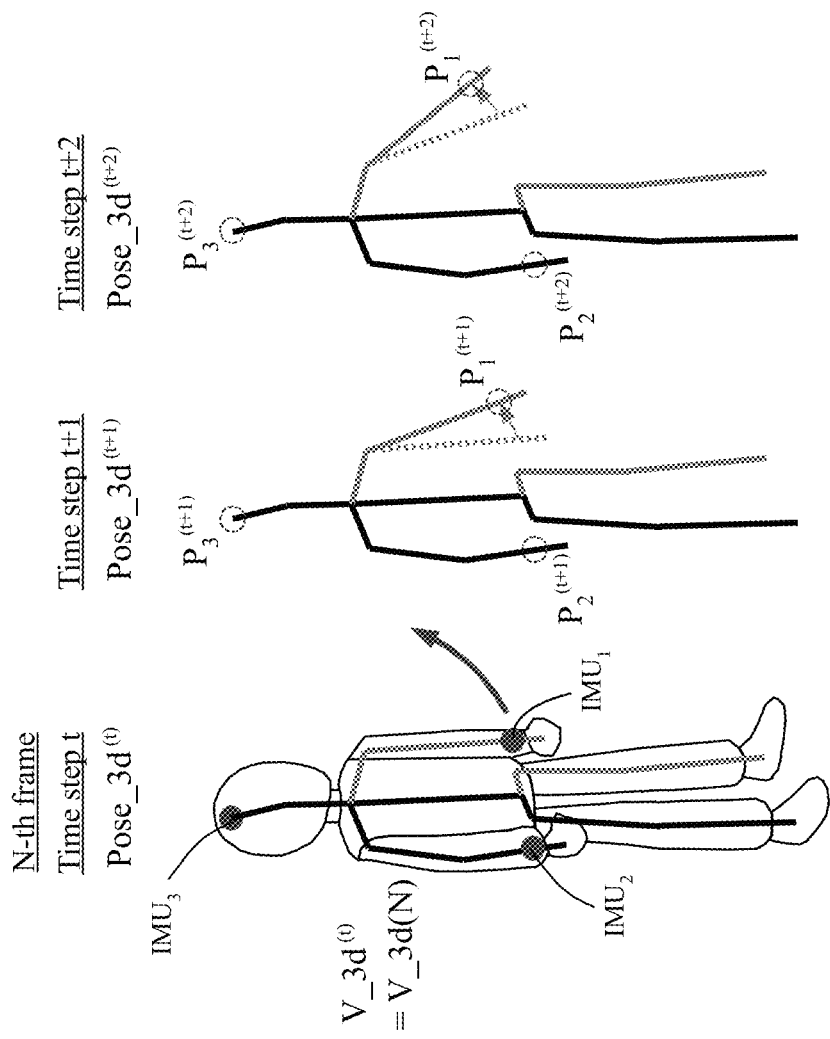
FIG. 7 is a diagram for explaining pose data generation processing (including interpolation processing) performed by the pose data generation system 1000.

As a result, the interpolation unit 3 obtains the 3D pose data Pose_3d$^{(t+2)}$ at the time step t+2 as shown in FIG. 7.

The interpolation unit 3 then transmits the 3D pose data Pose_3d$^{(t+2)}$ obtained by the above processing (processing at the time step t+2 in the sequence diagram of FIG. 13) and stores the data.

Further, the interpolation unit 3 stores and holds the three-dimensional coordinate position data $P_1^{(t+2)}$ to $P_3^{(t+2)}$ of the inertial measurement units $IMU_1$ to $IMU_3$ at the time step t+2.

<<Processing at Time Step t+3>>

At the time step t+3, the inertial measurement units $IMU_1$ to $IMU_3$ obtain IMU data $D0_1$(t+3) to $D0_3$(t+3), respectively, and transmit the obtained IMU data to the IMU data obtaining unit 2 of the pose data generation device 100.

The IMU data obtaining unit 2 receives data $D0_1$(t+3) to $D0_3$(t+3) transmitted from the inertial measurement units $IMU_1$ to $IMU_3$, respectively. The IMU data obtaining unit 2 obtains the received data, in which $D0_1$ to $D0_1$ are integrated, as data D1_imu (t+3), and transmits the obtained data D1 imu(t+3) to the interpolation unit 3.

The interpolation unit 3 obtains the three-dimensional coordinate position data $P_1^{(t+3)}$ to $P_3^{(t+3)}$ of the inertial measurement units $IMU_1$ to $IMU_3$ at the time step t+3 using (1) the IMU data $D0_1$(t+3) to $D0_3^{(t+3)}$ obtained at the time step t+3 and (2) the three-dimensional coordinate position data $P_1$(t+2) to $P_3^{(t+2)}$ of the inertial measurement units $IMU_1$ to $IMU_3$ at the time step t+2, which has been stored and held in the interpolation unit 3.

Specifically, the interpolation unit 3 performs the same processing as the processing at the time step t+1 to obtain the three-dimensional coordinate position data $P_1^{(t+3)}$ to $P_3^{(t+3)}$ of the inertial measurement units $IMU_1$ to $IMU_3$ at the time step t+3.

Th interpolation unit 3 then performs processing corresponding to the following formula in the same manner as at the time step t+1 to obtain the 3D pose data Pose_3d$^{(t+1)}$ at the time step t+3.

$$\text{Pose\_3}d^{(t+3)} = f1(P_1^{(t+3)}, P_2^{(t+3)}, P_3^{(t+3)}, \text{Pose\_3}d^{(t+2)})$$

Figure 8:
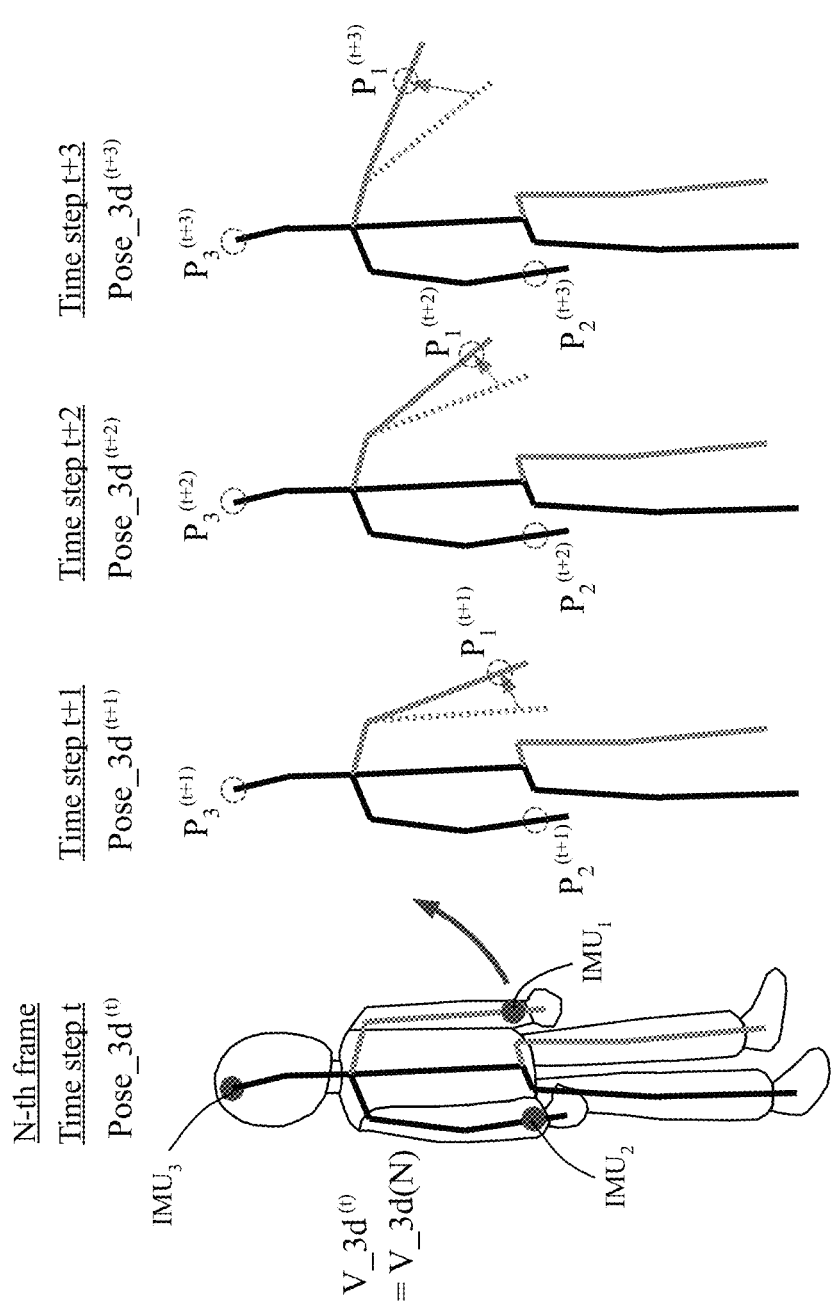
FIG. 8 is a diagram for explaining pose data generation processing (including interpolation processing) performed by the pose data generation system 1000.
Figure 9:
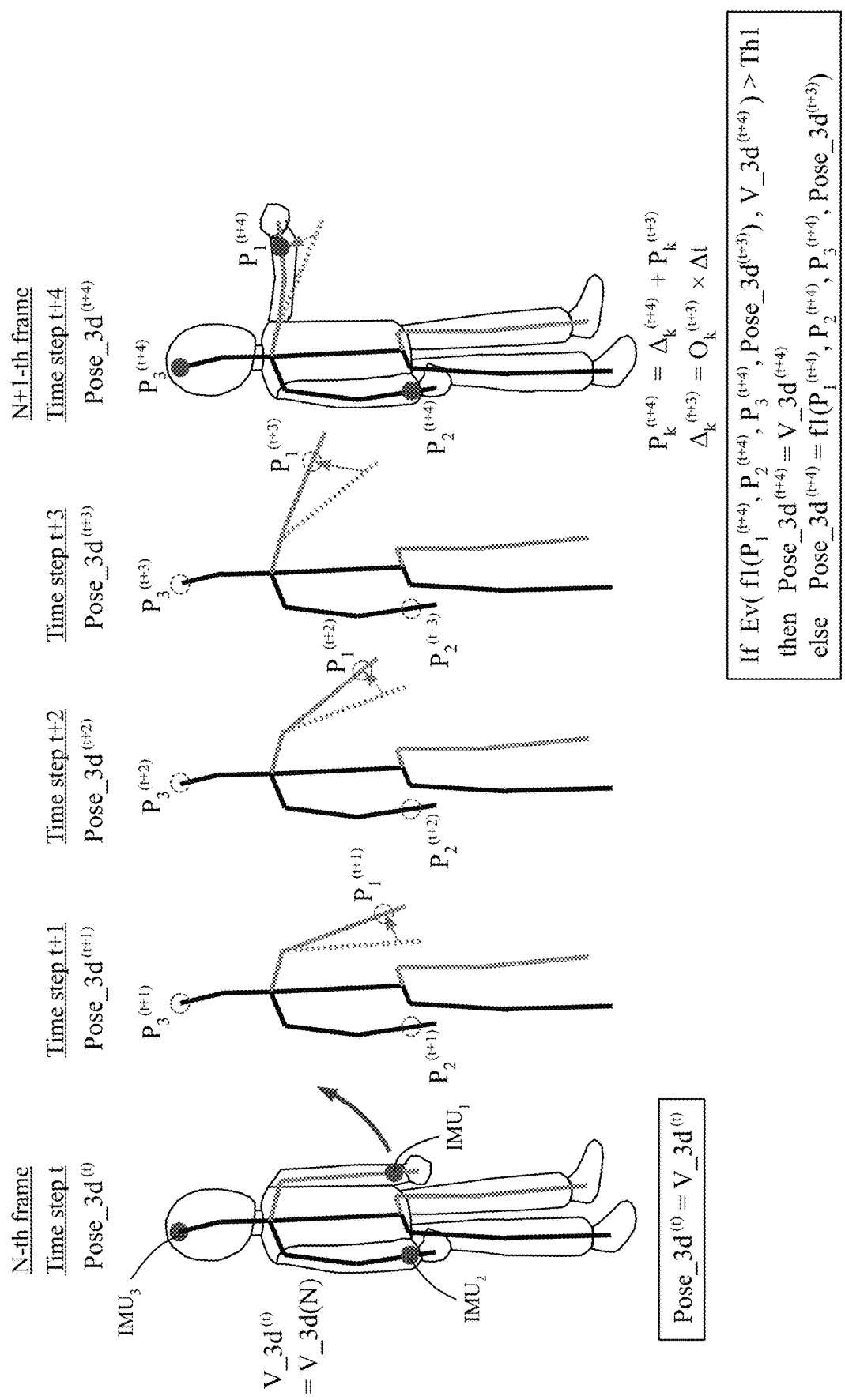
FIG. 9 is a diagram for explaining pose data generation processing (including interpolation processing) performed by the pose data generation system 1000.

As a result, the interpolation unit 3 obtains the 3D pose data Pose_3d$^{(t+3)}$ at the time step t+3 as shown in FIG. 8.

The interpolation unit 3 then transmits the 3D pose data Pose_3d$^{(t+3)}$ obtained by the above processing (processing at the time step t+3 in the sequence diagram of FIG. 13) and stores the data.

Further, the interpolation unit 3 stores and holds the three-dimensional coordinate position data $P_1^{(t+3)}$ to $P_3^{(t+3)}$ of the inertial measurement units $IMU_1$ to $IMU_3$ at the time step t+3.

<<Processing at Time Step t+4>>

At the time step t+4, the frame image data D_img(t) is obtained by taking an image of the three-dimensional space (imaging space SP1) including the subject person Sub1 by the imaging device Cam1.

The image-based pose data obtaining unit 1 performs the same processing as that in the time step t to obtain the three-dimensional pose data D1_pose_3D(t+4) (=V_3d$^{(t+4)}$ from the frame image data D_img(t+4) transmitted from the imaging device Cam1.

The interpolation unit 3 specifies (estimates) the position (coordinate position) of the inertial measurement unit $IMU_k$ (k is a natural number satisfying 1≤k≤3) in the three-dimensional space SP1 at the time step t using the 3D pose data V_3d$^{(t+4)}$ in the same manner as at the time step t. As a result, the interpolation unit 3 obtains the three-dimensional coordinate data $P_1^{(t+4)}$ to $P_3^{(t+4)}$ of the inertial measurement units $IMU_1$ to $IMU_3$.

Further, the interpolation unit 3 performs the same interpolation processing as at the time step t+1. In other words, the interpolation unit 3 performs the following processing.

At the time step t+4, the inertial measurement units $IMU_1$ to $IMU_3$ obtain IMU data $D0_1(t+4)$ to $D0_3(t+4)$, respectively, and transmit the obtained IMU data to the IMU data obtaining unit 2 of the pose data generation device 100.

The IMU data obtaining unit 2 receives data $D0_1(t+4)$ to $D0_3(t+4)$ transmitted from the inertial measurement units $IMU_1$ to $IMU_3$, respectively. The IMU data obtaining unit 2 obtains the received data, in which $D0_1$ to $D0_1$ are integrated, as data $D1\_imu(t+4)$, and then transmits the obtained data $D1\_imu(t+4)$ to the interpolation unit 3.

The interpolation unit 3 obtains the three-dimensional coordinate position data $P_1(t+4)$ to $P_3(t*4)$ of the inertial measurement units $IMU_1$ to $IMU_3$ at the time step t+4 using (1) the IMU data $D0_1(t+4)$ to $D0_3(t+4)$ obtained at the time step t+4 and (2) the three-dimensional coordinate position data $P_1^{(t+3)}$ to $P_3^{(t+3)}$ of the inertial measurement units $IMU_1$ to $IMU_3$ at the time step t+3, which has been stored and held in the interpolation unit 3.

Specifically, the interpolation unit 3 performs the same processing as the processing at the time step t+1 to obtain the three-dimensional coordinate position data $P_1^{(t+4)}$ to $P_3^{(t+4)}$ of the inertial measurement units $IMU_1$ to $IMU_3$ at the time step t+4.

Th interpolation unit 3 then performs the same processing as at the time step t+1 to obtain the 3D pose data (3D pose data obtained by interpolation processing). Note that the 3D pose data obtained by the interpolation unit 3 in the interpolation processing at the time step t+4 is referred to as 3D pose data $Pose\_3dH^{(t+4)}$. In other words, the interpolation unit 3 performs processing corresponding to the following formula to obtain the 3D pose data $PoseH\_3d^{(t+4)}$ obtained by the interpolation processing at the time step t+4.

$$PoseH\_3d^{(t+4)} = f1\left(P_1^{(t+4)}, P_2^{(t+4)}, P_3^{(t+4)}, Pose\_3d^{(t+3)}\right)$$

The interpolation unit 3 then performs determination selection processing on the 3D pose data $V\_3d^{(t+4)}$ obtained from the frame image data $D\_img(t+4)$ and the 3D pose data $PoseH\_3d^{(t+4)}$ obtained by the interpolation processing (processing at the time step t+4 in the sequence diagram in FIG. 14).

Specifically, the interpolation unit 3 compares the 3D pose data $V\_3d^{(t+4)}$ with the 3D pose data $PoseH\_3d^{(t+4)}$; if the difference between the two is within a predetermined range, the interpolation unit 3 determines that the prediction accuracy of the interpolation processing is high, and then transmits the 3D pose data $PoseH\_3d^{(t+4)}$ obtained by the interpolation processing as the 3D pose data $Pose\_3d^{(t+4)}$ at the time step t+4. Conversely, if the difference between the two is out of the predetermined range, the interpolation unit 3 determines that the prediction accuracy of the interpolation processing is low, and then transmits the 3D pose data $V\_3d^{(t+4)}$ obtained from the frame image data $D\_img^{(t+4)}$ as the 3D pose data $Pose\_3d^{(t+4)}$ at the time step t+4.

FIG. 10 shows a case where the difference between the 3D pose data $V\_3d^{(t+4)}$ and the 3D pose data $PoseH\_3d^{(t+4)}$ is small. Further, FIG. 11 shows a case where the difference between the 3D pose data $V\_3d^{(t+4)}$ and the 3D pose data $PoseH\_3d^{(t+4)}$ is large.

In the case of FIG. 10, the interpolation unit 3 performs comparison determination processing for determining whether the total sum of the norms (or Euclidean distances) of the vectors between the corresponding key points in the 3D pose data $V\_3d^{(t+4)}$ and the 3D pose data $PoseH\_3d^{(t+4)}$ is larger than a predetermined threshold value. The vectors between the corresponding key points are assumed to be set, for example, as shown in FIG. 12.

In other words, assuming that vec(a, b) is a vector from a point "a" to a point "b" in the three-dimensional space SP1, the vectors between the corresponding key points are the following 15 vectors vi to vis.

$$v_1 = vec(kp_3, kp_2)$$
$$v_2 = vec(kp_2, kp_1)$$
$$v_3 = vec(kp_3, kp_5)$$
$$v_4 = vec(kp_5, kp_6)$$
$$v_5 = vec(kp_6, kp_7)$$
$$v_6 = vec(kp_3, kp_4)$$
$$v_7 = vec(kp_3, kp_{14})$$
$$v_8 = vec(kp_{14}, kp_{15})$$
$$v_9 = vec(kp_{15}, kp_{16})$$
$$v_{10} = vec(kp_4, kp_8)$$
$$v_{11} = vec(kp_8, kp_9)$$
$$v_{12} = vec(kp_9, kp_{10})$$
$$v_{13} = vec(kp_4, kp_{11})$$
$$v_{14} = vec(kp_{11}, kp_{12})$$
$$v_{15} = vec(kp_{12}, kp_{13})$$

Note that the vectors between the key points corresponding to the 3D pose data $PoseH\_3d^{(t+4)}$ are defined as the vector vi to vis, and the vectors between the key points corresponding to the 3D pose data $V\text{-}3d^{(t+4)}$ are defined as the vector $v'_1$ to $v'_{15}$.

The interpolation unit 3 then performs processing corresponding to the following formula to obtain the total Ev (evaluation value Ev) of the sum of the norms (or Euclidean distances) of the difference vectors between the corresponding key points in the 3D pose data $V\_3d^{(t+4)}$ and the 3D pose data $PoseH\_3d^{(t+4)}$.

$$Ev = \sum_{i=1}^{M} \|v_i - v'_i\| \qquad \text{Formula 2}$$

M: the number of vectors between key points

The interpolation unit 3 then compares the evaluation value Ev obtained as described above with a predetermined threshold value Th1. Note that the evaluation value Ev for the 3D pose data $PoseH\_3d^{(t+4)}$ and the 3D pose data $V\_3d^{(t+4)}$ is denoted as $Ev(PoseH\_3d^{(t+4)}, V\_3d^{(t+4)})$.

(1) When $Ev(PoseH\_3d^{(t+4)}, V\_3d^{(t+4)}) >$ Th1 is satisfied, the interpolation unit 3 determines that the prediction accuracy of the interpolation processing performed by the pose data generation device 100 is low, and then transmits the 3D pose data $V\_3d^{(t+4)}$ obtained from $D\_img^{(t+4)}$ as the 3D pose data $Pose\_3d^{(t+4)}$ at the time step t+4 (for example, in the case of FIG. 11).

(2) When $Ev(PoseH\_3d^{(t+4)}, V\_3d^{(t+4)}) \geq$ Th1 is satisfied, the interpolation unit 3 determines that the prediction accuracy of the interpolation processing performed by the pose data generation device 100 is high, and then transmits the obtained 3D pose data PoseH_3d$^{(t+4)}$ obtained by the interpolation processing as 3D pose data Pose_3d$^{(t+4)}$ at the time step t+4 (for example, in the case of FIG. 10).

Processing as described above allows the pose data generation device 100 to output, at the time step t+4, 3D pose data with higher accuracy of (1) the 3D pose data V_3d$^{(t+4)}$ obtained from the frame image data D_img$^{(t+4)}$ and (2) the 3D pose data V_3d$^{(t+4)}$ obtained by interpolation processing. In other words, at the time step t+4 at which the frame image is to be obtained, the pose data generation device 100 can verify the accuracy of the interpolation processing that has been performed up to the time step t+4; if the accuracy of the interpolation processing is poor, the pose data generation device 100 outputs the 3D pose data V_3d$^{(t+4)}$ obtained from D_img(t+4). Thus, the accuracy of the 3D pose data obtained by the pose data generation device 100 can always be maintained at a certain level or higher.

In the above, the case of using vectors (vectors between corresponding key points) has been described, but the present invention should not be limited to this. For example, using a matrix (rotation matrix), a quaternion, and/or Euler angles, the pose data generation device 100 may select (output) data with higher accuracy of (1) the 3D pose data V_3d$^{(t+4)}$ obtained from frame image data D_img(t+4), and (2) the 3D pose data PoseH_3d$^{(t+4)}$ obtained by the interpolation processing. Specifically, the pose data generation device 100 expresses (species) the key points of the 3D pose data V_3d$^{(t+4)}$ and the key points of the 3D pose data PoseH_3d$^{(t+4)}$ corresponding to the key points using a matrix (rotation matrix), a quaternion or Euler angles. Using a matrix (rotation matrix), a quaternion, or Euler angles, the pose data generation device 100 obtains data indicating deviation amounts (for example scalar, vector, or tensor) between the key points of 3D pose data V_3d$^{(t+4)}$ and 3D pose data PoseH_3d$^{(t+4)}$ corresponding to the key points; based on the data indicating deviation amounts, the pose data generation device 100 may select (output) data with higher accuracy of (1) the 3D pose data V_3d$^{(t+4)}$ obtained from frame image data D_img(t+4), and (2) the 3D pose data PoseH 3d$^{(t+4)}$ obtained by the interpolation processing.

<<Processing after Time Step t+5>>

After the time step t+5, the pose data generation system 1000 repeatedly performs the same processing as described above. In other words, at the time step at which the frame image is to be obtained, the same processing as the processing at the time step t+4 is performed, and at the time step at which the frame image is not to be obtained, the same processing as the processing at the time steps t+1 to t+3 is performed.

As described above, (1) at the time step at which a frame image is to be obtained, the pose data generation system 1000 obtains 3D pose data based on the captured frame image by the imaging deviation Cam1, whereas (2) at the time step at which a frame image is not to be obtained, the pose data generation system 1000 predicts 3D pose data at the present time step from the previous time step(s) using IMU data, and performs interpolation processing (the above-described interpolation processing) using the prediction data, thereby obtaining 3D pose data. Thus, even when the rate (frame rate) of obtaining frame images by the imaging device Cam1 is low, the pose data generation system 1000 performs the above-described interpolation processing using IMU data, thereby obtaining 3D pose data with the high frame rate. In other words, since the pose data generation system 1000 does not need to use an imaging device for high frame rates, it can be realized at low cost, and can obtain 3D pose data by interpolation processing using IMU data, thereby obtaining highly accurate pose data (3D pose data).

First Modification

Next, a first modification of the first embodiment will be described. The same parts as those in the above embodiment are designated by the same reference numerals, and detailed description thereof will be omitted.

The pose data generation system of the present modification has the same configuration as the pose data generation system 1000 of the first embodiment, and the processing by the interpolation unit 3 is different from that of the first embodiment.

The interpolation unit 3 of the present modification performs processing using a time-series filter (for example, Kalman filter, the extended Kalman filter (EKF: the extended Kalman Filter), the unscented Kalman filter (UKF: the unscented Kalman Filter), Particle filter, or the like).

There is a technique using a time series filter as a technique for estimating the internal state of an observation target that changes from moment to moment. When a state vector $x_t$ is assumed to be an internal state of a target at the time step t (time t), and an observation vector $y_t$ is assumed to be a feature that has been observed at the time step t (time t), the time series filter is a method that estimates the internal state $x_t$ of the target that cannot be directly observed from the observation vector $y_t$.

A system model of the internal state of an observation target and a observation model (state space model) when the target has been observed can be expressed as follows.
System Model (State Equation):

$$x_t = f(x_{t-1}, u_t, w_t)$$

f: state transition function representing a state change between the time
step t−1 and the time step t
$u_t$: control input of the time step t
$w_t$: system noise at the time step t
Observation Model (Observation Equation):

$$z_t = h(x_t, v_t)$$

h: function representing the observation vector obtained in the state $x_t$
$v_t$: observation noise at the time step t
When the movement of a person (or the movement of a specific part of a person) can be expressed (predicted) by the equation of motion, or the like, a time series filter can be applied using data predicted by the equation of motion, or the like and the actual observation data (data specified from the IMU data).

In the pose data generation system of the present modification, the interpolation unit 3 performs time series filter processing using (1) the 3D pose data obtained at the previous time step (time step t−1) (data indicating the one time step previous internal state (corresponding to the above internal state $x_{t-1}$)) (2) 3D pose data (observation data (corresponding to the above observation vector $z_t$)) predicted from an equation (for example, a motion equation) that expresses physical phenomena regarding action(s) of the subject person Sub1 to be processed (or movement(s) of specific part(s) of the subject person Sub1), thereby obtaining (estimating) the internal state (pose data of the subject person Sub1) of the observation target at the current time step (time step t).

For example, when a nonlinear Kalman filter is used, the interpolation unit 3 performs the following processing to obtain (estimate) the internal state (pose data of the subject person Sub1) of the observation target at the current time step (time step t).

(A) Prediction $$x_{t|t-1} = f(x_{t-1|t-1}, u_t, 0)$$

$$P_{t|t-1} = F_t P_{t-1|t-1} F_t^T + G_t Q_t G_t^T$$

$x_{t|t-1}$: state estimation value of the time step t given the time step t−1 (state estimation vector)

$x_{t-1|t-1}$: state estimation value (state estimation vector) after update processing at the time step t−1.

$F_t$: linear model of system time transition $P_{t-1|t}$: covariance matrix of error $F^T_t$: transpose matrix of $F_t$ $G_t$: matrix of a noise model for time transition $Q_t$: covariance matrix of the noise model for time transitions $G^T_t$: transpose matrix of $G_t$ (B) Update $$e_t = z_t - h(x_{t|t-1}, 0)$$

$$S_t = H_t P_{t|t-1} H_t^T + R_t$$

$$K_t = P_{t|t-1} H_t^T + S_t^{-1}$$

$$x_{t|t} = x_{t|t-1} + K_t e_t$$

$$P_{t|t} = (I - K_t H_t) P_{t|t-1}$$

$e_t$: observation residuals at the time step t $S_t$: covariance of the observed residuals at the time step t $K_t$: optimal Kalman gain at the time step t $x_{t|t}$: estimated value (estimated vector) of the state updated at the time step t.

$P_{t|t}$: covariance of the updated error at time step t $H_t$: linear model for an observation model $R_t$: covariance of observed noise at the time step t Note that $F_t$ and $H_t$ are expressed by the following mathematical formulas when the extended Kalman filter is used as a nonlinear Kalman filter.

$$F_t = \left.\frac{\partial f}{\partial x}\right|_{x_{t-1|t-1}, u_t} \quad \text{Formula 3}$$

$$H_t = \left.\frac{\partial h}{\partial x}\right|_{x_{t|t-1}} \quad \text{Formula 4}$$

In other words, when the functions f and h of the above-mentioned state space model are nonlinear functions, the terms after the second derivative are omitted in the Taylor series, thereby approximating the nonlinear functions f and h to the order of the terms of the first derivative and linearizing the nonlinear functions f and h. This allows the Kalman filter algorithm to be applied.

In the above description, a case where the pose data generation system of the present modification performs interpolation processing for 3D pose data using the extended Kalman filter as a non-linear Kalman filter for a time series filter has been described, but the present invention should not be limited to this. Instead, for example, a Kalman filter, an unscented Kalman filter (UKF: the unscented Kalman Filter), a particle filter, or the like may be used as a time-series filter to perform the interpolation processing for 3D pose data.

As described above, when action(s) of a person (or movement(s) of specific part(s) of a person) can be expressed (predicted) by a motion equation or the like, the pose data generation system of the present modification performs the interpolation processing for 3D pose data using data predicted by the motion equation or the like and the actual observation data (data specified from the IMU data) while applying a time series filter. The pose data generation system of the present modification, 3D pose data obtains 3D pose data (3D pose data after interpolation processing) that can reproduce smoother movement, as compared with the pose data generation system 1000 of the first embodiment.

Second Embodiment

Next, the second embodiment will be described. The same parts as those in the above embodiment (including modified examples) are designated by the same reference numerals, and detailed description thereof will be omitted.

2.1: Configuration of Pose Data Generation System

Figure 15:
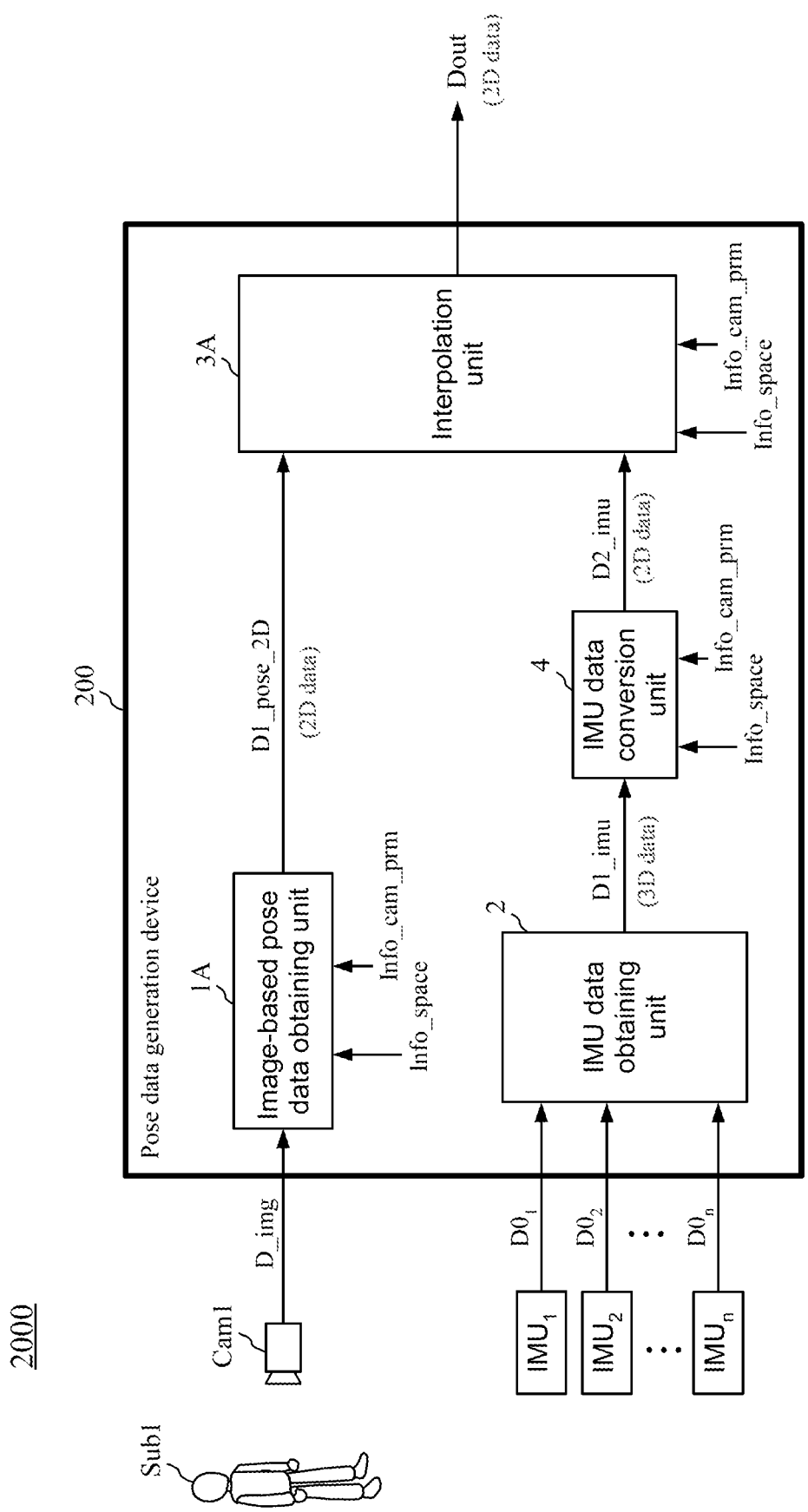
FIG. 15 is a schematic configuration diagram of a pose data generation system 2000 according to a second embodiment.

FIG. 15 is a schematic configuration diagram of the pose data generation system 2000 according to a second embodiment.

Figure 16:
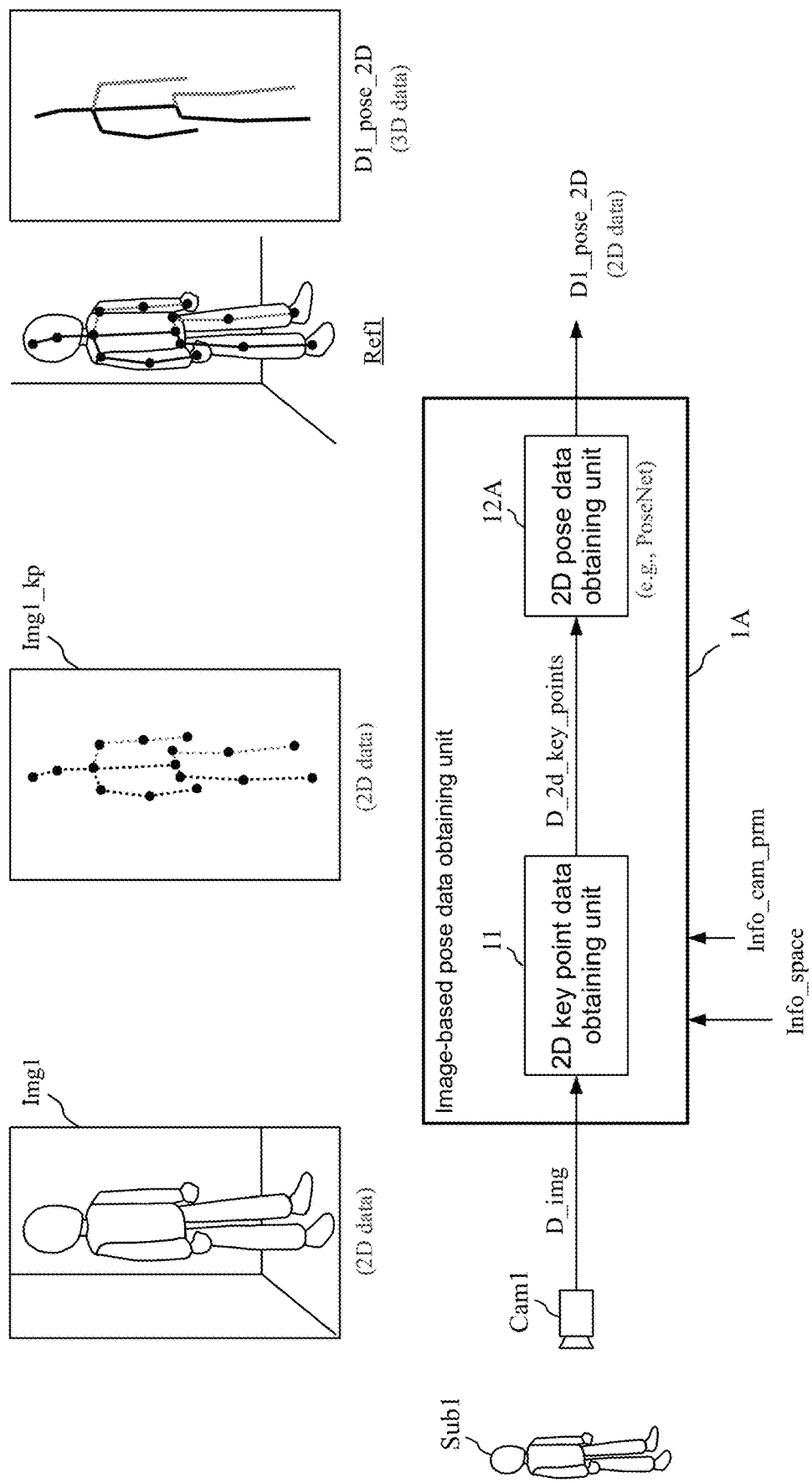
FIG. 16 is a schematic configuration diagram of an image-based pose data obtaining unit 1A according to the second embodiment.

FIG. 16 is a schematic configuration diagram of the pose data obtaining unit 1A according to the second embodiment.

As shown in FIG. 15, the pose data generation system 2000 of the second embodiment has a configuration in which the pose data generation device 100 is replaced with a pose data generation device 200 in the pose data generation system 1000 of the first embodiment. The pose data generation device 200 has a configuration in which the image-based pose data obtaining unit 1 of the pose data generation device 100 is replaced with an image-based pose data obtaining unit 1A, the interpolation unit 3 of the pose data generation device 100 is replaced with an interpolation unit 3A, and the IMU data conversion unit 4 is added.

The pose data generation system 1000 of the first embodiment obtains 3D pose data, whereas the pose data generation system 2000 of the second embodiment obtains 2D pose data.

The image-based pose data obtaining unit 1A includes, for example, a 2D key point data obtaining unit 11 and a 2D pose data obtaining unit 12A, as shown in FIG. 16.

The 2D key point data obtaining unit 11 has the same configuration and function as the 2D key point data obtaining unit 11 of the first embodiment.

The 2D pose data obtaining unit 12A receives the key point data D_2d_key_points transmitted from the 2D key point data obtaining unit 11. The 2D pose data obtaining unit 12A obtains a two-dimensional pose data from the key point data D_2d_key_points based on the information Info_space of the imaging space inputted into the image-based pose data obtaining unit 1A and the information Info_cam_prm of the imaging parameters of the imaging device Cam1. Specifically, the 2D pose data obtaining unit 12A obtains data including two-dimensional coordinate data of points (plural points) in the frame image (two-dimensional image) indicated by the key point data D_2d_key_points (two-dimensional coordinate data) as two-dimensional pose data D1_pose_2D. The 2D pose data obtaining unit 12A then transmits the obtained two-dimensional pose data D1_pose_2D to the interpolation unit 3A.

The IMU data conversion unit 4 receives the data D1_imu transmitted from the IMU data obtaining unit 2. Further, the IMU data conversion unit 4 receives information Info_space regarding the three-dimensional space (imaging space) imaged by the imaging device Cam1 and the imaging parameter Info_cam_prm of the imaging device Cam1. The IMU data conversion unit 4 converts the three-dimensional data D1_imu (for example, the angular velocity vector (three-dimensional data) in the three-dimensional space SP obtained by each inertial measurement unit $IMU_k$) transmitted from the IMU data obtaining unit 2 into two-dimensional data. Specifically, based on the information Info_space regarding the three-dimensional space (imaging space) imaged by the imaging device Cam1 and the photographing parameter Info_cam_prm of the imaging device Cam1, the IMU data conversion unit 4 converts the three-dimensional coordinate data (three-dimensional data D1 imu) into two-dimensional coordinate data in a frame image (two-dimensional image) obtained when the image is captured by the imaging device Cam1. The IMU data conversion unit 4 then transmits the data obtained by the above three-dimensional/two-dimensional coordinate conversion for the three-dimensional data D1_imu to the interpolation unit 3A as the data D2_imu.

The interpolation unit 3A receives the two-dimensional data D1_pose_2D transmitted from the image-based pose data obtaining unit 1A and the two-dimensional data D2_imu transmitted from the IMU data conversion unit 4. Further, the interpolation unit 3A receives information Info_space regarding the three-dimensional space (imaging space) imaged by the imaging device Cam1 and the imaging parameters Info_cam_prm of the imaging device Cam1.

(1) When the pose data D1_pose_2D is first inputted from the image-based pose data obtaining unit 1A at the time step at which the frame image data has been obtained, the interpolation unit 3A outputs the inputted pose data D1_pose_2D as output data Dout (two-dimensional pose data Dout), and stored and held the output data Dout.

(2) At the time step at which the frame image data has not been obtained, the interpolation unit 3A performs interpolation processing using the three-dimensional pose data Dout stored in the interpolation unit 3A and the data D2_imu obtained at the current time step based on the information Info_space regarding the imaging space and the imaging parameters Info_cam_prm of the imaging device Cam1, thereby obtaining pose data after interpolation processing. The interpolation unit 3A then transmits the obtained pose data after the interpolation processing as output data Dout, and stores and holds the output data.

(3) At the time step at which the frame image data has been obtained, the interpolation unit 3A performs interpolation processing using the three-dimensional pose data Dout stored in the interpolation unit 3A and the data D2 imu obtained at the current time step based on the information Info_space regarding the imaging space and the imaging parameters Info_cam_prm of the imaging device Cam1, thereby obtaining pose data after interpolation processing. Further, the interpolation unit 3A compares the inputted pose data D1_pose_2D (pose data obtained from the frame image data) with the pose data after the interpolation processing; according to the result of the comparison, the interpolation unit 3A selects one of the inputted pose data D1_pose_2D (pose data obtained from the frame image data) and the pose data after the above interpolation processing. The interpolation unit 3A then transmits the selected pose data as output data Dout, and stores and holds the output data Dout.

Note that the IMU data obtaining processing unit corresponds to the IMU data obtaining unit 2 and the IMU data conversion unit 4.

2.2: Operation of Pose Data Generation System

The operation of the pose data generation system 2000 configured as described above will be described below.

Hereinafter, for convenience of explanation, the operation of the pose data generation system 2000 when the subject person Sub1 acts shown in FIG. 4 will be described as in the first embodiment.

For convenience of explanation, it is assumed, as in the first embodiment, that three inertial measurement units $IMU_1$ to $IMU_3$ are attached to the subject person Sub1, the inertial measurement unit $IMU_1$ is attached to the head of the subject person Sub1, and the inertial measurement unit $IMU_2$ is attached to right wrist portion of the subject person Sub1, and the inertial measurement unit $IMU_3$ is attached to left wrist portion of the subject person Sub1.

FIGS. 17 to 20 are diagrams for explaining the pose data generation processing (including the interpolation processing) performed by the pose data generation system 2000.

Figure 21:
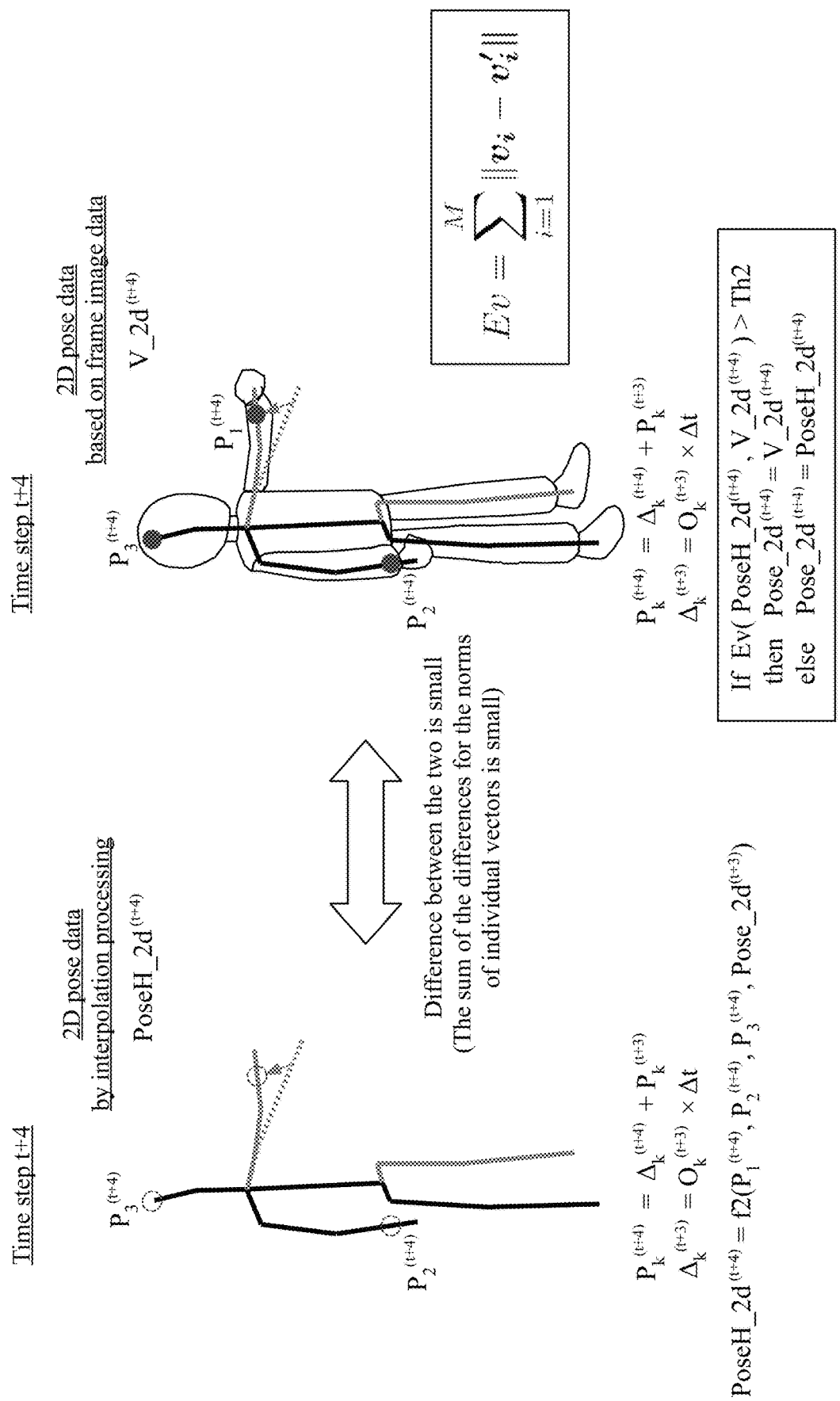
FIG. 21 is a diagram for explaining determination selection processing performed by the pose data generation system 2000.
Figure 22:
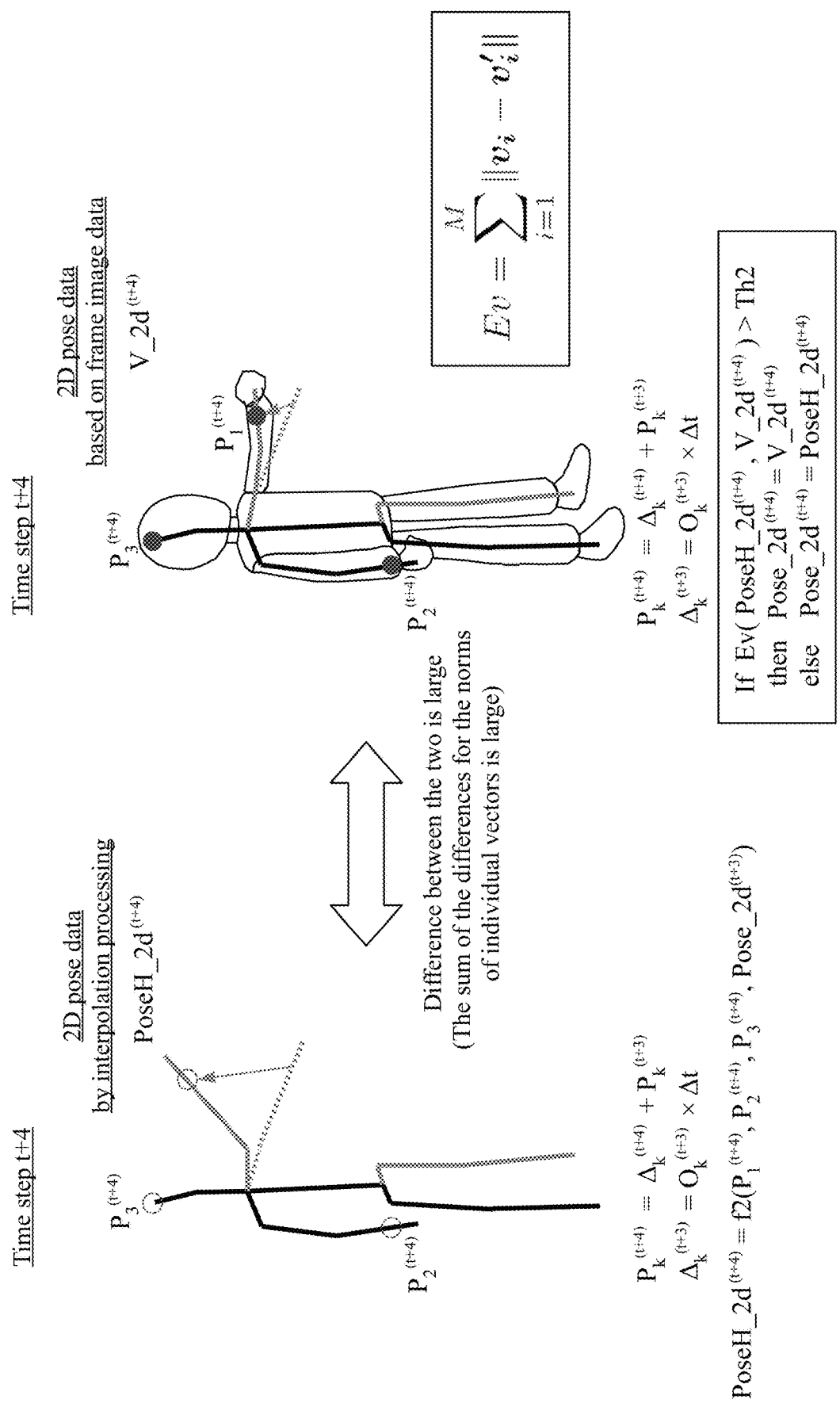
FIG. 22 is a diagram for explaining determination selection processing performed by the pose data generation system 2000.
Figure 23:
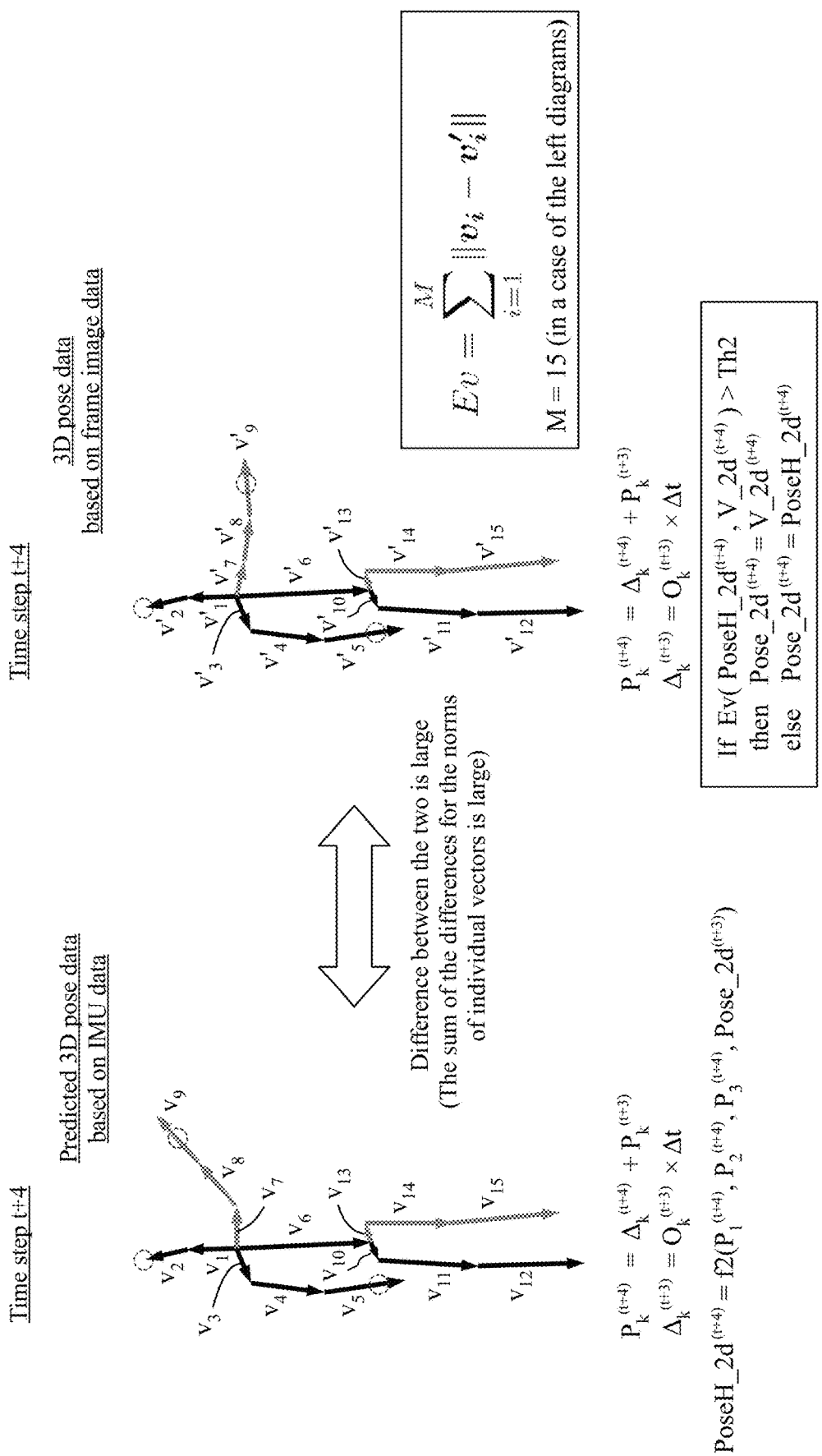
FIG. 23 is a diagram for explaining determination selection processing performed by the pose data generation system 2000.

FIGS. 21 to 23 are diagrams for explaining the determination selection processing performed by the pose data generation system 2000.

Figure 24:
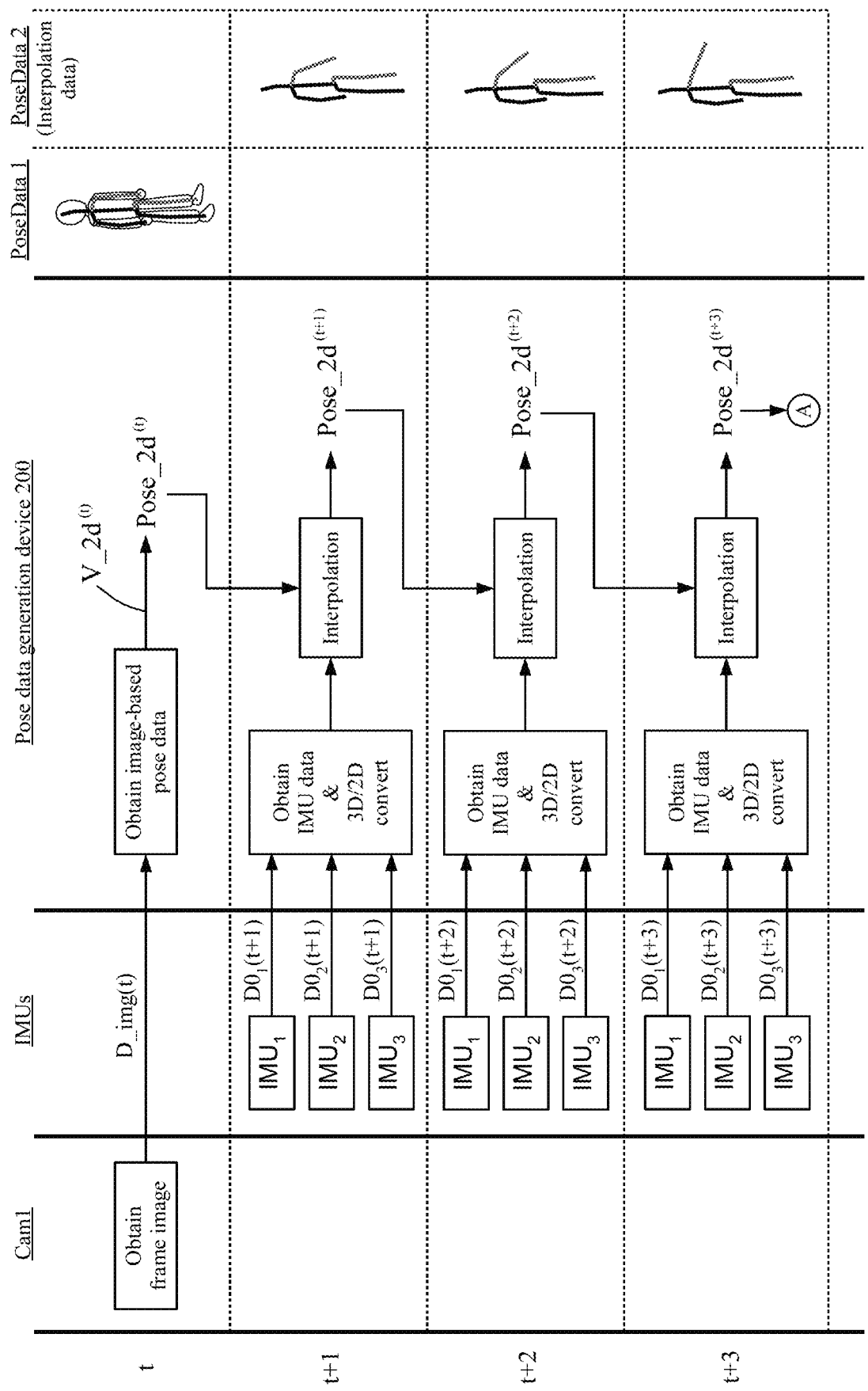
FIG. 24 is a sequence diagram of processing performed by the pose data generation system 2000.
Figure 25:
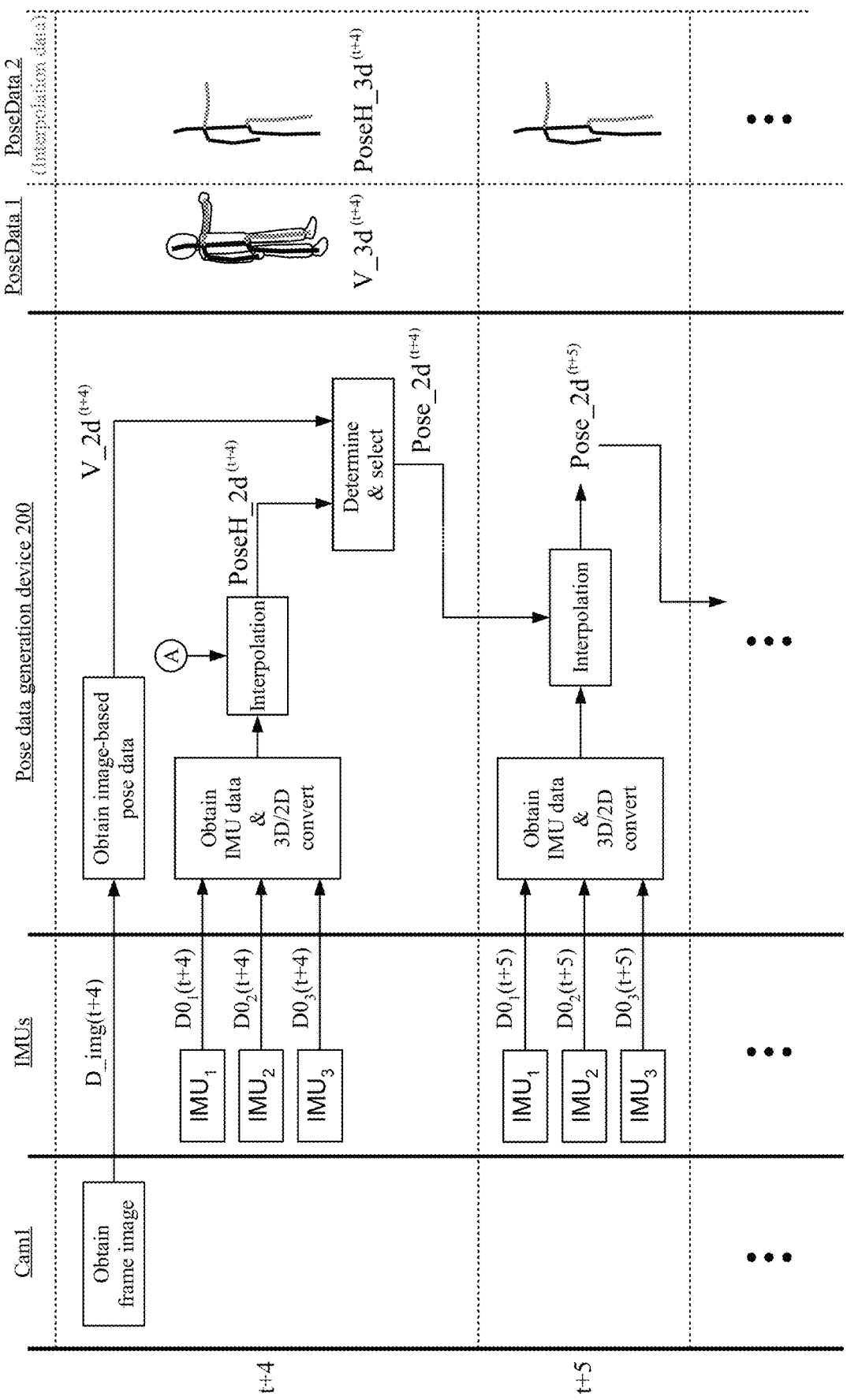
FIG. 25 is a sequence diagram of processing performed by the pose data generation system 2000.

FIGS. 24 to 25 are sequence diagrams of processing performed by the pose data generation system 2000. In FIGS. 24 and 25, the column shown by "PoseData1" shows the pose data obtained from the frame image data, and the column shown by "PoseData2" shows the pose data obtained by the interpolation processing.

Hereinafter, the operation of the pose data generation system 2000 will be described with reference to the drawings.

As in the first embodiment, the imaging space is set in the three-dimensional space SP1 as shown in FIG. 4, the three-dimensional coordinate system (origin o, x-axis, y-axis, and z-axis) is set as shown in FIG. 4, and the subject person Sub1 is targeted for tracking.

Further, as an example, in the pose data generation system 2000, a case where frame images are obtained at 4-time step intervals and three pieces of pose data are generated by interpolation processing during a period in which the frame images has not been obtained will be described below.

<<Processing at Time Step t>>

At the time step t, the frame image data D_img(t) is obtained by capturing an image of the three-dimensional space (imaging space SP1) including the subject person Sub1 by the imaging device Cam1. The image (frame image) formed by the frame image data D_img(t) is an image Img1 shown in the upper left figure of FIG. 16.

The image-based pose data obtaining unit 1A receives the frame image data D_img(t) transmitted from the imaging device Cam1 and performs processing for obtaining two-dimensional pose data from the frame image data D_img(t). Specifically, the following processing is performed.

The 2D key point data obtaining unit 11 of the image-based pose data obtaining unit 1A (1) extracts an image region corresponding to the subject person Sub1 in the frame image (image Img1) formed by the frame image data D_img(t), and (2) specifies positions in the frame image (positions in the two-dimensional image) of predetermined portions of the subject person Sub1 based on the information Info_space of the imaging space inputted into the image-based pose data obtaining unit 1A and the information Info_cam_prm of the imaging parameters of the imaging device Cam1. Here, the "predetermined portions" are (1) predetermined positions included in the head and spine of a person (corresponding to the key points $kp_1$ to $kp_4$ in FIGS. 3) and (2) predetermined positions included in the left and right arms of the person (corresponding to key points $kp_5$ to $kp_7$ and $kp_{14}$ to $kp_{16}$ in FIG. 3), and (3) predetermined positions included in the left and right legs of a person (corresponding to key points $kp_5$ to $kp_{10}$ and $kp_{11}$ to $kp_{13}$ in FIG. 3). The key points specified by the key point data D_2d_key_points correspond to 16 points $kp_1$ to $kp_{16}$ as shown in FIG. 3.

In the pose data generation system 2000, the tracking target is a person (the standard human size is known), and the installation position in the three-dimensional space, the direction of the camera optical axis, the focal length, and the angle of view of the imaging device Cam1 are known; thus, the pose data generation system 2000 can extract an image region corresponding to the subject person Sub1 from the frame image obtained by the imaging device Cam1, and can determine the positions of specific portions of the subject person Sub1 in the frame image.

The 2D key point data obtaining unit 11 then transmits the key point data obtained by the above processing to the 2D pose data obtaining unit 12A as data D_2d_key_points.

The 2D pose data obtaining unit 12A receives the key point data D_2d_key_points transmitted from the 2D key point data obtaining unit 11. The 2D pose data obtaining unit 12A obtains two-dimensional pose data from the key point data D_2d_key_points based on the information Info_space of the imaging space inputted into the image-based pose data obtaining unit 1 and the information Info_cam_prm of the imaging parameters of the imaging device Cam1. Specifically, the 2D pose data obtaining unit 12A obtains data including two-dimensional coordinate data of points (a plurality of points) in the frame image (two-dimensional image) indicated by the key point data D_2d_key_points (two-dimensional coordinate data) as two-dimensional pose data D1_pose_2D. The 2D pose data obtaining unit 12A then transmits the obtained two-dimensional pose data D1_pose_2D to the interpolation unit 3A.

In the pose data generation system 2000, the tracking target is a person (the standard human size is known), the installation position in the three-dimensional space, the direction of the camera optical axis, the focal length, and the angle of view of the imaging device Cam1 are known, and furthermore the information for specifying the three-dimensional space SP1 that has been set as the imaging space is known; thus, from the positions in the frame image (the coordinate positions in the imaging space SP1) of the specific portions of the subject person Sub1, the pose data generation system 2000 can estimate the coordinate positions of the specific portions of the subject person Sub1. In other words, the pose data generation system 2000 can estimate the coordinate information (three-dimensional coordinate data) in the three-dimensional space SP1 of each key point from the key point data D_2d_key_points (two-dimensional coordinate data of each key point in the two-dimensional image), and furthermore can estimate the coordinate information (two-dimensional coordinate data) in the frame image of each key point.

Note that the processing (estimation processing) for estimating the coordinate information (two-dimensional coordinate data) of each key point from the key point data D_2d_key_points (two-dimensional coordinate data of each key point in the two-dimensional image) may use calculation processing based on the information of the imaging space SP1 and the imaging parameters of the imaging device Cam1, or may be the one using the processing by the neural network. When using the processing by the neural network as the above estimation processing, for example, the processing is performed as follows. In such processing, the key point data of the person obtained from the two-dimensional image (frame image) of the person is set to input data, the coordinate data (two-dimensional coordinate data) in the two-dimensional image (a captured frame image) of each key point of the key point data is set to supervised data for output data, and then the training process of a neural network model is performed. Performing the training process obtains a trained model that inputs the key point data of the person obtained from the two-dimensional image (frame image) of the person and outputs prediction data of the two-dimensional coordinate data (two-dimensional coordinate data in the frame image) of each key point of the key point data. Performing processing using the trained model allows for achieving estimation processing for estimating coordinate information (two-dimensional coordinate data) of each key point from the key point data D_2d_key_points (two-dimensional coordinate data of each key point in the 2D image).

The 2D pose data obtaining unit 12A transmits data including coordinate data (two-dimensional coordinate data) in the two-dimensional image (frame image) of each key point obtained by the above processing as data D1_pose_2D (data obtained at the time step t is referred to as D1_pose_2D (t)) to the interpolation unit 3A.

As shown in the upper right figure of FIG. 16, data D1_pose_2D (2D pose data) is shown as a diagram in which points specified by the coordinate data (two-dimensional coordinate data) in the two-dimensional image of individual key points are connected by lines. Further, the 2D pose data D1_pose_2D obtained by the image-based pose data obtaining unit TA at the time step t is referred to as $V\_2d^{(t)}$.

Figure 17:
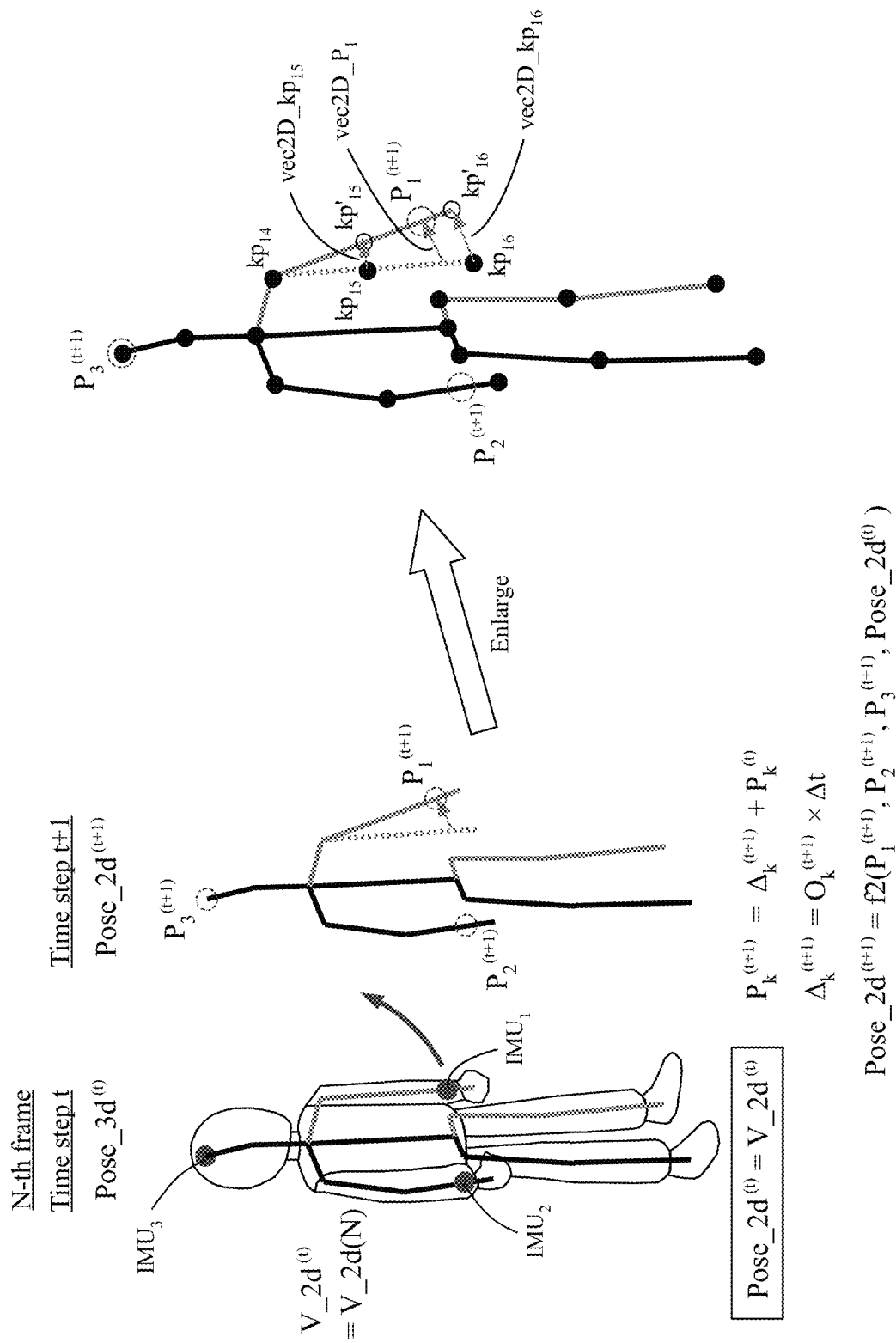
FIG. 17 is a diagram for explaining pose data generation processing (including interpolation processing) performed by the pose data generation system 2000.

At the time step t, the interpolation unit 3A receives the data D1_pose_2D ($=V\_2d^{(t)}$) transmitted from the image-based pose data obtaining unit TA, and transmits the received data, as it is, as the output data Dout (see the diagram at the time step t in FIG. 17 and the processing at the time step t in FIG. 24). Further, the interpolation unit 3A stores and holds the output data Dout as the 2D pose data Pose_2d$^{(t)}$ ($=V\_2d^{(t)}$) at the time step t. Note that data transmitted from the interpolation unit 3A at the time step t is referred to as data Pose_2d$^{(t+1)}$.

Further, the interpolation unit 3A determines (estimate) the position (coordinate position) of the inertial measurement unit IMU$_k$ (k is a natural number satisfying 1≤k≤3) in the three-dimensional space SP1 at the time step t using the 2D pose data Pose_2d$^{(t+1)}$. The mounting position of the inertial measuring device IMU$_k$ is known and the imaging parameters of the imaging device Cam1 is known; thus, the interpolation unit 3A determines (estimates) the position in the three-dimensional space SP1 corresponding to the mounting position of the inertial measuring device IMU$_k$ based on the 2D pose data Pose_2d$^{(t+1)}$, and furthermore determines (estimates) the position in the two-dimensional image corresponding to the mounting position of the inertial measurement device IMU$_k$. For example, the inertial measurement unit IMU$_1$ is attached to the left list portion of the subject person Sub1 as shown in the right figure of FIG. 5; thus, referring to the 2D pose data Pose_2d$^{(t+1)}$, the position (coordinate position in the three-dimensional space SP1) (the position indicated by $P_1^{(t)}$ in the right figure of FIG. 5) corresponding to the left list of the subject person Sub1 is determined, and furthermore the position in the two-dimensional image is determined (estimated). Thus, the interpolation unit 3A stores and holds the two-dimensional coordinate data of the inertial measurement unit $IMU_k$ determined (estimated) as described above as data $P_k(t)$. Note that in the present embodiment, $P_k(t)$ is as follows.

$$P_k^{T(t)} = [x_k^{(t)}, y_k^{(t)}]$$

$x_k^{(t)}$: x-coordinate in the two-dimensional image of the inertial measurement unit $IMU_k$ at the time step t
$y_k^{(t)}$: y-coordinate in the two-dimensional image of the inertial measurement unit $IMU_k$ at the time step t
$P^T{}_k^{(t)}$: transposed matrix of the matrix $P_k(t)$
k: a natural number satisfying 1≤k≤3

<<Processing at Time Step t+1>>

The inertial measurement units $IMU_1$ to $IMU_3$ obtain, at the time step t+1, IMU data $D0_1(t+1)$ to $D0_3(t+1)$, respectively, and transmit the obtained IMU data to the IMU data obtaining unit 2 of the pose data generation device 200. Note that a case where the inertial measurement units $IMU_1$ to $IMU_3$ are assumed to obtain angular velocity data will be described below. Further, the IMU data obtained by the inertial measurement unit $IMU_k$ at the time step t is referred to as $D0_k(t)$.

The IMU data obtaining unit 2 receives data $D0_1(t+1)$ to $D0_3(t+1)$ transmitted from the inertial measurement units $IMU_1$ to $IMU_3$, respectively. The IMU data obtaining unit 2 obtains the received data, in which $D0_1$ to $D0_1$ are integrated, as data D1_imu(t+1), and transmits the obtained data D1_imu(t+1) to the IMU data conversion unit 4.

The IMU data conversion unit 4 receives the data D1 imu(t+1) transmitted from the IMU data obtaining unit 2. Further, the IMU data conversion unit 4 receives information Info_space regarding the three-dimensional space (imaging space) imaged by the imaging device Cam1 and the imaging parameters Info_cam_prm of the imaging device Cam1. The IMU data conversion unit 4 converts the three-dimensional data D1_imu(t+1) (for example, the angular velocity vector (three-dimensional data) in the three-dimensional space SP obtained by each inertial measurement unit $IMU_k$) transmitted from the IMU data obtaining unit 2 into two-dimensional data. Specifically, based on the information Info_space regarding the three-dimensional space (imaging space) imaged by the imaging device Cam1 and the photographing parameter Info_cam_prm of the imaging device Cam1, the IMU data conversion unit 4 converts the three-dimensional coordinate data (three-dimensional data D1_imu(t+1)) into two-dimensional coordinate data in a frame image (two-dimensional image) obtained when the image is captured by the imaging device Cam1. The IMU data conversion unit 4 then transmits the data obtained by the above three-dimensional/two-dimensional coordinate conversion for the three-dimensional data D1_imu to the interpolation unit 3A as the data D2_imu(t+1).

The interpolation unit 3A obtains the two-dimensional coordinate position data $P_1^{(t+)}$ to $P_3^{(t+1)}$ of the inertial measurement units $IMU_1$ to $IMU_3$ at the time step t+1 using (1) data (data D2 imu(t+1)) after three-dimensional/two-dimensional coordinate conversion using the IMU data $D0_1(t+1)$ to $D0_3(t+1)$ obtained at the time step t+1 and (2) the two-dimensional coordinate position data $P_1^{(t)}$ to $P_3^{(t)}$ of the inertial measurement units $IMU_1$ to $IMU_3$ at the time step t, which has been stored and held in the interpolation unit 3. Specifically, the interpolation unit 3A performs processing corresponding to the following formula to obtain the two-dimensional coordinate position data $P_1(t+1)$ to $P_3(t+1)$ of the inertial measurement units $IMU_1$ to $IMU_3$ at the time step t+1.

$$P_k^{(t+1)} = \Delta_k^{(t+1)} + P_k^{(t)} \quad \text{Formula 5}$$

$$P_k^{(t+1)} = \begin{pmatrix} x_k^{(t+1)} \\ y_k^{(t+1)} \end{pmatrix}$$

$$\Delta_k^{(t+1)} = \begin{pmatrix} \Delta x_k^{(t+1)} \\ \Delta y_k^{(t+1)} \end{pmatrix}$$

$$P_k^{(t)} = \begin{pmatrix} x_k^{(t)} \\ y_k^{(t)} \end{pmatrix}$$

k: a natural number satisfying 1≤k≤3)

$$\Delta_k^{(t+1)} = O_k^{(t+1)} \times \Delta t$$

$$O_k^{T(t+1)} = [\omega x_k^{(t+1)}, \omega y_k^{(t+1)}]$$

Δt: time interval between the time step t and the time step t+1
$O^T{}_k^{(t+1)}$: transposed matrix of $O_k^{(t+1)}$ Note that $\omega x_k^{(t+1)}$ is data after 3Dcoordinate-to-2Dcoordinate conversion in which the x-component data of the 3D spatial coordinates of the angular velocity obtained by the inertial measuring device $IMU_k$ at the time step t+1 into data of the 2D coordinates; that is, $\omega x_k^{(t+1)}$ is x-component data in the two-dimensional image. $\omega y_k^{(t+1)}$ is data after 3Dcoordinate-to-2Dcoordinate conversion in which the y-component data of the 3D spatial coordinates of the angular velocity obtained by the inertial measuring device $IMU_k$ at the time step t+1 into data of the 2D coordinates; that is, $\omega y_k^{(t+1)}$ is y-component data in the two-dimensional image. $\omega z_k^{(t+1)}$ is data after 3Dcoordinate-to-2Dcoordinate conversion in which the z-component data of the 3D spatial coordinates of the angular velocity obtained by the inertial measuring device $IMU_k$ at the time step t+1 into data of the 2D coordinates; that is, $\omega z_k^{(t+1)}$ is z-component data in the two-dimensional image.

The interpolation unit 3A multiplies each component, in the two-dimensional image, of the angular velocity obtained by the inertial measurement unit $IMU_k$ at the time step t+1 by the elapsed time At from the time step t to the time step t+1, thereby obtaining (estimating) the displacement amount of each component (x-component, y-component). In other words, the interpolation unit 3 performs processing corresponding to the following formulas to obtain (estimate) the displacement amount (movement amount) from the time step t to the time step t+1 of the inertial measurement unit $IMU_k$.

$$\Delta x_k^{(t+1)} = \omega x_k^{(t+1)} \times \Delta t$$

$$\Delta y_k^{(t+1)} = \omega y_k^{(t+1)} \times \Delta t$$

The interpolation unit 3A performs interpolation processing using (1) the 3D pose data Pose $2d^{(t)}$ (=V_$2d^{(t)}$) at the time step t and (2) the two-dimensional coordinate position data $P_1^{(t+1)}$ to $P_3^{(t+1)}$, which has been obtained as describe above, of the inertial measuring devices $IMU_1$ to $IMU_3$ at the time step t+1, thereby obtaining the 3D pose data Pose_2d$^{(t+1)}$ at the time step t+1.

Specifically, the interpolation unit 3 performs processing corresponding to the following formulas to obtain the 2D pose data Pose_2d$^{(t+1)}$ at the time step t+1

$$\text{Pose\_2}d^{(t+1)} = f2\bigl(P_1^{(t+1)}, P_2^{(t+1)}, P_3^{(t+1)}, \text{Pose\_2}d^{(t)}\bigr)$$

The function f2 is a function for obtaining the 3D pose data Pose 2d$^{(t+1)}$ at the time step t+1 from $P_1^{(t+1)}$ to $P_3^{(t+1)}$ and Pose_2d$^{(t)}$.

Specifically, when the position of the inertial measurement unit $IMU_k$ is assumed to be the above estimated position at the time step t+1, the interpolation unit 3A predicts how each key point moves considering the degree of freedom of human joints and the movable range of each part. For example, as shown in the right figure of FIG. 17 (enlarged view of the figure at time step t+1), it is estimated that the position of the inertial measurement unit $IMU_1$ has moved from $P_1$ to $P_1^{(t+1)}$ (the vector (in the two-dimensional image) from $P_1^{(t)}$ to $P_1^{(t+1)}$ is referred to as vec2D_$P_1$), and thus the interpolation unit 3A, considering the vector vec2D_$P_1$, estimates that a movement vector for the key point $kp_{15}$ (key point data specified from Pose_2d(O) at the time step t+1 is the vector vec2D_$kp_{15}$ (the vector vec2D_$kp_{15}$ in FIG. 17) and the position at the time step t+1 of the key point $kp_{15}$ is the position kp'$_{15}$ shown in FIG. 17. Similarly, the interpolation unit 3A, considering the vector vec2D_$P_1$, estimates that a movement vector for the key point $kp_{16}$ (key point data specified from Pose_2d$^{(t)}$) at the time step t+1 is the vector vec2D_$kp_{16}$ (the vector vec2D_$kp_{16}$ in FIG. 17) and the position at the time step t+1 of the key point $kp_{16}$ is the position kp'$_{16}$ shown in FIG. 17.

Since the positions of the inertial measurement units $IMU_2$ and $IMU_3$ have not changed, it is estimated that the positions of the key points $kp_1$ to $kp_{14}$ (key point data specified from Pose_2d$^{(t+1)}$) has not changed in the period from the time step t to the time step t+1.

Based on the two-dimensional coordinate data of the key points obtained by the above processing (estimation (corresponding to the processing by using the function f2)), the interpolation unit 3A obtains the 2D pose data Pose 2d$^{(t+1)}$ (the 2D pose data Pose_2d$^{(t+1)}$ shown in FIG. 17) at the time step t+1.

The interpolation unit 3A then transmits the 2D pose data Pose_2d$^{(t+1)}$ obtained by the above processing (processing at the time step t+1 in the sequence diagram of FIG. 24) and stores the data.

Further, the interpolation unit 3A stores and holds the two-dimensional coordinate position data $P_1^{(t+1)}$ to $P_3(t+^1)$ of the inertial measurement units $IMU_1$ to $IMU_3$ at the time step t+1.

<<Processing at Time Step t+2>>

At the time step t+2, the inertial measurement units $IMU_1$ to $IMU_3$ obtain IMU data $D0_1$(t+2) to $D0_3$(t+2), respectively, and transmit the obtained IMU data to the IMU data obtaining unit 2 of the pose data generation device 200.

The IMU data obtaining unit 2 receives data $D0_1$(t+2) to $D0_3$(t+2) transmitted from the inertial measurement units $IMU_1$ to $IMU_3$, respectively. The IMU data obtaining unit 2 obtains the received data, in which $D0_1$ to $D0_n$ are integrated, as data D1_imu(t+2), and transmits the obtained data D1_imu(t+2) to the IMU data conversion unit 4.

The IMU data conversion unit 4 receives the data D1 imu(t+2) transmitted from the IMU data obtaining unit 2. Further, the IMU data conversion unit 4 receives information Info_space regarding the three-dimensional space (imaging space) imaged by the imaging device Cam1 and the imaging parameters Info_cam_prm of the imaging device Cam1. The IMU data conversion unit 4 converts the three-dimensional data D1_imu(t+2) transmitted from the IMU data obtaining unit 2 (for example, an angular velocity vector (three-dimensional data) in the three-dimensional space SP obtained by each inertial measurement unit $IMU_k$) into two-dimensional data. Specifically, based on the information Info_space regarding the three-dimensional space (imaging space) imaged by the imaging device Cam1 and the photographing parameter Info_cam_prm of the imaging device Cam1, the IMU data conversion unit 4 converts the three-dimensional coordinate data (three-dimensional data D1 imu(t+2)) into two-dimensional coordinate data in a frame image (two-dimensional image) obtained when the image is captured by the imaging device Cam1. The IMU data conversion unit 4 then transmits the data obtained by the above three-dimensional/two-dimensional coordinate conversion for the three-dimensional data D1_imu to the interpolation unit 3A as the data D2_imu(t+2).

The interpolation unit 3A obtains the two-dimensional coordinate position data $P_1^{(t+2)}$ to $P_3^{(t+2)}$ of the inertial measurement units $IMU_1$ to $IMU_3$ at the time step t+2 using (1) data (data D2 imu(t+2)) after three-dimensional/two-dimensional coordinate conversion using the IMU data $D0_1$(t+2) to $D0_3$(t+2) obtained at the time step t+2 and (2) the two-dimensional coordinate position data $P_1^{(t+1)}$ to $P_3^{(t+1)}$ of the inertial measurement units $IMU_1$ to $IMU_3$ at the time step t+1, which has been stored and held in the interpolation unit 3A.

Specifically, the interpolation unit 3A performs the same processing as at time step t+1 to obtain the two-dimensional coordinate position data $P_1^{(t+2)}$ to $P_3^{(t+2)}$ of the inertial measurement units $IMU_1$ to $IMU_3$ at the time step t+2.

The interpolation unit 3A performs processing corresponding to the following formula in the same manner as at the time step t+1 to obtain the 2D pose data Pose_2d$^{(t+2)}$ at the time step t+2.

$$\text{Pose\_2}d^{(t+2)} = f2\bigl(P_1^{(t+2)}, P_2^{(t+2)}, P_3^{(t+2)}, \text{Pose\_2}d^{(t+1)}\bigr)$$

Figure 18:
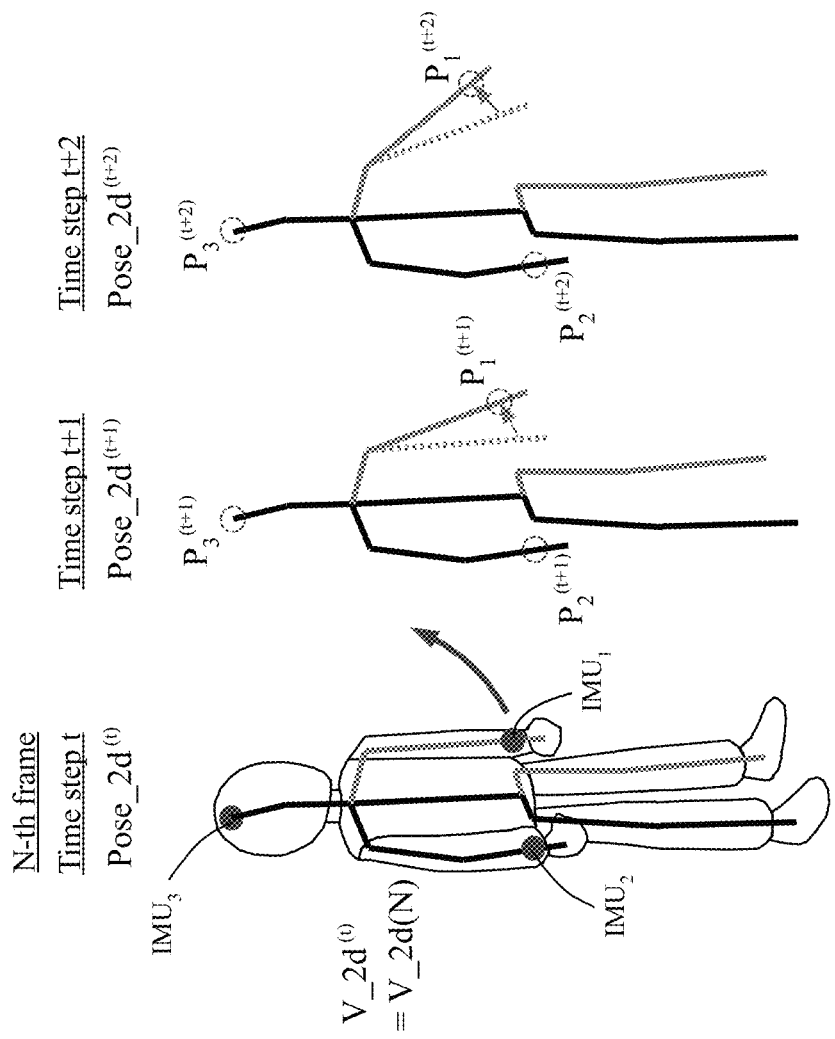
FIG. 18 is a diagram for explaining pose data generation processing (including interpolation processing) performed by the pose data generation system 2000.

As a result, the interpolation unit 3A obtains the 2D pose data Pose_2d$^{(t+2)}$ at the time step t+2 as shown in FIG. 18.

The interpolation unit 3A then transmits the 2D pose data Pose_2d$^{(t+2)}$ obtained by the above processing (processing at the time step t+2 in the sequence diagram of FIG. 24) and stores the data.

Further, the interpolation unit 3A stores and holds the two-dimensional coordinate position data $P_1^{(t+2)}$ to $P_3^{(t+2)}$ of the inertial measurement units $IMU_1$ to $IMU_3$ at the time step t+2.

<<Processing at Time Step t+3>>

At the time step t+3, the inertial measurement units $IMU_1$ to $IMU_3$ obtain IMU data $D0_1$(t+3) to $D0_3$(t+3), respectively, and transmit the obtained IMU data to the IMU data obtaining unit 2 of the pose data generation device 200.

The IMU data obtaining unit 2 receives data $D0_1$(t+3) to $D0_3$(t+3) transmitted from the inertial measurement units $IMU_1$ to $IMU_3$, respectively. The IMU data obtaining unit 2 obtains the received data, in which $D0_1$ to $D0_1$ are integrated, as data D1_imu(t+3), and transmits the obtained data D1 imu(t+3) to the IMU data conversion unit 4.

The IMU data conversion unit 4 receives the data D1 imu(t+3) transmitted from the IMU data obtaining unit 2. Further, the IMU data conversion unit 4 receives information Info_space regarding the three-dimensional space (imaging space) imaged by the imaging device Cam1 and the imaging parameters Info_cam_prm of the imaging device Cam1. The IMU data conversion unit 4 converts the three-dimensional data D1_imu(t+3) transmitted from the IMU data obtaining unit 2 (for example, an angular velocity vector (three-dimensional data) in the three-dimensional space SP obtained by each inertial measurement unit $IMU_k$) into two-dimensional data. Specifically, based on the information Info_space regarding the three-dimensional space (imaging space) imaged by the imaging device Cam1 and the photographing parameter Info_cam_prm of the imaging device Cam1, the IMU data conversion unit 4 converts the three-dimensional coordinate data (three-dimensional data D1 imu(t+3)) into two-dimensional coordinate data in a frame image (two-dimensional image) obtained when the image is captured by the imaging device Cam1. The IMU data conversion unit 4 then transmits the data obtained by the above three-dimensional/two-dimensional coordinate conversion for the three-dimensional data D1_imu to the interpolation unit 3A as the data D2_imu(t+3).

The interpolation unit 3A obtains the two-dimensional coordinate position data $P_1^{(t+3)}$ to $P_3(t+3)$ of the inertial measurement units $IMU_1$ to $IMU_3$ at the time step t+3 using (1) data (data D2 imu(t+3)) after three-dimensional/two-dimensional coordinate conversion using the IMU data $D0_1$(t+3) to $D0_3$(t+3) obtained at the time step t+3 and (2) the two-dimensional coordinate position data $P_1^{(t+2)}$ to $P_3^{(t+2)}$ of the inertial measurement units $IMU_1$ to $IMU_3$ at the time step t+2, which has been stored and held in the interpolation unit 3A.

Specifically, the interpolation unit 3A performs the same processing as at time step t+1 to obtain the two-dimensional coordinate position data $P_1^{(t+3)}$ to $P_3^{(t+3)}$ of the inertial measurement units $IMU_1$ to $IMU_3$ at the time step t+3.

The interpolation unit 3A performs processing corresponding to the following formula in the same manner as at the time step t+1 to obtain the 2D pose data Pose $2d^{(t+3)}$ at the time step t+2.

$$\text{Pose\_2}d^{(t+3)} = f2\left(P_1^{(t+3)}, P_2^{(t+3)}, P_3^{(t+3)}, \text{Pose\_2}d^{(t+2)}\right)$$

Figure 19:
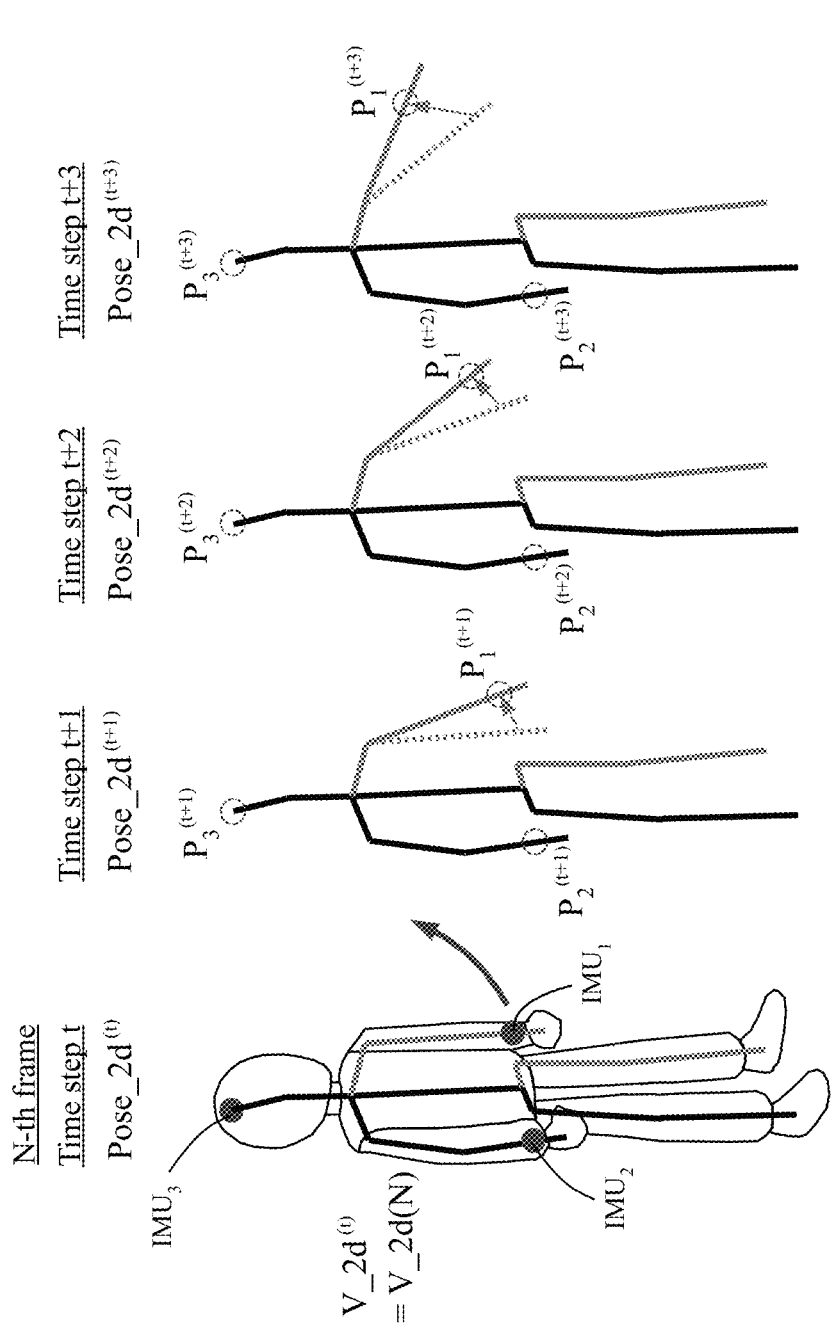
FIG. 19 is a diagram for explaining pose data generation processing (including interpolation processing) performed by the pose data generation system 2000.
Figure 20:
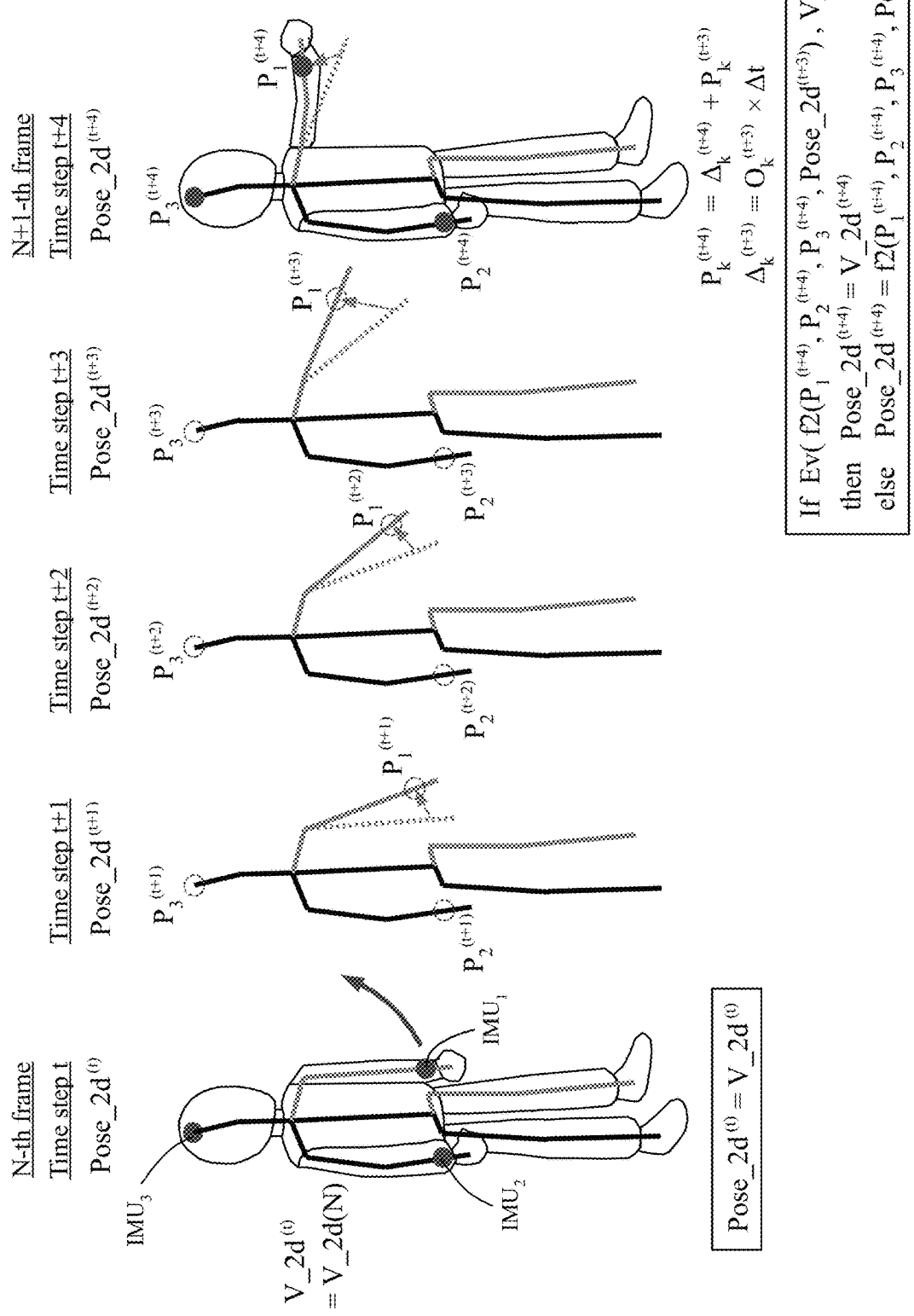
FIG. 20 is a diagram for explaining pose data generation processing (including interpolation processing) erperformed by the pose data generation system 2000.

As a result, the interpolation unit 3A obtains the 2D pose data Pose_$2d^{(t+3)}$ at the time step t+3 as shown in FIG. 19.

The interpolation unit 3A then transmits the 2D pose data Pose_$2d^{(t+3)}$ obtained by the above processing (processing at the time step t+3 in the sequence diagram of FIG. 24) and stores the data.

Further, the interpolation unit 3A stores and holds the two-dimensional coordinate position data $P_1^{(t+3)}$ to $P_3^{(t+3)}$ of the inertial measurement units $IMU_1$ to $IMU_3$ at the time step t+3.

<<Processing of Time Step t+4>>

At the time step t+4, the frame image data D_img(t+4) is obtained by capturing an image of the three-dimensional space (imaging space SP1) including the subject person Sub1 by the imaging device Cam1.

The image-based pose data obtaining unit 1A performs the same processing as the processing at the time step t to obtain the two-dimensional pose data D1_pose_2D(t+4) (=V_1$d^{(t+4)}$) from the frame image data D_img(t+4) transmitted from the imaging device Cam1, The interpolation unit 3A specifies (estimates) the position (coordinate position) of the inertial measurement unit $IMU_k$ (k is a natural number satisfying 1≤k≤3) in the three-dimensional space SP1 at the time step t using the 2D pose data V_$2d^{(t+4)}$ in the same manner as at the time step t. As a result, the interpolation unit 3A obtains the two-dimensional coordinate data $P_1^{(t+4)}$ to $P_3^{(t+4)}$ of the inertial measurement units $IMU_1$ to $IMU_3$.

Further, the interpolation unit 3A performs the same interpolation processing as at the time step t+1. In other words, the interpolation unit 3A performs the following processing.

At the time step t+4, the inertial measurement units $IMU_1$ to $IMU_3$ obtain IMU data $D0_1$(t+4) to $D0_3$(t+4), respectively, and transmit the obtained IMU data to the IMU data obtaining unit 2 of the pose data generation device 200.

The IMU data obtaining unit 2 receives data $D0_1$(t+4) to $D0_3$(t+4) transmitted from the inertial measurement units $IMU_1$ to $IMU_3$, respectively. The IMU data obtaining unit 2 obtains the received data, in which $D0_1$ to $D0_1$ are integrated, as data D1_imu(t+4), and transmits the obtained data D1_imu(t+4) to the IMU data conversion unit 4.

The IMU data conversion unit 4 receives the data D1 imu(t+4) transmitted from the IMU data obtaining unit 2. Further, the IMU data conversion unit 4 receives information Info_space regarding the three-dimensional space (imaging space) imaged by the imaging device Cam1 and the imaging parameters Info_cam_prm of the imaging device Cam1. The IMU data conversion unit 4 converts three-dimensional data D1_imu(t+4) transmitted from the IMU data obtaining unit 2 (for example, an angular velocity vector (three-dimensional data) in the three-dimensional space SP obtained by each inertial measurement unit $IMU_k$) into two-dimensional data. Specifically, based on the information Info_space regarding the three-dimensional space (imaging space) imaged by the imaging device Cam1 and the photographing parameter Info_cam_prm of the imaging device Cam1, the IMU data conversion unit 4 converts the three-dimensional coordinate data (three-dimensional data D1 imu(t+4)) into two-dimensional coordinate data in a frame image (two-dimensional image) obtained when the image is captured by the imaging device Cam1. The IMU data conversion unit 4 then transmits the data obtained by the above three-dimensional/two-dimensional coordinate conversion for the three-dimensional data D1_imu to the interpolation unit 3A as the data D2_imu(t+4).

The interpolation unit 3A obtains the two-dimensional coordinate position data $P_1^{(t+4)}$ to $P_3^{(t+4)}$ of the inertial measurement units $IMU_1$ to $IMU_3$ at the time step t+4 using (1) data (data D2 imu(t+4)) after three-dimensional/two-dimensional coordinate conversion using the IMU data $D0_1$(t+3) to $D0_3$(t+3) obtained at the time step t+3 and (2) the two-dimensional coordinate position data $P_1^{(t+3)}$ to $P_3^{(t+3)}$ of the inertial measurement units $IMU_1$ to $IMU_3$ at the time step t+3, which has been stored and held in the interpolation unit 3.

Specifically, the interpolation unit 3A performs the same processing as the processing at the time step t+1 to obtain the three-dimensional coordinate position data $P_1^{(t+4)}$ to $P_3^{(t+4)}$ of the inertial measurement units $IMU_1$ to $IMU_3$ at the time step t+4.

The interpolation unit 3A then performs the same processing as at the time step t+1 to obtain 2D pose data (2D pose data by interpolation processing). The 2D pose data obtained, at the time step t+4, by the interpolation unit 3A using the interpolation processing is referred to as 2D pose data Pose_2dH$^{(t+4)}$. In other words, the interpolation unit 3A performs processing corresponding to the following formula to obtain the 2D pose data PoseH_2d$^{(t+4)}$ obtained by the interpolation processing at the time step t+4.

$$\text{PoseH\_2d}^{(t+4)} = f2(P_1^{(t+4)}, P_2^{(t+4)}, P_3^{(t+4)}, \text{Pose\_2d}^{(t+3)})$$

The interpolation unit 3A then performs determination selection processing on the 2D pose data V_2d$^{(t+4)}$ obtained from the frame image data D_img(t+4) and the 2D pose data PoseH_2d$^{(t+4)}$ obtained by the interpolation processing (processing at the time step t+4 in the sequence diagram in FIG. 25).

Specifically, the interpolation unit 3A compares the 2D pose data V_2d$^{(t+4)}$ with the 2D pose data PoseH_2d$^{(t+4)}$; if the difference between the two is within a predetermined range, the interpolation unit 3A determines that the prediction accuracy of the interpolation processing is high, and then transmits the 2D pose data PoseH 2d$^{(t+4)}$ obtained by the interpolation processing as the 2D pose data Pose_2d$^{(t+4)}$ at the time step t+4. Conversely, if the difference between the two is out of the predetermined range, the interpolation unit 3A determines that the prediction accuracy of the interpolation processing is low, and then transmits the 2D pose data V_2d$^{(t+4)}$ obtained from the frame image data D_img$^{(t+4)}$ as the 2D pose data Pose_2d$^{(t+4)}$ at the time step t+4.

FIG. 21 shows a case where the difference between the 2D pose data V_2d$^{(t+4)}$ and the 2D pose data PoseH_2d$^{(t+4)}$ is small. Further, FIG. 22 shows a case where the difference between the 2D pose data V_2d$^{(t+4)}$ and the 2D pose data PoseH_2d$^{(t+4)}$ is large.

In the case of FIG. 21, the interpolation unit 3A performs comparison determination processing for determining whether the total sum of the norms (or Euclidean distances) of the vectors between the corresponding key points in the 2D pose data V_2d$^{(t+4)}$ and the 2D pose data PoseH_2d$^{(t+4)}$ is larger than a predetermined threshold value. The vectors between the corresponding key points shall are assumed to be set, for example, as shown in FIG. 23.

In other words, assuming that vec(a, b) is a vector from a point "a" to a point "b" in the three-dimensional space SP1, the vectors between the corresponding key points are the following 15 vectors vi to vis.

$$v_1 = vec(kp_3, kp_2)$$
$$v_2 = vec(kp_2, kp_1)$$
$$v_3 = vec(kp_3, kp_5)$$
$$v_4 = vec(kp_5, kp_6)$$
$$v_5 = vec(kp_6, kp_7)$$
$$v_6 = vec(kp_3, kp_4)$$
$$v_7 = vec(kp_3, kp_{14})$$
$$v_8 = vec(kp_{14}, kp_{15})$$
$$v_9 = vec(kp_{15}, kp_{16})$$
$$v_{10} = vec(kp_4, kp_8)$$
$$v_{11} = vec(kp_8, kp_9)$$
$$v_{12} = vec(kp_9, kp_{10})$$
$$v_{13} = vec(kp_4, kp_{11})$$
$$v_{14} = vec(kp_{11}, kp_{12})$$
$$v_{15} = vec(kp_{12}, kp_{13})$$

Note that the vectors between the key points corresponding to the 2D pose data PoseH_2d$^{(1+4)}$ are defined as the vector vi to vis, and the vectors between the key points corresponding to the 2D pose data V_2d$^{(t+4)}$ are defined as the vector v'$_1$ to v'$_{15}$.

The interpolation unit 3A then performs processing corresponding to the following formula to obtain the total Ev (evaluation value Ev) of the sum of the norms (or Euclidean distances) of the difference vectors between the corresponding key points in the 2D pose data V_2d$^{(t+4)}$ and the 2D pose data PoseH_2d$^{(t+4)}$.

$$Ev = \sum_{i=1}^{M} \|v_i - v'_i\| \qquad \text{Formula 6}$$

M. the number of vectors between key points

Then, the interpolation unit 3A then compares the evaluation value Ev obtained as described above with the predetermined threshold value Th2. Note that the evaluation value Ev for the 2D pose data PoseH_2d$^{(t+4)}$ and the 2D pose data V_2d$^{(t+4)}$ is denoted as Ev(PoseH_2d$^{(t+4)}$ V_2d$^{(t+4)}$).

(1) When Ev(PoseH_2d$^{(t+4)}$ V2d$^{(t+4)}$)> Th2 is satisfied, the interpolation unit 3A determines that the prediction accuracy of the interpolation processing performed by the pose data generation device 200 is low, and then transmits the 2D pose data V_2d$^{(t+4)}$ obtained from D_img$^{(t+4)}$ as the 2D pose data Pose_2d$^{(t+4)}$ at the time step t+4 (for example, in the case of FIG. 22).

(2) When Ev(PoseH_2d$^{(t+4)}$ V2d$^{(t+4)}$)≥ Th2 is satisfied, the interpolation unit 3A determines that the prediction accuracy of the interpolation processing performed by the pose data generation device 200 is high, and then transmits the obtained 2D pose data PoseH_2d$^{(t+4)}$ obtained by the interpolation processing as 2D pose data Pose_2d$^{(t+4)}$ at the time step t+4 (for example, in the case of FIG. 21).

Processing as described above allows the pose data generation device 200 to output, at the time step t+4, 2D pose data with higher accuracy of (1) the 2D pose data V_2d$^{(t+4)}$ obtained from the frame image data D_img$^{(t+4)}$ and (2) the 2D pose data V_2d$^{(t+4)}$ obtained by interpolation processing. In other words, at the time step t+4 at which the frame image is to be obtained, the pose data generation device 200 can verify the accuracy of the interpolation processing that has been performed up to the time step t+4; if the accuracy of the interpolation processing is poor, the pose data generation device 200 outputs the 2D pose data V_2d$^{(t+4)}$ obtained from D_img(t+4). Thus, the accuracy of the 2D pose data obtained by the pose data generation device 200 can always be maintained at a certain level or higher.

<<Processing after Time Step t+5>>

After the time step t+5, the pose data generation system 2000 repeatedly performs the same processing as described above. In other words, at the time step in which the frame image has been obtained, the same processing as the processing at the time step t+4 is performed, and at the time step in which the frame image has not been obtained, the same processing as the processing at the time steps t+1 to t+3 is performed.

As described above, (1) at the time step at which a frame image is to be obtained, the pose data generation system 2000 obtains 2D pose data based on the captured frame image by the imaging deviation Cam1, whereas (2) at the time step at which a frame image is not to be obtained, the pose data generation system 2000 predicts 2D pose data at the present time step from the previous time step(s) using IMU data, and performs interpolation processing (the above-described interpolation processing) using the prediction data, thereby obtaining 2D pose data. Thus, even when the rate (frame rate) of obtaining frame images by the imaging device Cam1 is low, the pose data generation system 2000 performs the above-described interpolation processing using IMU data, thereby obtaining 2D pose data with the high frame rate. In other words, since the pose data generation system 2000 does not need to use an imaging device for high frame rates, it can be realized at low cost, and can obtain 2D pose data by interpolation processing using IMU data, thereby obtaining highly accurate pose data (2D pose data).

In the pose data generation system 2000 of the second embodiment, the interpolation processing may be achieved by processing using a series filter as in the first modification of the first embodiment. Specifically, when action(s) of a person (or movement(s) of specific part(s) of a person) can be expressed (predicted) by a motion equation or the like, the interpolation unit 3A of the second embodiment may perform the interpolation processing for 2D pose data using data predicted by the motion equation or the like and the actual observation data (data specified from the IMU data) while applying a time series filter (for example, Kalman filter, the extended Kalman filter, the unscented Kalman filter, Particle filter, or the like).

Third Embodiment

Next, a third embodiment will be described. In the third embodiment, a CG data generation system using a pose data generation system is provided.

The same parts as those in the above embodiment (including modified examples) are designated by the same reference numerals, and detailed description thereof will be omitted.

3.1: Configuration of CG Data Generation System

Figure 26:
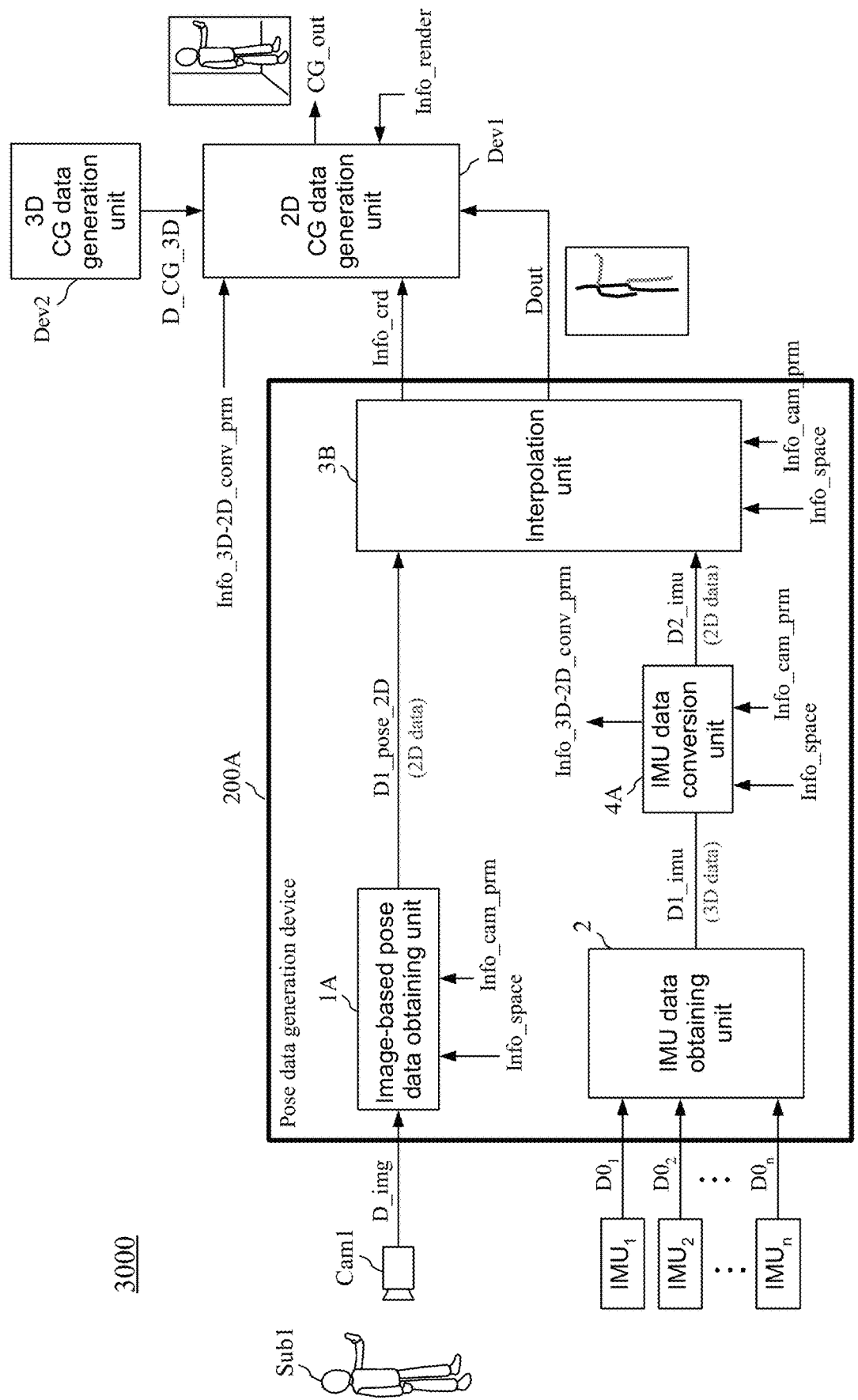
FIG. 26 is a schematic configuration diagram of a CG data generation system 3000 according to a third embodiment.

FIG. 26 is a schematic configuration diagram of the CG data generation system 3000 according to the third embodiment.

As shown in FIG. 26, the CG data generation system 3000 of the third embodiment includes an imaging device Cam1 for photographing the subject person Sub1 and n (n is a natural number) inertial measurement devices $IMU_1$ to $IMU_n$ attached to the subject person Sub1, a pose data generation device 200A, a two-dimensional CG data generation unit Dev1, and a three-dimensional CG data generation unit Dev2.

The imaging device Cam1 and the inertial measurement units $IMU_1$ to $IMU_n$ have the same configurations and functions as the imaging devices Cam1 and the inertial measurement units $IMU_1$ to $IMU_n$ of the first embodiment and the second embodiment.

The pose data generation device 200A has a configuration in which the IMU data conversion unit 4 of the pose data generation device 200 of the second embodiment is replaced with an IMU data conversion unit 4A and the interpolation unit 3A of the pose data generation device 200 of the second embodiment is replaced with an interpolation unit 3B. Other than that, the pose data generation device 200A is the same as the pose data generation device 200.

The IMU data conversion unit 4A obtains data including conversion parameters when the data D1_imu, which is 3D data transmitted from the IMU data obtaining unit 2, is converted to D2_imu, which is 2D data (3D-to-2D conversion), as data Info_3D-2D_conv_prm, and then transmits the data Info_3D-2D_conv_prm to the two-dimensional CG data generation unit Dev1. Other than this, the IMU data conversion unit 4A is the same as the IMU data conversion unit 4.

The interpolation unit 3B transmits data including (1) data for specifying 3D spatial coordinates used in the interpolation processing and (2) data for specifying 2D coordinates (coordinates in a two-dimensional image) used in the interpolation processing to the two-dimensional CG data generation unit Dev1 as data Info_crd. Other than this, the interpolation unit 3B is the same as the interpolation unit 3A of the second embodiment. Note that the interpolation unit 3A transmits the output data Dout to the two-dimensional CG data generation unit Dev1.

The two-dimensional CG data generation unit Dev1 receives (1) data Dout (two-dimensional pose data) transmitted from the interpolation unit 3B of the pose data generation device 200A and coordinate information data Info_crd, (2) data Info_3D-2D_conv_prm of 3D-2D conversion parameters transmitted from the IMU data conversion unit 4A, (3) information Info_render necessary for rendering for CG (computer graphics) (parameters required for rendering), and (4) three-dimensional CG data D_CG_3D transmitted from the three-dimensional CG data generation unit Dev2. Note that the data Info_render may be inputted from the outside of the CG data generation system 3000 via a predetermined interface; alternatively, the data Info_render has been stored and held in a storage unit (not shown) of the CG data generation system 3000, and may be inputted from the storage unit.

Based on the coordinate information data Info_crd, the 3D-2D conversion parameters Info_3D-2D_conv_prm, the parameters Info_render required for rendering, and the three-dimensional CG data D_CG_3D, the 2D CG data generation unit Dev1 performs CG data generation processing on the two-dimensional pose data Dout to generate two-dimensional CG data (data capable of forming a two-dimensional CG image), and then outputs the generated two-dimensional CG data as data CG_out.

The three-dimensional CG data generation unit Dev2 generates three-dimensional CG data, and transmits the generated three-dimensional CG data as data D_CG_3D to the two-dimensional CG data generation unit Dev1.

3.2: Operation of CG Data Generation System

The operation of the CG data generation system 3000 configured as described above will be described below.

The pose data generation device 200A of the present embodiment performs the same processing as the pose data generation device 200 of the second embodiment to obtain the two-dimensional pose data Dout. The pose data generation device 200A then transmits the obtained two-dimensional pose data Dout to the two-dimensional CG data generation unit Dev1.

The IMU data conversion unit 4A obtains data including conversion parameters when the data D1_imu, which is 3D data transmitted from the IMU data obtaining unit 2, is converted to D2_imu, which is 2D data (3D-to-2D conversion), as data Info_3D-2D_conv_prm, and then transmits the data Info_3D-2D_conv_prm to the two-dimensional CG data generation unit Dev1.

The interpolation unit 3B transmits data including (1) data for specifying 3D spatial coordinates used in the interpolation processing and (2) data for specifying 2D coordinates (coordinates in a two-dimensional image) used in the interpolation processing to the two-dimensional CG data generation unit Dev1 as data Info_crd.

The three-dimensional CG data generation unit Dev2 generates three-dimensional CG data, and transmits the generated three-dimensional CG data as data D_CG_3D to the two-dimensional CG data generation unit Dev1. For example, the three-dimensional CG data generation unit Dev2 generates three-dimensional CG data corresponding to the background of a CG object (two-dimensional CG image) that can be generated from the two-dimensional pose data of the subject person Sub1 as data D_CG_3D, and then transmits the generated data to the two-dimensional CG data generation unit Dev1. Note that the three-dimensional CD data D_CG_3D includes coordinate information for specifying the three-dimensional space when the three-dimensional CG data is generated, coordinate information for each point of the three-dimensional CG data, and data necessary for rendering such as texture.

Based on the coordinate information data Info_crd, the 3D-2D conversion parameters Info_3D-2D_conv_prm, the parameters Info_render required for rendering, and the three-dimensional CG data D_CG_3D, the 2D CG data generation unit Dev1 performs CG data generation processing on the two-dimensional pose data Dout to generate two-dimensional CG data (data capable of forming a two-dimensional CG image). Specifically, the 2D CG data generation unit Dev1 generates two-dimensional CG data corresponding to the subject person Sub1 based on the coordinate information data Info_crd, the 3D-2D conversion parameters Info_3D-2D_conv_plm, and the parameters Info_render required for rendering. Further, the two-dimensional CG data generation unit Dev1 converts the three-dimensional CD data D_CG 3D into data that can combine with two-dimensional CG data corresponding to the subject person Sub1 based on the coordinate information data Info_crd and the 3D-2D conversion parameters Info_3D-2D_conv_plm to generate two-dimensional CG data corresponding to the three-dimensional CG data D_CG_3D. The two-dimensional CG data generation unit Dev1 then synthesizes the two-dimensional CG data corresponding to the subject person Sub1 and the two-dimensional CG data (for example, background data) corresponding to the three-dimensional CG data D_CG_3D obtained as described above to obtain two-dimensional CG data and then outputs the two-dimensional CG data CG_out.

As described above, the CG data generation system 3000 of the third embodiment performs CG synthesis processing on the two-dimensional pose data obtained by the pose data generation device 200A to obtain a two-dimensional CG image corresponding to the two-dimensional pose data.

Note that in the CG data generation system 3000, the parameters of the 3D-to-2D conversion processing when the three-dimensional IMU data is converted into the two-dimensional IMU data may be matched with the parameters of the 3D-to-2D conversion processing. This allows the 3D-to-2D conversion processing to be made common, thus allowing for simplifying the 3D-to-2D conversion processing.

Fourth Embodiment

Next, a fourth embodiment will be described. In the fourth embodiment, a CG data generation system using a pose data generation system is provided.

The same parts as those in the above embodiment (including modified examples) are designated by the same reference numerals, and detailed description thereof will be omitted.

4.1: Configuration of CG Data Generation System

Figure 27:
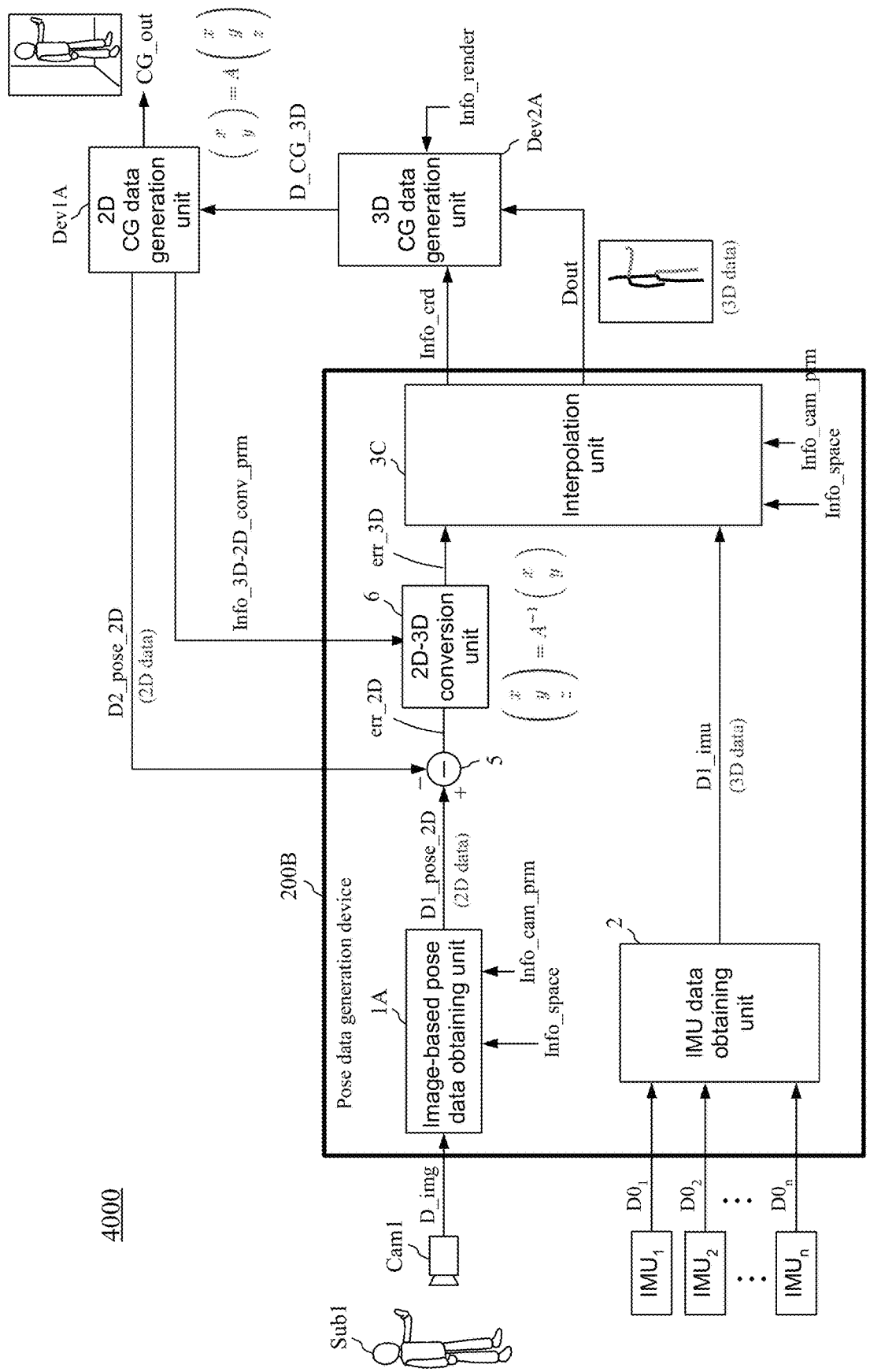
FIG. 27 is a schematic configuration diagram of a CG data generation system 4000 according to a fourth embodiment.

FIG. 27 is a schematic configuration diagram of the CG data generation system 4000 according to the fourth embodiment.

As shown in FIG. 27, the CG data generation system 4000 of the fourth embodiment includes an imaging device Cam1 for photographing a subject person Sub1, n (n is a natural numbers) inertial measurement devices $IMU_1$ to $IMU_n$ attached to the subject person Sub1, a pose data generation device 200B, a three-dimensional CG data generation unit Dev2A, and a two-dimensional CG data generation unit Dev1A.

The imaging device Cam1 and the inertial measurement units $IMU_1$ to $IMU_n$ have the same configurations and functions as the imaging device Cam1 and the inertial measurement units $IMU_1$ to $IMU_n$ of the first embodiment and the second embodiment.

The pose data generation device 200B has a configuration in which the IMU data conversion unit 4 of the pose data generation device 200 of the second embodiment is deleted, the interpolation unit 3A of the pose data generation device 200 of the second embodiment is replaced with an interpolation unit 3C, and an error obtaining unit 5 and a 2D-3D conversion unit 6 are added.

The interpolation unit 3C receives error data err_3D transmitted from the 2D-3D conversion unit 6 and data D1_imu transmitted from the IMU data obtaining unit 2. Further, the interpolation unit 3C receives information Info_space regarding the three-dimensional space (imaging space) imaged by the imaging device Cam1 and the imaging parameters Info_cam_prm of the imaging device Cam1.

(1) At a time step at which an initialization processing is to be performed and frame image data is to be obtained, the interpolation unit 3C receives data err_3D (data corresponding to data D1_pose_2D) that the 2D-3D conversion unit 6 obtains by performing 2D-to-3D conversion on data D1_pose_2D transmitted from the image-based pose data obtaining unit 1A, outputs the received data as output data Dout, and stores and holds the output data Dout.

(2) At a time step at which frame image data has not been obtained, the interpolation unit 3C performs interpolation processing using three-dimensional pose data Dout stored in the interpolation unit 3C and data D1_imu obtained at the current time step based on the information Info_space regarding the imaging space and the imaging parameters Info_cam_prm of the imaging device Cam1, thereby obtaining pose data after interpolation processing. The interpolation unit 3C then outputs the obtained pose data after interpolation processing as output data Dout, and stores and holds the output data Dout.

(3) At a time step at which frame image data has been obtained and the initialization processing is not to be performed, the interpolation unit 3C performs interpolation processing using three-dimensional pose data Dout stored in the interpolation unit 3C and data D1_imu obtained at the current time step based on the information Info_space regarding the imaging space and the imaging parameters Info_cam_prm of the imaging device Cam1, thereby obtaining pose data PoseH_3d after interpolation processing. The interpolation unit 3C then outputs the obtained pose data after the interpolation processing as output data Dout. Further, using the error data err_3D inputted from the 2D-3D conversion unit 6 and pose data PoseH_3d after interpolation processing, the interpolation unit 3C performs error correction processing for correcting pose data PoseH_3d after interpolation processing with error data err_3D to obtain pose data after correction as pose data Pose_3d. The interpolation unit 3C then transmits the obtained pose data Pose_3d as output data Dout to the three-dimensional CG data generation unit Dev2, and stores and holds the output data Dout.

Further, the interpolation unit 3C transmits the data including data for specifying the three-dimensional spatial coordinates used in the interpolation processing to the three-dimensional CG data generation unit Dev2A as data Info_crd.

The error obtaining unit 5 receives data D1_pose 2D (two-dimensional pose data) transmitted from the image-based pose data obtaining unit 1A and data D2_pose_2D (two-dimensional pose data) transmitted from the two-dimensional CG data generation unit Dev1A. The error obtaining unit 5 performs processing of subtracting the data D2_pose_2D from the data D1_pose_2D, that is, processing corresponding to the following formula to obtain error data err_2D of the two-dimensional pose data.

$$err\_2D = D1\_pose\_2D - D2\_pose\_2D$$

The error obtaining unit 5 then transmits the obtained error data err_2D for the two-dimensional pose data to the 2D-3D conversion unit 6.

The 2D-3D conversion unit 6 receives the error data err_2D transmitted from the error obtaining unit 5 and the data Info_3D-2D_conv_prm including the parameters of the 3D-2D conversion processing transmitted from the two-dimensional CG data generation unit Dev1A. The 2D-3D conversion unit 6 performs inverse conversion (3D-to-2D conversion) of the 2D-to-3D conversion performed by the two-dimensional CG data generation unit Dev1A on the error data err_2D based on the data Info_3D-2D_conv_plm, thereby obtaining three-dimensional error data err_3D corresponding to the two-dimensional error data err_2D. The 2D-3D conversion unit 6 then transmits the obtained three-dimensional error data err_3D to the interpolation unit 3C.

The three-dimensional CG data generation unit Dev2A receives the data Info_crd transmitted from the interpolation unit 3C and the data Dout transmitted from the interpolation unit 3C. Further, the three-dimensional CG data generation unit Dev2A receives information (parameters necessary for rendering) Info_render necessary for rendering for CG (computer graphics). Note that the data Info_render, which is information necessarily for rendering for CG (computer graphics), may be inputted from the outside of the CG data generation system 4000 via a predetermined interface; alternatively, the data Info_render has been stored and held in a storage unit (not shown) of the CG data generation system 4000, and may be inputted from the storage unit. Further, the data Info_render may be stored in advance in the three-dimensional CG data generation unit Dev2A.

The 3D CG data generation unit Dev2A performs CG data generation processing on data Dout, which is three-dimensional pose data, based on the data Info_render and the data Info_crd to obtain three-dimensional CG data. The three-dimensional CG data generation unit Dev2A then transmits data including the obtained three-dimensional CG data and the three-dimensional pose data Dout to the two-dimensional CG data generation unit Dev1A as data D_CG_3D.

The two-dimensional CG data generation unit Dev1A receives the data D_CG_3D transmitted from the three-dimensional CG data generation unit Dev2A. The 2D CG data generation unit Dev1A performs 3D-to-2D conversion on three-dimensional CG data included in the data D_CG_3D to generate two-dimensional CG data CG_out. The two-dimensional CG data generation unit Dev1A then transmits the generated two-dimensional CG_out.

Further, the two-dimensional CG data generation unit Dev1 A performs 3D-to-2D conversion on three-dimensional data included in the data D_CG_3D to obtain two-dimensional pose data. The two-dimensional CG data generation unit Dev1 A then transmits data including the obtained two-dimensional pose data as data D2_pose_2D to the error obtaining unit 5 of the pose data generation device 200B.

4.2: Operation of CG Data Generation System

The operation of the CG data generation system 4000 configured as described above will be described below.

Figure 28:
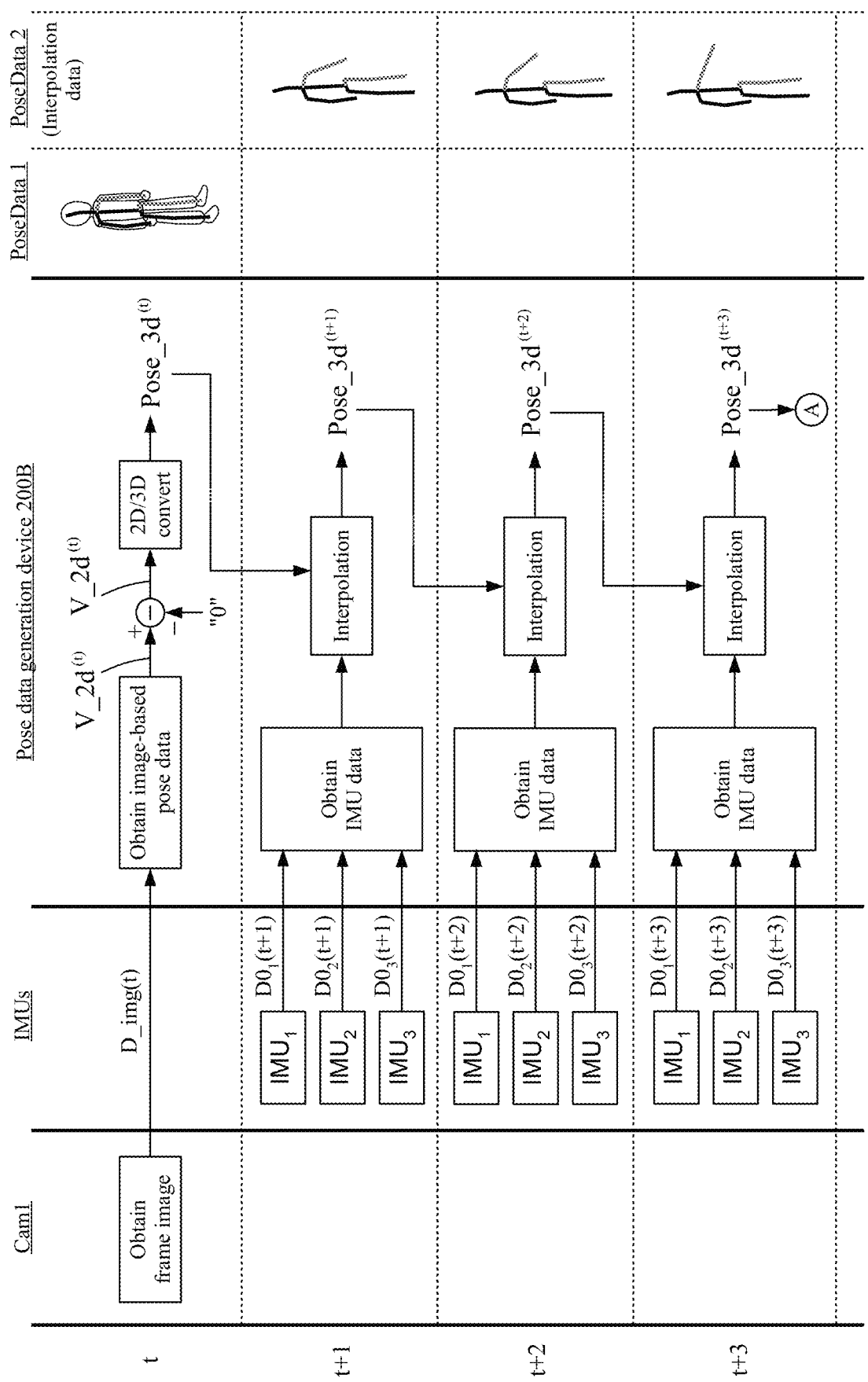
FIG. 28 is a sequence diagram of processing performed by the CG data generation system 4000.
Figure 29:
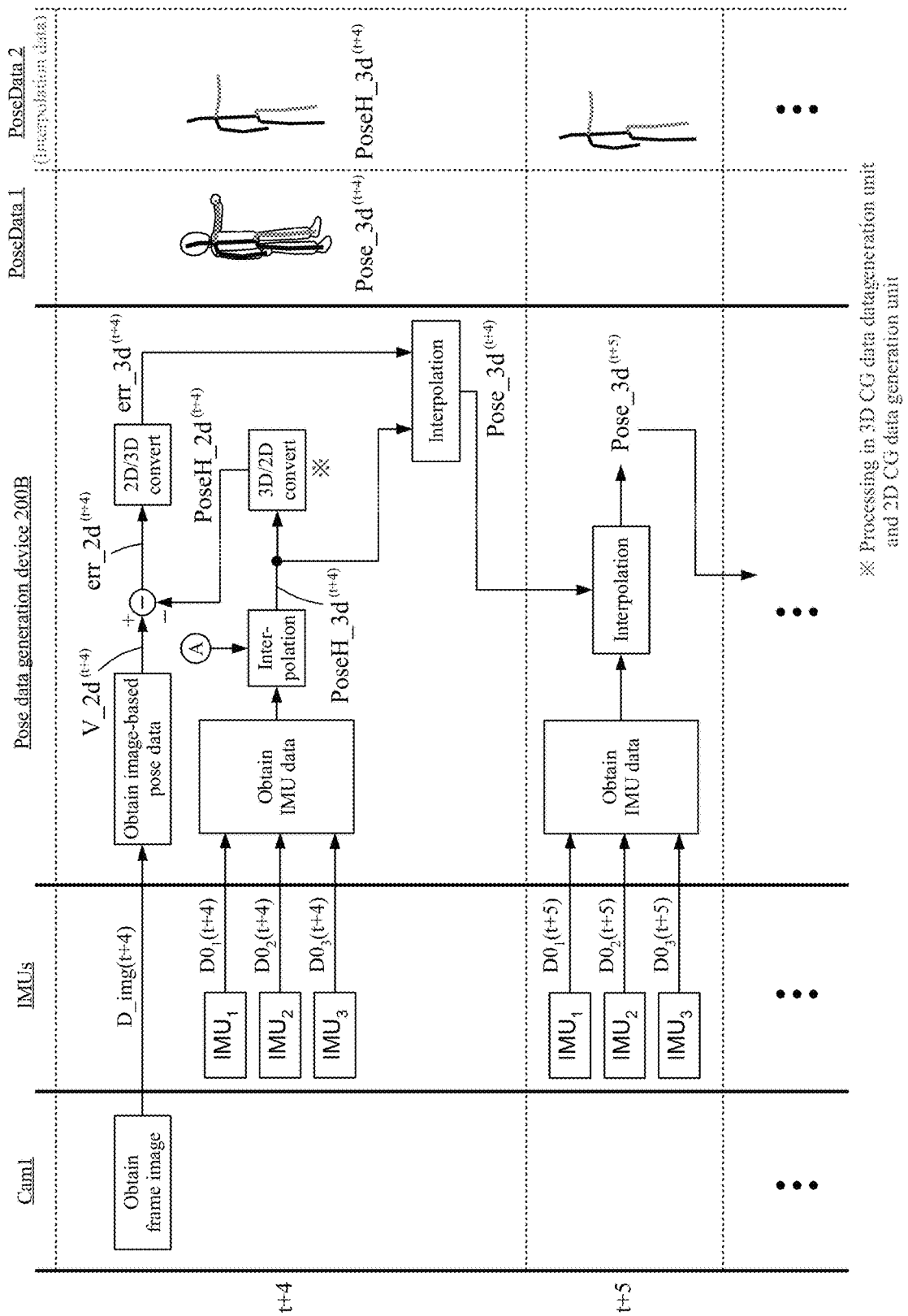
FIG. 29 is a sequence diagram of processing performed by the CG data generation system 4000.

FIGS. 28 and 29 are sequence diagrams of processes performed by the CG data generation system 4000. In FIGS. 28 and 29, the column shown by "PoseData1" shows the pose data obtained by the processing using the frame image data, and the column shown by "PoseData2" shows the pose obtained by the interpolation processing.

Hereinafter, the operation of the CG data generation system 4000 will be described with reference to FIGS. 28 and 29. A detailed description of the same parts as those in the above embodiment will be omitted.

<<Processing at Time Step t>>

At the time step t, the frame image data D_img(t) is obtained by capturing an image of the three-dimensional space (imaging space SP1) including the subject person Sub1 by the imaging Cam1. The image (frame image) formed by the frame image data D_img(t) is, for example, the image Img1 shown in the upper left figure of FIG. 16

The image-based pose data obtaining unit 1A receives the frame image data D_img(t) transmitted from the imaging device Cam1, performs processing for obtaining two-dimensional pose data from the frame image data D_img(t) to obtain two-dimensional pose data D1_pose_2D (=V2d$^{(t)}$).

The 2D pose data obtaining unit 12A then transmits the obtained two-dimensional pose data D1_pose_2D (=V_2d$^{(t)}$) to the error obtaining unit 5.

The error obtaining unit 5 performs processing of subtracting the data D2_pose_2D transmitted from the two-dimensional CG data generation unit Dev1A from the data D1_pose_2D (=V_2d( ) transmitted from the image-based pose data obtaining unit TA; that is, it performs processing corresponding to the following formula.

$$err\_2D = D1\_pose\_2D - D2\_pose\_2D$$

At time t, initialization processing is performed at time t, and the data D2_pose_2D is "0" (or no input); thus, the following formula is satisfied.

$$err\_2D = D1\_pose\_2D$$

The error obtaining unit 5 transmits the error data err 2D (=D1_pose_2D=V_2d$^{(t)}$) of the two-dimensional pose data obtained as described above to the 2D-3D conversion unit 6.

The 2D-3D conversion unit 6 performs inverse conversion (3D-to-2D conversion) of the 2D-to-3D conversion performed by the two-dimensional CG data generation unit Dev1A on the error data err_2D (=V_2d$^{(t)}$) based on the data Info_3D-2D_conv_prm, thereby obtaining three-dimensional error data err_3D(=Pose 3d$^{(t)}$ corresponding to the two-dimensional error data err_2D. The 2D-3D conversion unit 6 then transmits the obtained three-dimensional error data err_3D (=Pose_3d$^{(t)}$) to the interpolation unit 3C.

since the time step t is a time step at which the frame image data has been obtained and the initialization process is to be performed, the interpolation unit 3C transmits the data err 3D (=Pose_3d( )) inputted from the 2D-3D conversion unit 6 to the three-dimensional CG data generation unit Dev2A as output data Dout (three-dimensional pose data Dout), and stores and holds the output data Dout. Further, the interpolation unit 3C transmits data including data for specifying the three-dimensional spatial coordinates used for the processing (interpolation processing, or the like) in the interpolation unit 3C to the three-dimensional CG data generation unit Dev2A as data Info_crd.

The three-dimensional CG data generation unit Dev2A receives the data Info_crd transmitted from the interpolation unit 3C and the data Dout transmitted from the interpolation unit 3C. Further, the three-dimensional CG data generation unit Dev2A receives information (parameters necessary for rendering) Info_render necessary for rendering for CG (computer graphics).

The three-dimensional CG data generation unit Dev2A then performs CG data generation processing on the data Dout (=Pose_3d$^{(t)}$), which is the three-dimensional pose data, based on the data Info_render and the data Info_crd to obtain three-dimensional CG data. The 3D CG data generation unit Dev2A then transmits data including the obtained three-dimensional CG data and the three-dimensional pose data Dout (=Pose_3d(O) to the two-dimensional CG data generation unit Dev1A as data D_CG_3D.

The two-dimensional CG data generation unit Dev1A receives the data D_CG_3D transmitted from the three-dimensional CG data generation unit Dev2A. The 2D CG data generation unit Dev1A performs 3D-to-2D conversion on data included in the data D_CG_3D to generate two-dimensional CG data CG_out. The two-dimensional CG data generation unit Dev1A then outputs the generated two-dimensional CG_out.

<<Processing at Time Steps t+1 to t+3>>

At each time step of the time steps t+1 to t+3, the CG data generation system 4000 performs the same processing as in the first embodiment (including the modification) (processing for each time step of the time steps t+1 to t+3) to obtain three-dimensional pose data Pose_3d$^{(t+1)}$ to Pose_3d$^{(t+3)}$. The CG data generation system 4000 performs processing by the three-dimensional CG data generation unit Dev2A and processing by the two-dimensional CG data generation unit Dev1A and in the same manner as described above using the three-dimensional pose data Pose_3d$^{(t+1)}$ to Pose_3d$^{(t+1)}$, thereby obtaining two-dimensional CG data CG_out.

<<Processing of Time Step t+4>>

At the time step t+4, the inertial measurement units $IMU_1$ to $IMU_3$ obtain IMU data $D0_1$(t+4) to $D0_3$(t+4), respectively, as in processes of the time steps t+1 to t+3, and then transmits the obtained IMU data to the IMU data obtaining unit 2 of 200B. The interpolation unit 3C then performs the same interpolation processing as processing at the time steps t+1 to t+3 to obtain three-dimensional pose data PoseH_3d$^{(t+4)}$ after interpolation processing. The interpolation unit 3C then transmits the three-dimensional pose data PoseH_3d$^{(t+4)}$ after interpolation processing to the three-dimensional CG data generation unit Dev2A as data Dout.

The three-dimensional CG data generation unit Dev2A receives the data Info_crd transmitted from the interpolation unit 3C and the data Dout (=PoseH_3d$^{(t+4)}$) transmitted from the interpolation unit 3C. Further, the three-dimensional CG data generation unit Dev2A receives information (parameters necessary for rendering) Info_render necessary for rendering for CG (computer graphics).

The three-dimensional CG data generation unit Dev2A performs CG data generation processing on the data Dout (=PoseH_3d$^{(t+4)}$, which is the three-dimensional pose data, based on the data Info_render and the data Info_crd to obtain three-dimensional CG data. The three-dimensional CG data generation unit Dev2A then transmits data including the obtained three-dimensional CG data and the three-dimensional pose data Dout (=PoseH_3d$^{(t+4)}$) to the two-dimensional CG data generation unit Dev1A as data D_CG_3D.

The two-dimensional CG data generation unit Dev1A receives the data D_CG_3D transmitted from the three-dimensional CG data generation unit Dev2A. The two-dimensional CG data generation unit Dev1A performs 3D-to-2D conversion on three-dimensional CG data included in the data D_CG_3D to generate two-dimensional CG data CG_out, and also performs 3D-to-2D conversion on three-dimensional pose data PoseH_3D$^{(t+4)}$ included in the data D_CG_3D to generate two-dimensional pose data PoseH_2d$^{(t+4)}$. The two-dimensional CG data generation unit Dev1A then transmits data including the obtained two-dimensional pose data PoseH_2d$^{(t+4)}$ as the data D2_pose_2D to the error obtaining unit 5 of the pose data generation device 200B.

Further, at the time step t+4, the frame image data D_img(t+4) is obtained by imaging the three-dimensional space (imaging space SP1) including the subject person Sub1 by the imaging device Cam1.

The image-based pose data obtaining unit TA performs the same processing as the processing at the time step t to obtain two-dimensional pose data D1_pose_2D(t+4) (=V_2d$^{(t+4)}$) from the frame image data D_img(t+4) transmitted from the imaging device Cam1, The 2D pose data obtaining unit 12A then transmits the obtained two-dimensional pose data D1_pose_2D (=V_2d$^{(t+4)}$) to the error obtaining unit 5.

The error obtaining unit 5 receives the data D1_pose_2D (=V_2d$^{(t+4)}$) transmitted from the image-based pose data obtaining unit TA and the data D2_pose_2D (=PoseH_2d$^{(t+4)}$) transmitted from the two-dimensional CG data generation unit Dev1A. The error obtaining unit 5 performs processing of subtracting the data D2_pose_2D (=PoseH_2d$^{(t+4)}$) from the data D1_pose 2D (=V_2d($^{(t+4)}$); that is, it performs processing corresponding to the following formula to obtain error data err 2D (=err_2d$^{(t+4)}$) of the two-dimensional pose data.

$$\text{err\_}2D = D1\_pose\_2D - D2\_pose\_2D$$

$$\left(\text{Err\_}2d^{(t+4)} = V\_2d^{(t+4)} - \text{PoseH\_}2d^{(t+4)}\right)$$

The error obtaining unit 5 then transmits the error data err_2D (err_2d$^{(t+4)}$) of the obtained two-dimensional pose data to the 2D-3D conversion unit 6.

The 2D-3D conversion unit 6 performs inverse conversion (3D-to-2D conversion) of the 2D-to-3D conversion performed by the two-dimensional CG data generation unit Dev1A on the error data err_2D (=err 2d$^{(t+4)}$) based on the data Info_3D-2D_conv_prm, thereby obtaining three-dimensional error data err_3D(=err_3d$^{(t+4)}$) corresponding to the two-dimensional error data err_2D. The 2D-3D conversion unit 6 then transmits the obtained three-dimensional error data err_3D (=err 3d$^{(t+4)}$) to the interpolation unit 3C.

Using the error data err_3D (=err 3d(t+$^4$)) inputted from the 2D-3D conversion unit 6 and pose data PoseH_3d$^{(t+4)}$ after interpolation processing, the interpolation unit 3C performs error correction processing for correcting pose data PoseH_3d$^{(t+4)}$ after interpolation processing with error data err 3D (=err 3d$^{(t+4)}$) to obtain pose data after correction as pose data Pose_3d. For example, the interpolation unit 3C performs processing for subtracting error data err_3D (=err_3d$^{(t+4)}$) (processing for reducing error(s)) so that the pose data PoseH_3d$^{(t+4)}$ after interpolation processing approaches the three-dimensional pose data V_3d$^{(t+4)}$ corresponding to the two-dimensional pose data V_2d$^{(t+4)}$ obtained by the image-based pose data obtaining unit 1A (so that two-dimensional pose data V_2d$^{(t+4)}$ approaches three-dimensional pose data V_3d$^{(t+4)}$ obtained by 2D-to-3D conversion), thereby performing error correction processing. For example, the interpolation unit 3C performs processing corresponding to the following formula, thereby performing error correction processing.

$$\text{Pose\_3}d^{(t+4)} = \text{PoseH\_3}d^{(t+4)} - k1 \times \text{err\_3}d^{(t+4)}$$

k1: coefficient

The interpolation unit 3C then transmits the pose data Pose_3d$^{(t+4)}$ after the error correction processing obtained by the error correction processing as output data Dout to the three-dimensional CG data generation unit Dev2, and stores and holds the output data Dout.

The 3D CG data generation unit Dev2A performs CG data generation processing on the three-dimensional pose data Dout (=Pose_3d$^{(t+4)}$ transmitted from the interpolation unit 3C based on the data Info_render and the data Info_crd to obtain three-dimensional CG data. The three-dimensional CG data generation unit Dev2A then transmits data including the obtained three-dimensional CG data and the three-dimensional pose data Dout (=Pose 3d$^{(t+4)}$) to the two-dimensional CG data generation unit Dev1A as data D_CG_3D.

The two-dimensional CG data generation unit Dev1A receives the data D_CG_3D transmitted from the three-dimensional CG data generation unit Dev2A. The 2D CG data generation unit Dev1A performs 3D-to-2D conversion on three-dimensional CG data included in the data D_CG_3D to generate two-dimensional CG data CG_out. The two-dimensional CG data generation unit Dev1A then outputs the generated two-dimensional CG_out.

<<Processing after Time Step t+5>>

After the time step t+5, the CG data generation system 4000 repeatedly performs the same processing as described above. In other words, at the time step at which the frame image is to be obtained, the same processing as the processing at the time step t+4 is performed, and at the time step at which the frame image is not to be obtained, the same processing as the processing at the time steps t+1 to t+3 is performed.

As described above, at the time step at which a frame image is to be obtained by the imaging device Cam1, the CG data generation system 4000 performs error correction processing on three-dimensional pose data obtained by interpolation processing from IMU data using the error data between the captured frame image and the two-dimensional pose data obtained by the interpolation processing from IMU data, the three-dimensional CG data generation processing, and the three-dimensional CG data generation processing. This allows the CG data generation system 4000 to obtain three-dimensional pose data after the error correction processing. In other words, the CG data generation system 4000 performs the above-described error correction processing at the time step at which a frame image is to be obtained, thus allowing for obtaining highly accurate three-dimensional pose data; furthermore, performing three-dimensional CG generation processing and two-dimensional CG generation processing in the CG data generation system 4000 using the above three-dimensional pose data allows for generating highly accurate CG data.

Similarly to the above embodiment (including the modification), in the period between the time steps at which the frame image has been obtained (the period in which the frame image has not been obtained), the CG data generation system 4000 predicts 3D pose data from the previous time step to the current time step with IMU data and performs interpolation processing (the above-described interpolation processing), thereby obtaining 3D pose data. Thus, even when the rate (frame rate) of obtaining frame images by the imaging device Cam1 is low, the CG data generation system 4000 performs the above-described interpolation processing using IMU data, thereby obtaining 3D pose data with the high frame rate.

Note that at the time step at which the frame image is to be obtained and the initialization process is to be performed, the subject person Sub1 may strike a predetermined pose that the CG data generation system 4000 can easily estimate three-dimensional pose data. This allows the error between the pose of the subject person Sub1 at the time of initialization processing and the three-dimensional pose data obtained by the CG data generation system 4000 to be zero or minimized. As a result, the CG data generation system 4000 can obtain more accurate three-dimensional pose data.

Other Embodiments

In the above embodiment (including a modification), a case where the image-based pose data obtaining unit processes the pose data (image-based pose data) from the frame image data by using a single frame image has been described; however, the present invention should not be limited to this. For example, the pose data obtaining unit may perform processing (for example, processing with a neural network) of obtaining pose data (image-based pose data) from frame image data using a plurality of frame images (for example, a plurality of frame images continuous in time series) to obtain pose data (image-based pose data). Note that if the timing at which the pose data (image-based pose data) is obtained and the timing at which the IMU data is obtained deviate from each other, the pose data generation device may, for example, delay the IMU data so that the timings of the two are matched and then perform interpolation processing or the like.

Further, in the above embodiment (including the modification), the case where the number of inertial measurement units is "3" has been described, but the present invention should not be limited to this, and the number of inertial measurement units may be other than three. Further, the mounting positions of the inertial measurement units should not be limited to the case of the above embodiment (including the modification), and the inertial measurement units may be attached to any part of the processing target (for example, a person).

Further, in the pose data generation system of the first embodiment (including a modification), a three-dimensional CG data generation unit may be provided after the pose data generation device to obtain (generate) three-dimensional CG data from the three-dimensional pose data.

Further, the example of setting the coordinate system in the above embodiment (including the modified example) is an example, and should not be limited to the above. Further, instead of the Cartesian coordinate system, another coordinate system (for example, a polar coordinate system) may be used.

Further, each block (each functional unit) of the pose data generation system, the CG data system, and the pose data generation device described in the above embodiment may be individually integrated into one chip with a semiconductor device such as an LSI, or a part thereof; alternatively, it may be made into one chip so as to include all of them. Further, each block (each functional unit) of the pose data generation system, the CG data system, and the pose data generation device described in the above embodiment may be provided with a plurality of semiconductor devices such as a plurality of LSIs.

Note that although the term LSI is used here, it may also be called IC, system LSI, super LSI, or ultra LSI depending on the degree of integration.

Further, the method of circuit integration should not be limited to LSI, and it may be implemented with a dedicated circuit or a general-purpose processor. A field programmable gate array (FPGA) that can be programmed after the LSI is manufactured, or a reconfigurable processor that can reconfigure connection and setting of circuit cells inside the LSI may be used.

Further, a part or all of the processing of each functional block of each of the above embodiments may be implemented with a program. A part or all of the processing of each functional block of each of the above-described embodiments is then performed by a central processing unit (CPU) in a computer. The programs for these processes may be stored in a storage device, such as a hard disk or a ROM, and may be executed from the ROM or be read into a RAM and then executed.

The processes described in the above embodiments may be implemented by using either hardware or software (including use of an operating system (OS), middleware, or a predetermined library), or may be implemented using both software and hardware.

Figure 30:
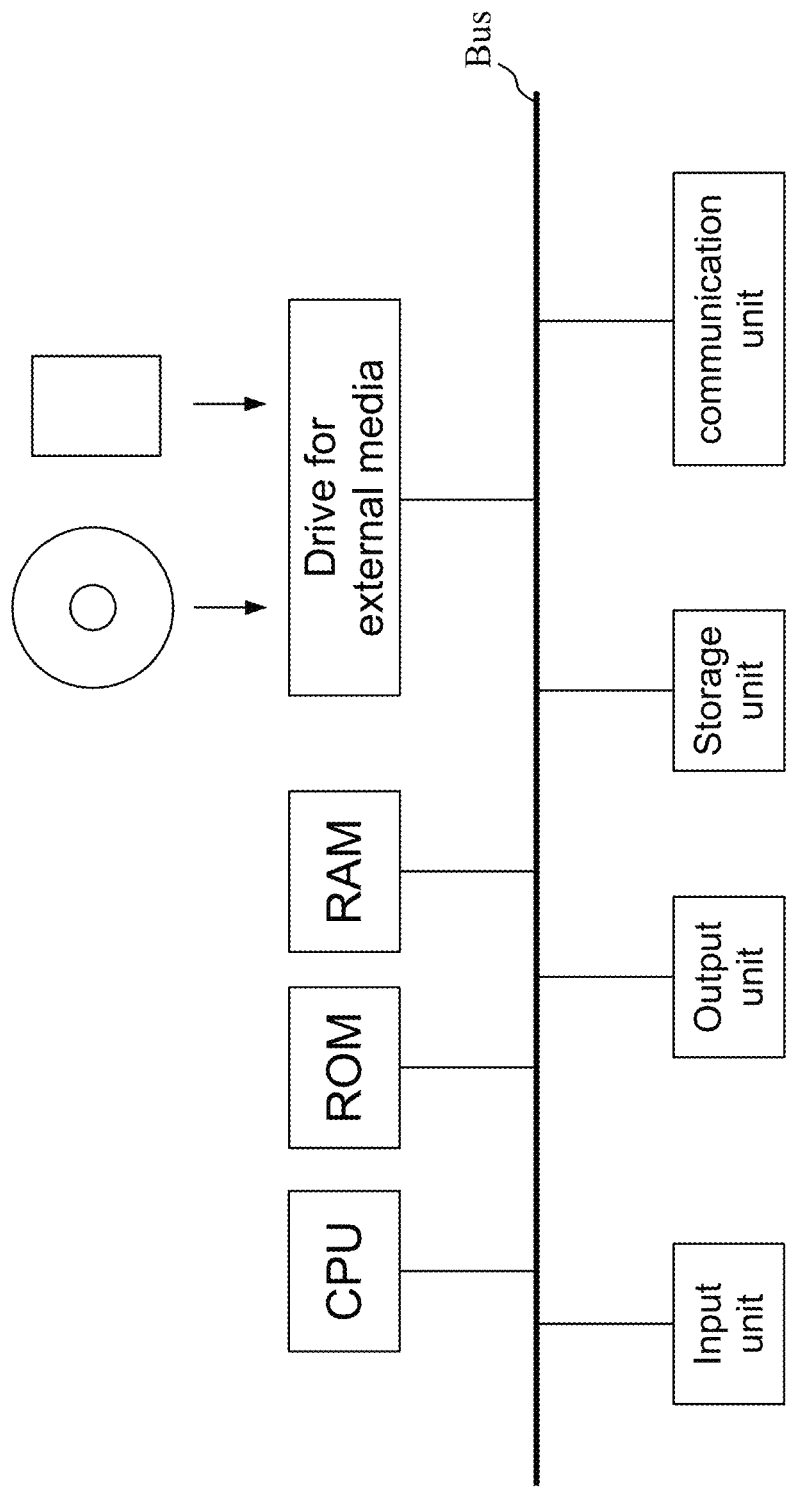
FIG. 30 is a diagram showing a CPU bus configuration.

For example, when functional units of the above embodiments (including modifications) and modifications is achieved by using software, the hardware structure (the hardware structure including CPU, GPU, ROM, RAM, an input unit, an output unit or the like, each of which is connected to a bus) shown in FIG. 30 may be employed to achieve the functional units by using software.

The processes described in the above embodiments may not be performed in the order specified in the above embodiments. The order in which the processes are performed may be changed without departing from the scope and the spirit of the invention.

The present invention may also include a computer program enabling a computer to implement the method described in the above embodiments and a computer readable recording medium on which such a program is recorded. Examples of the computer readable recording medium include a flexible disk, a hard disk, a CD-ROM, an MO, a DVD, a DVD-ROM, a DVD-RAM, a large capacity DVD, a next-generation DVD, and a semiconductor memory.

The computer program may not be recorded on the recording medium but may be transmitted with an electric communication line, a wireless or hard-wired communication line, or a network such as the Internet.

The term "unit" may include "circuitry," which may be partly or entirely implemented by using either hardware or software, or both hardware and software.

The functionality of the elements disclosed herein may be implemented using circuitry or processing circuitry which includes general purpose processors, special purpose processors, integrated circuits, ASICs ("Application Specific Integrated Circuits"), conventional circuitry and/or combinations thereof which are configured or programmed to perform the disclosed functionality. Processors are considered processing circuitry or circuitry as they include transistors and other circuitry therein. In the disclosure, the circuitry, units, or means are hardware that carry out or are programmed to perform the recited functionality. The hardware may be any hardware disclosed herein or otherwise known which is programmed or configured to carry out the recited functionality. When the hardware is a processor which may be considered a type of circuitry, the circuitry, means, or units are a combination of hardware and software, the software being used to configure the hardware and/or processor.

The specific structures described in the above embodiments are mere examples of the present invention, and may be changed and modified variously without departing from the scope and the spirit of the invention.

REFERENCE SIGNS LIST 1000, 2000 pose data generation system
3000, 4000 CG data generation system
100, 200, 200A, 200B pose data generator
1,1A image-based pose data obtaining unit
2 IMU data obtaining unit
3, 3A, 3B interpolation unit
4, 4A IMU data conversion unit
5 error obtaining unit
6 2D-3D conversion unit
$IMU_1$ to $IMU_n$ inertial measurement unit

What is claimed is:
1. A pose data generation device comprising:
image-based pose data obtaining circuitry that obtains image-based pose data, which is data including posture information of a subject, from image data obtained by imaging the subject in a three-dimensional space at a time step t (t is an integer);
inertial measurement unit (IMU) data obtaining processing circuitry that obtains IMU data outputting from an inertial measurement unit attached to the subject, the IMU data including at least one of position data, displacement data, velocity data, acceleration data, and angular velocity data in the three-dimensional space of the inertial measurement unit attached to the subject; and interpolation circuitry that, at a timing within a period between a time step t and a time step t+k (k is a natural number) wherein the time step t+k is a timing at which image data is to be obtained next to the time step t at which image data has been obtained, performs interpolation processing both on the image-based pose data and the IMU data to obtain interpolation pose data that is interpolated data for pose data of the subject, the interpolation pose data corresponding to pose data at a timing when the IMU data obtaining processing circuitry has obtained the IMU data, and wherein a frame rate that the image data is to be obtained is less than a frame rate of the interpolated pose data including the image-based pose data and the interpolation pose data.

2. The pose data generation device according to claim 1, wherein the image-based pose data obtaining circuitry obtains the image-based pose data, which is three-dimensional data, from the image data.

3. The pose data generation device according to claim 1, wherein the image-based pose data obtaining circuitry obtains the image-based pose data, which is two-dimensional data, from the image data, the IMU data is three-dimensional data, and the IMU data obtaining processing circuitry performs a three-dimension to two-dimension conversion processing on the IMU data, which is three-dimensional data, to obtain IMU data that is two-dimensional data.

4. The pose data generation device according to claim 1, wherein the image-based pose data obtaining circuitry obtains the image-based pose data, which is two-dimensional data, from the image data, the IMU data is three-dimensional data, the interpolation pose data is three-dimensional data, and the pose data generation device further comprising:

error obtaining circuitry that obtains two-dimensional error data, which is data including an error between the image-based pose data and the two-dimensional interpolation pose data, which is data obtained by converting the interpolation pose data, which is three-dimensional data, into two-dimensional data, and 2D/3D conversion circuitry that obtains three-dimensional error data by converting the two-dimensional error data into three-dimensional data, wherein the interpolation circuitry performs processing for correcting the error based on the three-dimensional error data on the interpolation pose data to obtain interpolation pose data after error correction processing.

5. The pose data generation device according to claim 1, wherein assuming that a frame rate of the pose data generated by the pose data generation device is $R_1$ fps ($R_1$ is a real number, fps: frames per second), the image-based pose data obtaining circuitry obtains the image-based pose from the image data obtained at a frame rate of $0.5 \times Ri$ fps or less.

6. The pose data generation device according to claim 1, wherein at the time step at which the image data is to be obtained, the interpolation circuitry compares the image-based pose data obtained from the image data with the interpolation pose data obtained by the interpolation processing, (1) when a difference between the image-based pose data obtained from the image data and the interpolation pose data obtained by the interpolation processing is larger than a predetermined threshold value, the interpolation circuitry sets the image-based image obtained from the image data as output data from the pose data generation device, (2) when a difference between the image-based pose data obtained from the image data and the interpolation pose data obtained by the interpolation processing is equal to or less than the predetermined threshold value, the interpolation circuitry sets the interpolation pose data obtained by the interpolation processing as output data from the pose data generation device.

7. The pose data generation device according to claim 1, wherein the interpolation circuitry performs the interpolation processing by performing processing using a time series filter.

8. A computer graphics (CG) data generation system comprising:

the pose data generation device according to claim 3; and

CG data generation circuitry that generates two-dimensional CG data from three-dimensional CG data and generates two-dimensional CG data from two-dimensional pose data, wherein the CG data generation circuitry performs processing for converting three-dimensional CG data to two-dimensional CG data based on conversion parameters, which the IMU data obtaining processing circuitry has used in 3D-to-2D conversion processing for obtaining IMU data which is 2D data, to obtain CG data for two-dimensional synthesis, and synthesize the obtained CG data for two-dimensional synthesis and two-dimensional CG data generated from the two-dimensional pose data to obtain CG data for outputting.

9. A computer graphics (CG) data generation system comprising:

the pose data generation device according to claim 4;

three-dimensional CG data generation circuitry that performs CG processing based on three-dimensional pose data to generate three-dimensional CG data; and two-dimensional CG data generation circuitry that performs 3D/2D conversion processing for converting three-dimensional CG data generated by the three-dimensional CG data generation circuitry to two-dimensional data to obtain two-dimensional CG data;

wherein the error obtaining circuitry uses two-dimensional pose data corresponding to the two-dimensional CG data obtained by the two-dimensional CG data generation circuitry as the two-dimensional interpolation pose data, and obtains two-dimensional error data that is data including the two-dimensional interpolation pose data and the image-based pose data.

10. The pose data generation device according to claim 1, wherein the image-based pose data obtaining circuitry further obtains camera parameters of a camera that captured the image data.

11. The pose data generation device according to claim 10, wherein the camera parameters include at least one of image angle, aperture, focal length, and shutter speed.

12. A pose data generation method comprising:

an image-based pose data obtaining step of obtaining image-based pose data, which is data including posture information of a subject, from image data obtained by imaging the subject in a three-dimensional space at a time step t (t is an integer);

an inertial measurement unit (IMU) data obtaining processing step of obtaining IMU data outputting from an inertial measurement unit attached to the subject, the IMU data including at least one of position data, displacement data, velocity data, acceleration data, and angular velocity data in the three-dimensional space of the inertial measurement unit attached to the subject; and an interpolation step of, at a timing within a period between a time step t and a time step t+k (k is a natural number) wherein the time step t+k is a timing at which image data is to be obtained next to the time step t at which image data has been obtained, performing interpolation processing both on the image-based pose data and the IMU data to obtain interpolation pose data that is interpolated data for pose data of the subject, the interpolation pose data corresponding to pose data at a timing when the IMU data obtaining processing circuitry has obtained the IMU data, and wherein a frame rate that the image data is to be obtained is less than a frame rate of the interpolated pose data including the image-based pose data and the interpolation pose data.

13. A non-transitory computer readable storage medium storing a program for causing a computer to execute the pose data generation method according to claim 12.

* * * * *